US012629417B2

(12) United States Patent
Curtiss

(10) Patent No.: US 12,629,417 B2
(45) Date of Patent: May 19, 2026

(54) LIVE SELF-DESTRUCTING BACTERIAL ADJUVANTS TO ENHANCE INDUCTION OF IMMUNITY

(71) Applicant: UNIVERSITY OF FLORIDA RESEARCH FOUNDATION, INCORPORATED, Gainesville, FL (US)

(72) Inventor: Roy Curtiss, Gainesville, FL (US)

(73) Assignee: UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 559 days.

(21) Appl. No.: 17/922,499

(22) PCT Filed: Apr. 30, 2021

(86) PCT No.: PCT/US2021/030077
§ 371 (c)(1),
(2) Date: Oct. 31, 2022

(87) PCT Pub. No.: WO2021/222696
PCT Pub. Date: Nov. 4, 2021

(65) Prior Publication Data
US 2023/0165955 A1     Jun. 1, 2023

Related U.S. Application Data

(60) Provisional application No. 63/017,866, filed on Apr. 30, 2020.

(51) Int. Cl.
*A61K 39/39*          (2006.01)
*A61K 39/00*          (2006.01)
*C12N 1/36*           (2006.01)
*C12R 1/42*           (2006.01)

(52) U.S. Cl.
CPC ................ *A61K 39/39* (2013.01); *C12N 1/36* (2013.01); *A61K 2039/522* (2013.01); *A61K 2039/55511* (2013.01); *C12R 2001/42* (2021.05)

(58) Field of Classification Search
None
See application file for complete search history.

(56) References Cited

U.S. PATENT DOCUMENTS

2006/0233829 A1    10/2006    Curtiss, III
2019/0185520 A1     6/2019    Curtiss, III

FOREIGN PATENT DOCUMENTS

WO    WO-2018018041 A1 *    1/2018    ............. A61K 39/12
WO    2020096994 A1         5/2020

OTHER PUBLICATIONS

Wang, Shifeng et al., "Salmonella Vaccine Vectors Displaying Delayed Antigen Synthesis In Vivo To Enhance Immunogenicity", Infection and Immunity, Sep. 2010, vol. 78, No. 9, pp. 3969-3980.
Whitfield, Chris, "Biosynthesis and Assembly of Capsular Polysaccharides in *Escherichia coli*", Annu. Rev. Biochem., 2006, vol. 75, pp. 39-68.
Xin, Wei et al., "The Asd+-DadB+ Dual-Plasmid System Offers a Novel Means To Deliver Multiple Protective Antigens by a Recombinant Attenuated Salmonella Vaccine", Infection and Immunity, Oct. 2012, vol. 80, No. 10, pp. 3621-3633.
PCT Search Report & Written Opinion, PCT/US2021/030077, mailed Oct. 12, 2021, 13 pages.
Amann, Egon et al., "Tightly regulated tac promoter vectors useful for the expression of unfused and fused proteins in *Escherichia coli*", Gene, 1988, vol. 69, pp. 301-315.
Baldridge, Megan T. et al.. "Inflammatory signals regulate hematopietic stem cells", Trends Immunol., Feb. 2011, vol. 32, No. 2, pp. 57-65.
Belisle, John T. et al., "Role of the Major Antigen of Mycobacterium tuberculosis in Cell Wall Biogenesis", Science, May 30, 1997, vol. 276, pp. 1420-1422.
Bertani, G. "Studies on Lysogenesis", Department of Bacteriology, May 14, 1951, vol. 62, pp. 293-300.
Berthet, Francois-Xavier et al., A Mycobacterium tuberculosis operon encoding ESAT-6 and a novel low-molecular-mass culture filtrate protein (CFP-10) Microbiology, 1998, vol. 144, pp. 3195-3203.
Beuzon, Carmen R. et al., "Salmonella maintains the integrity of its intracellular vacuole through the action of SifA", The EMBO Journal, 2000, vol. 19, No. 13, pp. 3235-3249.
Black, Simon et al., " Aspartic B-Semialdehyde Dehydrogenase and Aspartic-Semialdehyde", National Institute of Arthritis and Metabolic Diseases, National Institutes of Health, United States Public Health Service, Bethesda, MD, Jul. 26, 1954, pp. 39-50.
Brosius, Jurgen et al., "Spacing of the -10 and -35 Regions in the tac Promoter", The Journal of Biological Chemistry, 1985, vol. 260, No. 6, Issue of Mar. 25, pp. 3539-3541.
Buchmeier, N A et al, "Recombination-deficient mutants of *Salmonella typhimurium* are avirulent and sensitive to the oxidative burst of macrophages", Mol Microbiol.., Mar. 1993, vol. 7, No. 6, pp. 933-936; Abstract Only.
Curtiss III, Roy et al., "Induction of Host Immune Responses Using Salmonella-Vectored Vaccines", Virulence Mechanisms of Bacterial Pathogens, 4th ed., Chapter 20, 2007, pp. 297-313.
Curtiss III, Roy et al., "*Salmonella enterica* Serovar Typhimurium Strains with Regulated Delayed Attenuation in Vivo", Infection and Immunity, Mar. 2009, pp. 1071-1082, vol. 77, No. 3.

(Continued)

*Primary Examiner* — Brian Gangle
(74) *Attorney, Agent, or Firm* — Timothy H. Van Dyke; Wolter Van Dyke; Davis, PLLC

(57) ABSTRACT

Disclosed herein are unique adjuvant compositions comprising an attenuated derivative of a self-destructing bacterial pathogen that undergoes lysis in vivo. In exemplary embodiments, the bacterial pathogen is a *Salmonella* spp. Also disclosed are methods for enhancing an immune response using the adjuvants disclosed herein.

13 Claims, 30 Drawing Sheets

(56)        References Cited

OTHER PUBLICATIONS

Curtiss III, Roy et al., "Nonrecombinant and Recomninant Avirulent Salmonella Live Vaccine For Poultry", Colonization Control of Human Bacterial Enteropathogens in Poultry, 1991, pp. 169-198.

Edwards, Robert A. et al., "Improved allelic exchange vectors and their use to analyze 987P fimbria gene expression", Gene, 1998, vol. 207, pp. 149-157.

Essers, Marieke A. G. et al., "IFNa activates dormant haematopietic stem cells in vivo", Nature, Apr. 16, 2009, vol. 458, pp. 904-908.

Galan, Jorge E. et al., "Cloning and characterization of the asd gene of *Salmonella typhimurium*: use in stable maintenance of recombinant plasmids in Salmonella vaccine strains", Gene, 1990, vol. 94, pp. 29-35.

Green, Michael R., "Molecular Cloning", A Laboratory Manual, 2012, vol. 1, Fourth Edition, 34 pages.

Gunn, Brownwyn M. et al., "Construction of Recombinant Attenuated *Salmonella enterica* Serovar Typhimurium Vaccine Vector Strains for Safety in Newborn and Infant Mice", Clinical and Vaccine Immunology, Mar. 2010, vol. 17, No. 3, pp. 354-362.

Herrera, Carmen M. et al., "Activation of PmrA inhibits LpxT-dependent phosphorylation of lipid A promoting resistance to antimicrobial peptides", Molecular Microbiology, 2010, vol. 76, No. 6, 1444-1460.

Juarez-Rodriguez, Maria Dolores et al, "Live Attenuated Salmonella Vaccines against *Mycobacterium tuberculosis* with Antigen Delivery via the Type III Secretion System", Infection and Immunity, Feb. 2012, vol. 80, No. 2, pp. 798-813.

Kang, Ho Young et al., "Transduction-Mediated Transfer of Unmarked Deletion and Point Mutations through Use of Counterselectable Suicide Vectors", Journal of Bacteriology, Jan. 2002, , vol. 184, No. 1 pp. 307-312.

Kong, Qingke et al., "Regulated Delayed Expression of rfaH in an Attenuated *Salmonella enterica* Serovar Typhimurium Vaccine Enhances Immunogenicity of Outer Membrane Proteins and a Heterologous Antigen" Infection and Immunity, Dec. 2009, vol. 77, No. 12, pp. 5572-5582.

Kong, Qingke et al., "Salmonella synthesizing 1-monophosphorylated LPS exhibits low endotoxic activity while retaining its immunogenicity", J Immunol., Jul. 1, 2011, vol. 187, No. 1, pp. 412-423.

Kong, Wei et al., "Turning self-destructing Salmonella into a universal DNA vaccine delivery platform", PNAS, Nov. 20, 2012, vol. 109, No. 47, pp. 19414-19419.

Kong, Qingke et al., "Regulated delayed expression of rfc enhances the immunogenicity and protective efficacy of a heterologous antigen delivered by live attenuated *Salmonella enterica* vaccines", Vaccine, Aug. 23, 2010, vol. 28, No. 37, pp. 6094-6103.

Kong, Qingke et al., "Phosphate Groups of Lipid A Are Essential for *Salmonella enterica* Serovar Typhimurium Virulence and Affect Innate and Adaptive Immunity", Infection and Immunity, Sep. 2012, vol. 80, No. 9, pp. 3215-3224.

Kong, Wei et al., "Regulated programmed lysis of recombinant Salmonella in host tissues to release protective antigens and confer biological containment", PNAS, Jul. 8, 2008, vol. 105, No. 27, pp. 9361-9366.

Laniewski, Pawel et al., "Analysis of Spleen-Induced Fimbria Production in Recombinant Attenuated *Salmonella enterica* Serovar Typhimurium Vaccine Strains", MBIO, Jul./Aug. 2017, vol. 8, Issue 4, 13 pages.

Lau, Nicole et al., "SopF, a phosphoinositide binding effector, promotes the stability of the nascent Salmonella-containing vacuole", PLOS Pathog., 2019, vol. 15, No. 7, 36 pages.

Lee, Francis K. et al., "ELISPOT: A New Approach to Studying the Dynamics of Virus-Immune System Interaction for Diagnosis and Monitoring of HIV Infection", AIDS Research and Human Retroviruses, 1989, vol. 5, No. 5, 7 pages.

Li, Yuhua et al., "A sopB Deletion Mutation Enhances the Immunogenicity and Protective Efficay of a Heterologous Antigen Delivered by Live Attenuated *Salmonella enterica* Vaccines", Infection and Immunity, Nov. 2008, p. 5238-5246 vol. 76, No. 11.

Liu, Qiong et al., "Outer membrane vesicles from flagellin-deficient *Salmonella enterica* serovar Typhimurium induce cross-reactive immunity and provide cross-protection against heterologous Salmonella challenge", Scientific Reports, 2016, vol. 6, No. 34776, 13 pages.

McCuskey, Robert S. et al., "Species Differences in Kupffer Cells and Endotoxin Sensitivity", Infection and Immunity, Jul. 1984, vol. 45, No. 1, pp. 278-280.

Nakayama, Koji et al., "Construction of an ASD+ expression-cloning vector: Stable maintenance and high level expression of cloned genes in a Salmonella vaccine strain", Nature Biology, 1988, vol. 6, pp. 693-697.

O'Callaghan, David et al., "Characterization of Aromatic-and Purine-Dependent *Salmonella typhimurium*: Attenuation, Persistence, and Ability to Induce Protective Immunity in BALB/c Mice", Infection and Immunity, Feb. 1988, vol. 56, No. 2, pp. 419-423.

Ohlson, Maikke B. et al., "Structure and function of SifA indicate that interactions with SKIP, Ssej, and RhoA family GTPases induce endosomal tubulation", Cell Host Microbe., Nov. 13, 2008, vol. 4, No. 5, pp. 434-446.

Ottenhoff, Tom H. M. et al., "First in humans: A new molecularly defined vaccine shows excellent safety and strong induction of long-lives *Mycobacterium tuberculosis*-specific TH1-cell like responses", Human Vaccines, 2010, 10 pages.

Park, Beom Seok et al., "The structural basis of lipopolysaccharide recognition by the TLR4-MD-2 complex", Nature Letters, Apr. 30, 2009, vol. 458, 6 pages.

Pizarro-Cerdá, Javier et al., "The bacterial signal molecule, ppGpp, regulates Salmonella virulence gene expression", Molecular Microbiology, 2004, vol. 52, No. 6, pp. 1827-1844.

Quandt, Jurgen et al., "Versatile suicide vectors which allow direct selection for gene replacement in Gram-negative bacteria", Gene, 1993, vol. 127, pp. 15-21.

Roland, Kenneth et al., Construction and evaluation of a Acya Acrp *Salmonella typhimurium* Strain Expressing Avian Pathogenic *Escherichia coli* 078 LPS as a Vaccine to Prevent Airsacculitis in Chickens, Avain Diseases, 1999, vol. 43, pp. 429-441.

Schmieger, Horst, "Phage P22-Mutants with Increased or Decreased Transduction Abilities", Molec. Gen. Genet., 1972, vol. 119, pp. 75-88.

Schmieger, Horst et al., "Altered Cotransduction Frequencies Exhibited by HT-Mutants of Salmonella-Phage P22", Molec. Gen. Genet., 1976, vol. 143, pp. 307-309.

Skjøt, Rikke Louise Vinther et al., "Comparative Evaluation of Low-Molecular-Mass Proteins from *Mycobacterium tuberculosis* Identifies Members of the ESAT-6 Family as Immunodominant T-Cell Antigens", Infection and Immunity, 2000, vol. 68, No. 1, pp. 214-220.

Sørensen, Anne L. et al., "Purification and Characterization of a Low-Molecular-Mass T-Cell Antigen Secreted by *Mycobacterium tuberculosis*", Infection and Immunity, May 1995, vol. 63, No. 5, pp. 1710-1717.

Stevenson, Gordon et al., "Organization of the Escherichia coli K-12 Gene Cluster Responsible for Production of the Extracellular Polysaccharide Colanic Acid", Journal of Bacteriology, Aug. 1996, vol. 178, No. 16, pp. 4885-4893.

Takizawa, Hitoshi et al., "Demand-adapted regulation of early hematopoiesis in infection and inflammation", Blood, Mar. 29, 2012 z vol. 119, No. 13, pp. 2991-3002.

Torok, Istvan et al., "Accumulation of ppGpp in a relA Mutant of *Escherichia coli* during Amino Acid Starvation", The Journal of Biological Chemistry, 1980, vol. 255, No. 9, issue of May 10, pp. 3838-3840.

Trent, M. Stephen et al., "An Inner Membrane Enzyme in Salmonella and *Escherichia coli* That Transfers 4-Amino-4-deoxy-L-arabinose to Lipid A", the Journal of Biological Chemistry, 2001, vol. 276, No. 46, Issue of Nov. 16, pp. 43122-43131.

Vander Byl, Carolyn et al., "Sequence of the Genome of Salmonella Bacteriophage P22", Journal of Bacteriology, Nov. 2000, vol. 182, No. 22, pp. 6472-6481.

* cited by examiner

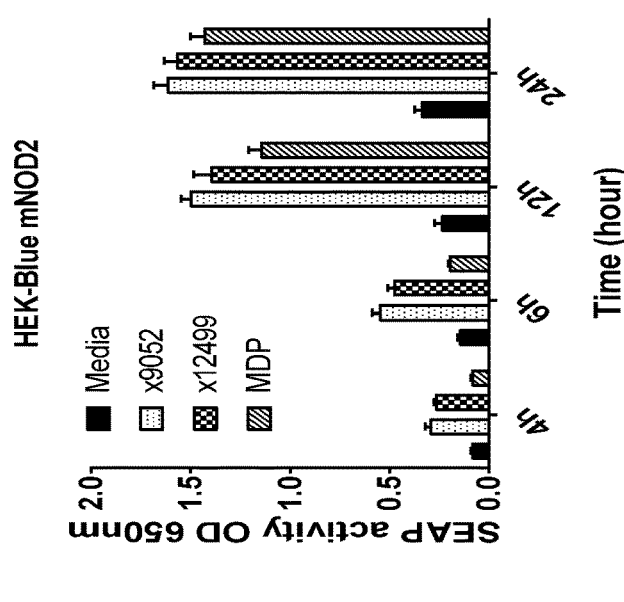
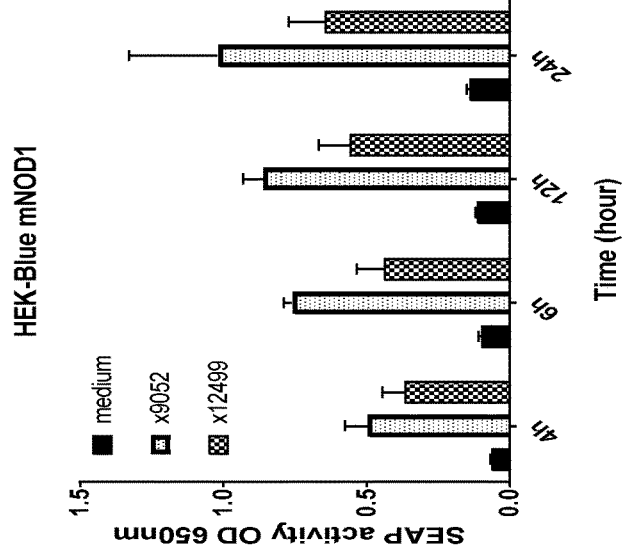
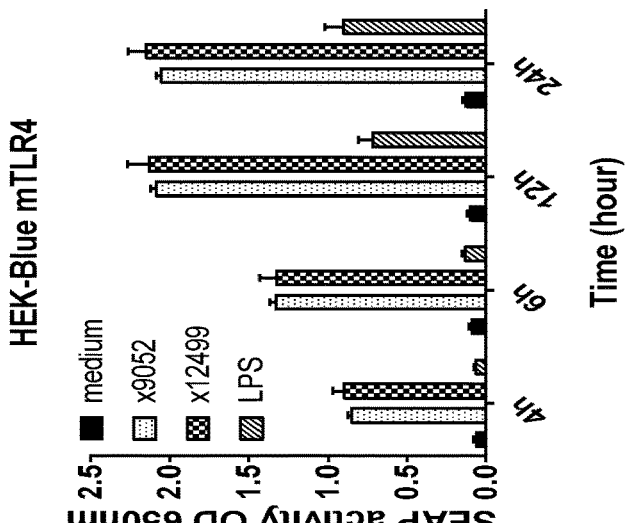
Figure 2

Swimming motility phenotypes of different S. Typhimurium mutant strains

Figure 9: *M. tuberculosis* H37Rv titers in spleens of mice vaccinated with BCG with and without inoculation with ENIIRA strain χ12499 or with χ12499 alone
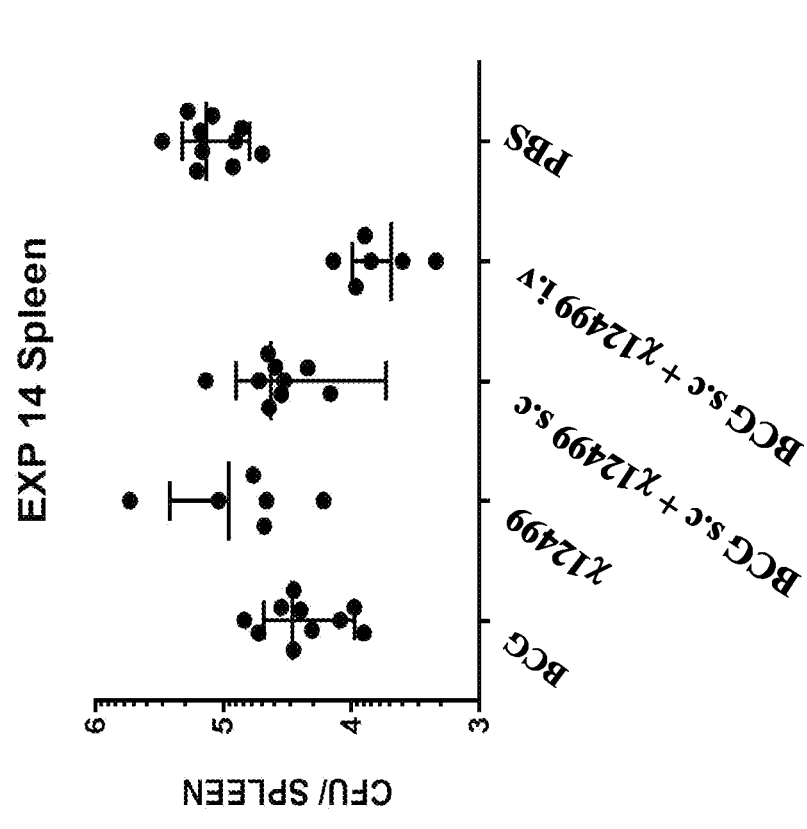

Figure 10: *M. tuberculosis* H37Rv titers in spleens of mice vaccinated with BCG alone or with PIESV χ12068(pYA4891) or with ENIIRA strains χ12517 or χ12518
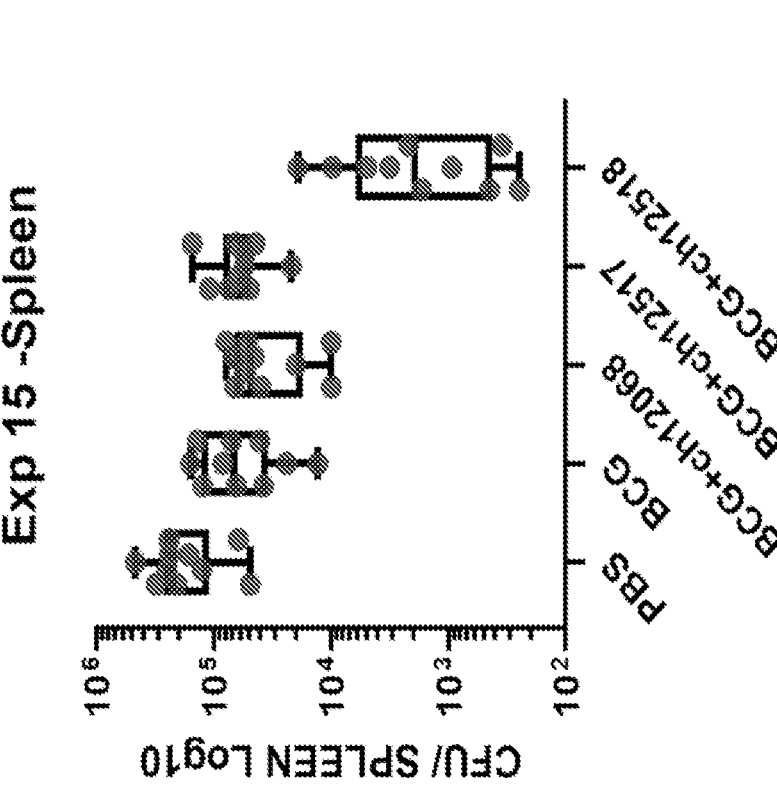

**Figure 11: Titers of *M. tuberculosis* H37Rv CFU per g of lung in mice vaccinated with BCG and/or χ12068(pYA4891) with or without inoculation with EIINRA χ12518**
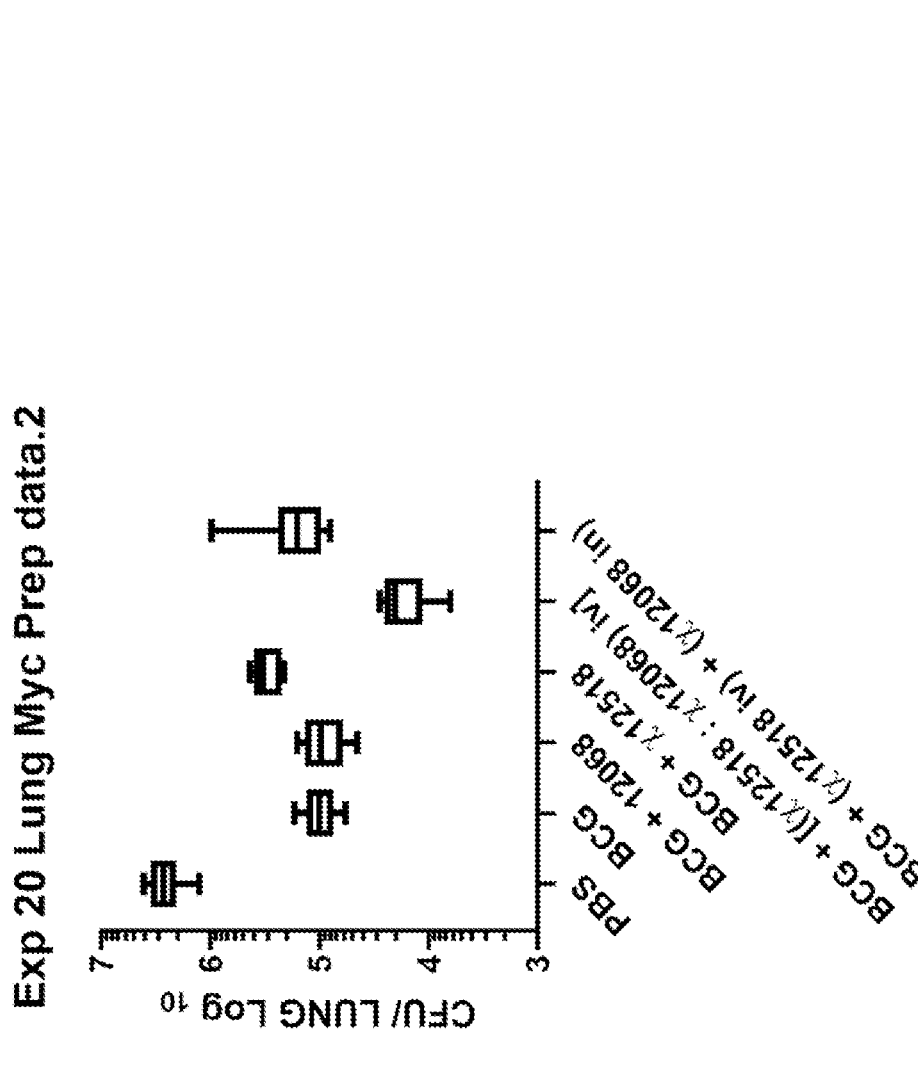

Spleen ~ Total T Cell expansion

| | Sample Name | Subset Name | Count |
|---|---|---|---|
| ▨ | Spleen_Tube_009.fcs | CD3, SSC-A subset | 16574 |
| ▨ | Spleen_Tube_010.fcs | CD3, SSC-A subset | 11185 |
| ▨ | Spleen_Tube_006.fcs | CD3, SSC-A subset | 12574 |
| ▨ | Spleen_Tube_007.fcs | CD3, SSC-A subset | 12053 |
| ▨ | Spleen_Tube_008.fcs | CD3, SSC-A subset | 16663 |

FIG. 12B

Figure 13. Attenuated Adjuvant *Salmonella* (AAS) has higher abilities to activate TLR5 and TLR4.

HEK-Blue cells at $10^5$ cells/ml were mixed with bacterial cells at a MOI of 10 in a volume of 200 µl in 96 well plates. Both χ12517 and χ12518 have mutations *ΔfliC180 ΔpagP::P*<sub>lpp</sub> *lpxE ΔpagL7 ΔlpxR9*. Flagellin and LPS, 100 ng.

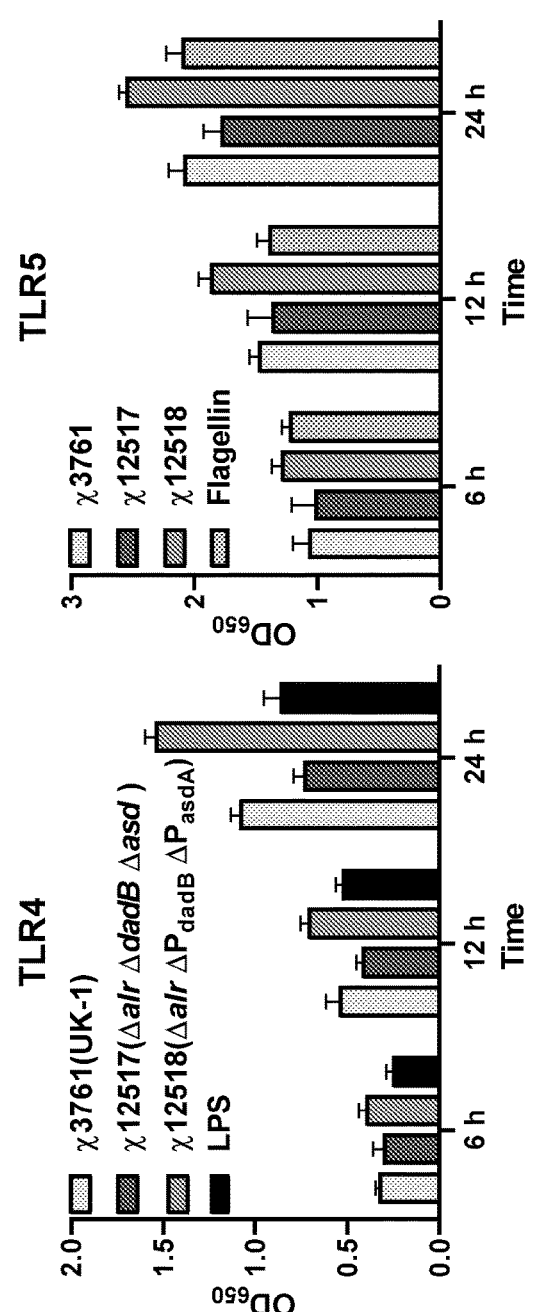

χ12517: *Δalr-3 ΔdadB4 ΔasdA33 ΔfliC180 ΔpagP81::P*<sub>lpp</sub> *lpxE ΔpagL7 ΔlpxR9*

χ12518: *ΔP*<sub>asdA55</sub>*::TT araC P*<sub>BAD</sub> *asd Δalr-3 ΔP*<sub>dadB66</sub>*::TT araC P*<sub>BAD</sub> *dadB ΔfliC180 ΔpagP81::P*<sub>lpp</sub> *lpxE ΔpagL7 ΔlpxR9*

Figure 14. Exp. 20. Ability of Attenuated Adjuvant *Salmonella* (AAS) to enhance protection of mice against *M. tuberculosis* H37Rv challenge
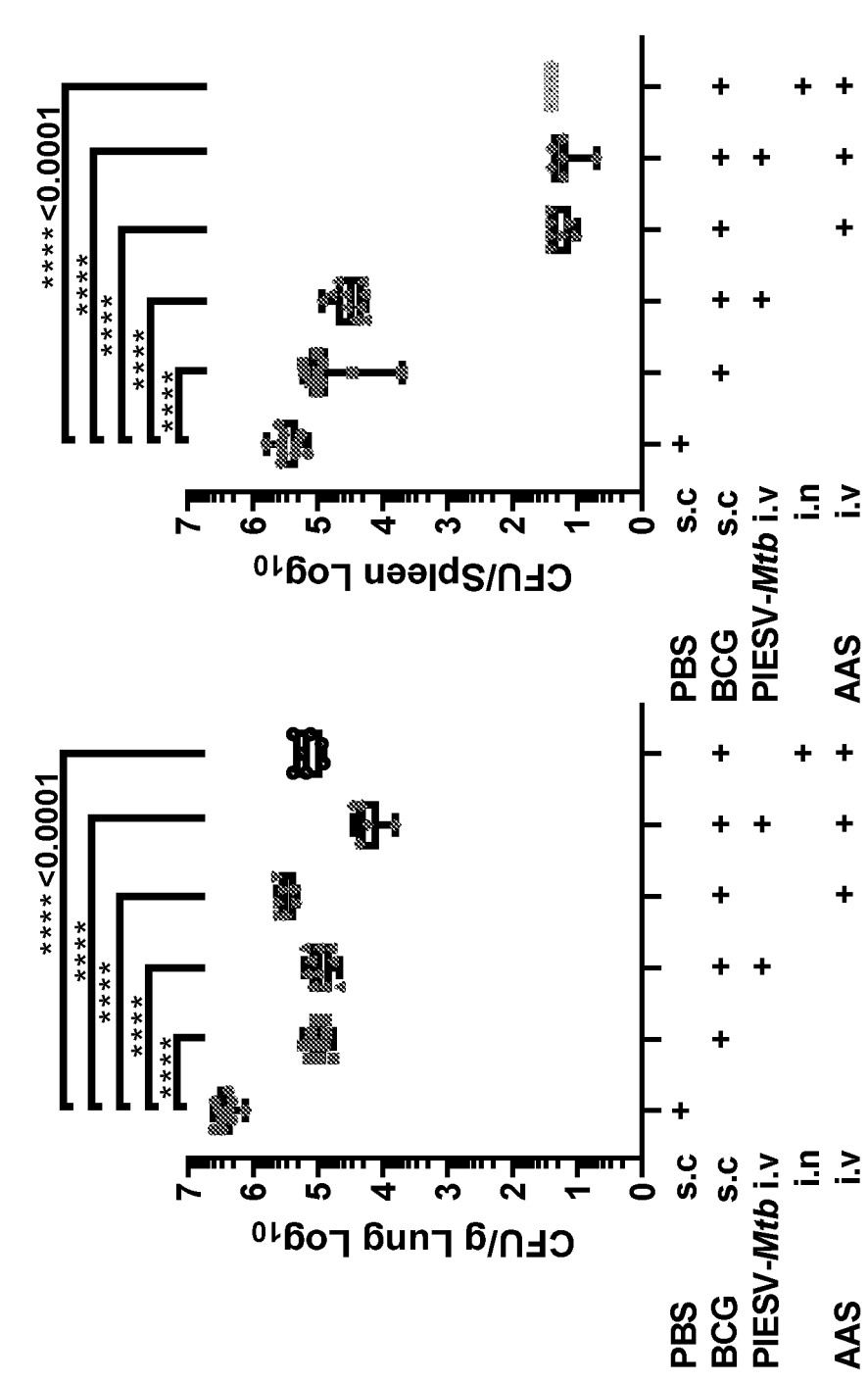

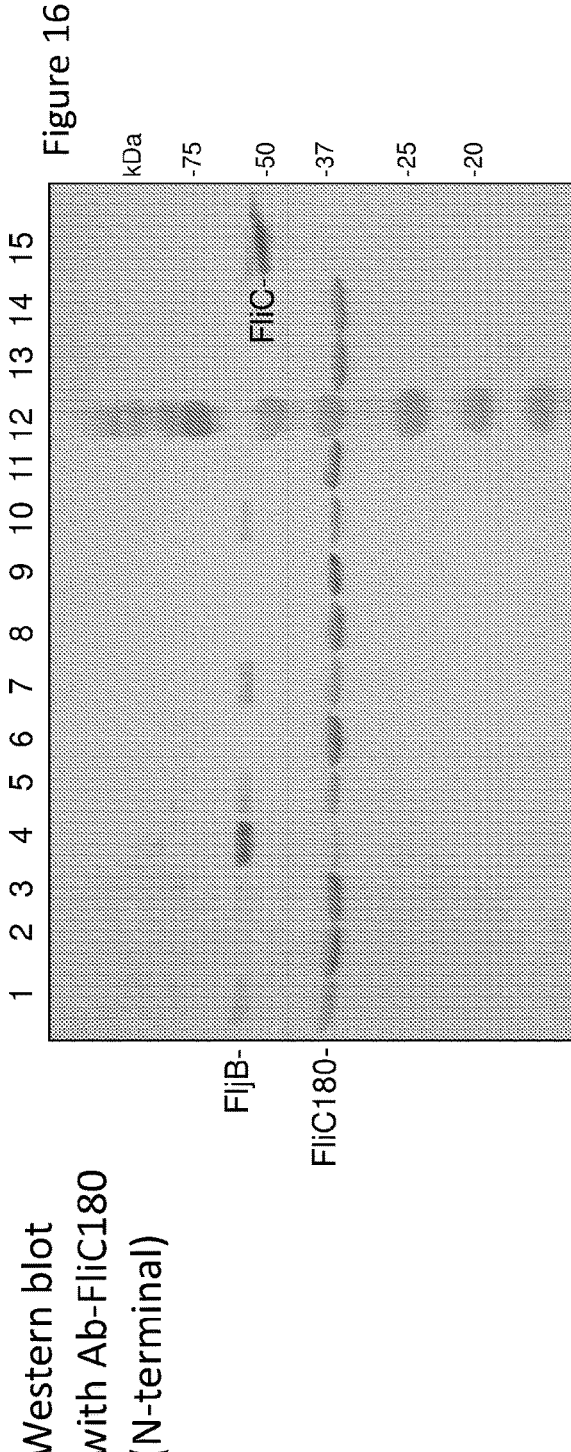

Figure 16

Western blot
with Ab-FliC180
(N-terminal)

1. χ12518, ΔP$_{asdA55}$::TT araC P$_{araBAD}$ asd Δalr-3 ΔP$_{dadB66}$::TT araC P$_{araBAD}$ dadB ΔfliC180 ΔpagP81::P$_{lpp}$ lpxE ΔpagL7 ΔlpxR9
2. χ12547, ΔP$_{asdA55}$::TT araC P$_{araBAD}$ asd Δalr-3 ΔP$_{dadB66}$::TT araC P$_{araBAD}$ dadB ΔfliC180 Δ(hin-fljBA)-219
3. χ12548, ΔP$_{asdA55}$::TT araC P$_{araBAD}$ asd Δalr-3 ΔP$_{dadB66}$::TT araC P$_{araBAD}$ dadB ΔfliC180 ΔpagP81::P$_{lpp}$ lpxE ΔpagL7 ΔlpxR9 Δ(hin-fljBA)-219
4. χ12549, ΔP$_{asdA55}$::TT araC P$_{araBAD}$ asd Δalr-3 ΔP$_{dadB66}$::TT araC P$_{araBAD}$ dadB ΔfliC180 ΔwaaL46
5. χ12570, ΔP$_{asdA55}$::TT araC P$_{araBAD}$ asd Δalr-3 ΔP$_{dadB66}$::TT araC P$_{araBAD}$ dadB ΔfliC180 ΔpagP81::P$_{lpp}$ lpxE ΔpagL7 ΔlpxR9 ΔarnT6
6. χ12571, ΔP$_{asdA55}$::TT araC P$_{araBAD}$ asd Δalr-3 ΔP$_{dadB66}$::TT araC P$_{araBAD}$ dadB ΔfliC180 ΔpagP81::P$_{lpp}$ lpxE ΔpagL7 ΔlpxR9 Δ(hin-fljBA)-219 ΔarnT6
7. χ12583, ΔP$_{asdA55}$::TT araC P$_{araBAD}$ asd Δalr-3 ΔP$_{dadB66}$::TT araC P$_{araBAD}$ dadB ΔfliC180 ΔpagP81::P$_{lpp}$ lpxE ΔpagL7 ΔlpxR9 ΔeptA4
8. χ12584, ΔP$_{asdA55}$::TT araC P$_{araBAD}$ asd Δalr-3 ΔP$_{dadB66}$::TT araC P$_{araBAD}$ dadB ΔfliC180 ΔpagP81::P$_{lpp}$ lpxE ΔpagL7 ΔlpxR9 Δ(hin-fljBA)-219 ΔeptA4
9. χ12585, ΔP$_{asdA55}$::TT araC P$_{araBAD}$ asd Δalr-3 ΔP$_{dadB66}$::TT araC P$_{araBAD}$ dadB ΔfliC180 ΔpagP81::P$_{lpp}$ lpxE ΔpagL7 ΔlpxR9 Δ(hin-fljBA)-219 ΔarnT6 ΔeptA4
10. χ12586, ΔP$_{asdA55}$::TT araC P$_{araBAD}$ asd Δalr-3 ΔP$_{dadB66}$::TT araC P$_{araBAD}$ dadB ΔfliC180 ΔpagP81::P$_{lpp}$ lpxE ΔpagL7 ΔlpxR9 Δ(hin-fljBA)-219 ΔpagP8
11. χ12603, ΔP$_{asdA55}$::TT araC P$_{araBAD}$ asd Δalr-3 ΔP$_{dadB66}$::TT araC P$_{araBAD}$ dadB ΔfliC180 Δ(hin-fljBA)-219 ΔpagP8
12. PSMW
13. χ12604, ΔP$_{asdA55}$::TT araC P$_{araBAD}$ asd Δalr-3 ΔP$_{dadB66}$::TT araC P$_{araBAD}$ dadB ΔfliC180 ΔpagP8 ΔpagL7 ΔlpxR9 Δ(hin-fljBA)-219
14. χ12605, ΔP$_{asdA55}$::TT araC P$_{araBAD}$ asd Δalr-3 ΔP$_{dadB66}$::TT araC P$_{araBAD}$ dadB ΔfliC180 Δ(hin-fljBA)-219 ΔpagP8 ΔpagL7
15. χ3761, wild-type UK-1

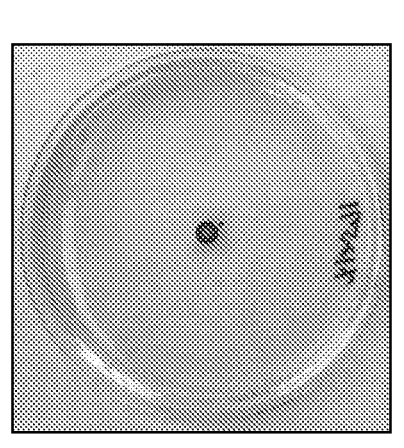
Motility plate of Δ(*hin-fljBA*)-219 strains (also with Δ*fliC180*) showing a 5 mm spot where they were originally spotted.
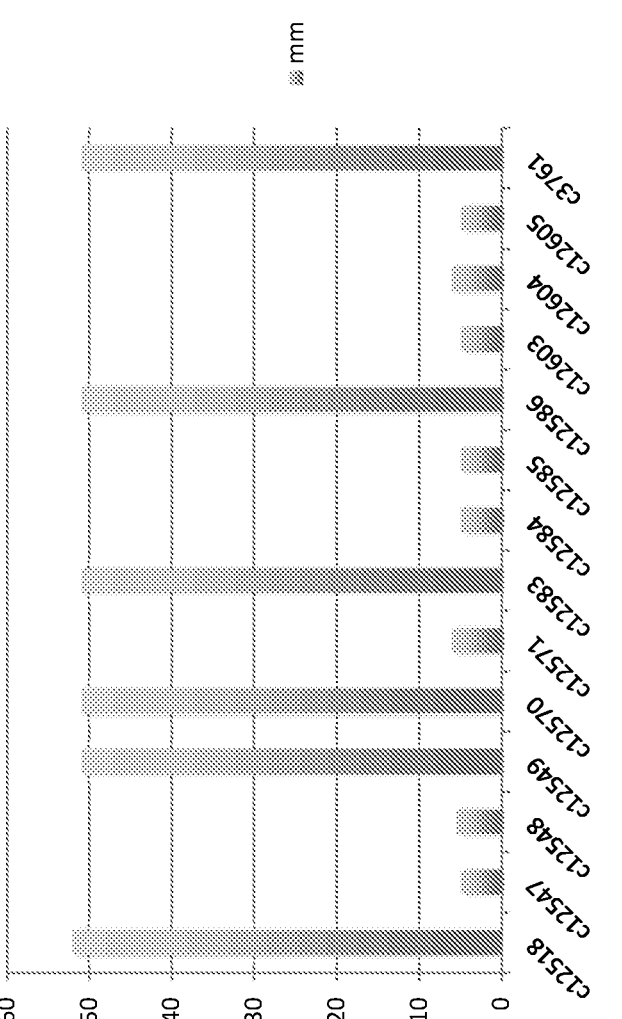
Motility
Figure 17

TLR-4 @ 8h

TLR5 activity
Supernatant vs Bacteria

S: Supernatant
B: Bacteria

χ3761
χ9026
χ9028
χ12612
χ12620–
χ12620+
χ12621
χ12626
χ12641
Media Control

Supernatant dilution: 1:100

Bacterial MOI: 1:10

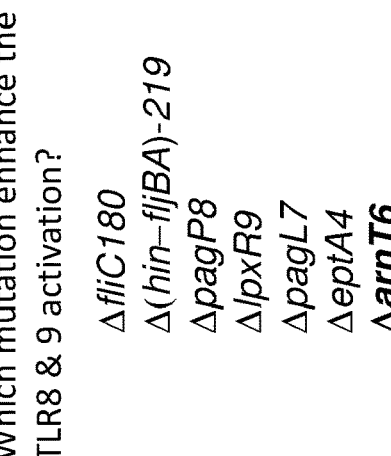
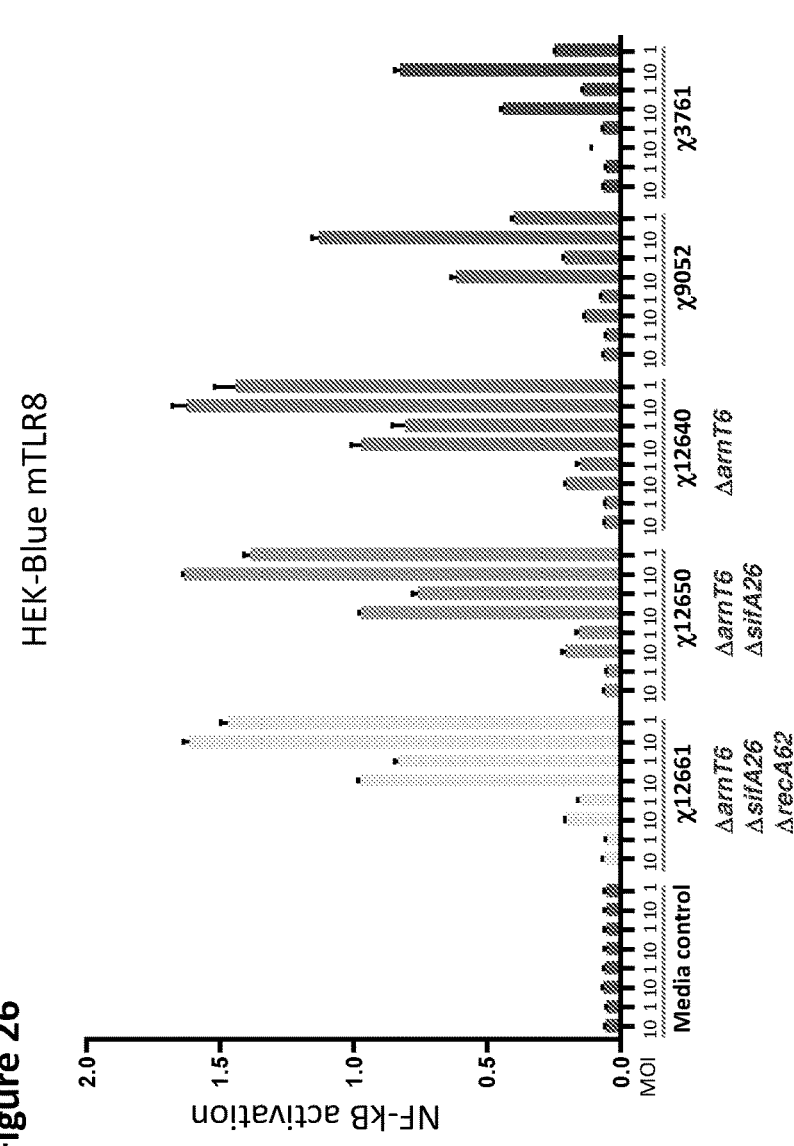
Figure 26

LIVE SELF-DESTRUCTING BACTERIAL ADJUVANTS TO ENHANCE INDUCTION OF IMMUNITY

GOVERNMENT SUPPORT

This invention was made with government support under 2017-67017-26179 awarded by United States Department of Agriculture, NIFA and AI056289 awarded by The National Institutes of Health. The government has certain rights in the invention.

BACKGROUND

Multicellular organisms have developed two general systems of immunity to infectious agents. The two systems are innate or natural immunity (also known as "innate immunity") and adaptive (acquired) or specific immunity. The major difference between the two systems is the mechanism by which they recognize infectious agents.

The innate immune system uses a set of germline-encoded receptors for the recognition of conserved molecular patterns present in microorganisms. These molecular patterns occur in certain constituents of microorganisms including: lipopolysaccharides, peptidoglycans, lipoteichoic acids, phosphatidyl cholines, bacteria-specific proteins, including lipoproteins, bacterial DNAs, viral, bacterial and parasite single and double-stranded RNAs, unmethylated CpG-DNAs, mannans and a variety of other bacterial and fungal cell wall components. Such molecular patterns can also occur in other molecules such as plant alkaloids. These targets of innate immune recognition are called Pathogen Associated Molecular Patterns (PAMPs) since they are produced by microorganisms and not by the infected host organism. (Janeway et al. (1989) Cold Spring Harb. Symp. Quant. Biol. 54:1-13; Medzhitov et al. (1997) Curr. Opin. Immunol. 94:4-9). These receptors are also referred to as MAMPs for Microbial-Associated Molecular Patterns since they exist in non-pathogenic commensal microbes as well as in pathogenic microbes.

The receptors of the innate immune system that recognize PAMPs are called Pattern Recognition Receptors (PRRs). (Janeway et al. (1989) Cold Spring Harb. Symp. Quant. Biol. 54:1-13; Medzhitov et al. (1997) Curr. Opin. Immunol. 94:4-9). These receptors vary in structure and belong to several different protein families. Some of these receptors recognize PAMPs directly (e.g., CD14, DEC205, collectins), while others (e.g., complement receptors) recognize the products generated by PAMP recognition. Members of these receptor families can, generally, be divided into three types: 1) humoral receptors circulating in the plasma; 2) endocytic receptors expressed on immune-cell surfaces, and 3) signaling receptors that can be expressed either on the cell surface or intracellularly. (Medzhitov et al. (1997) Curr. Opin. Immunol. 94:4-9; Fearon et al. (1996) Science 272:50-3).

Cellular PRRs are expressed on effector cells of the innate immune system, including cells that function as professional antigen-presenting cells (APC) in adaptive immunity. Such effector cells include, but are not limited to, macrophages, dendritic cells, B lymphocytes and surface epithelia. This expression profile allows PRRs to directly induce innate effector mechanisms, and also to alert the host organism to the presence of infectious agents by inducing the expression of a set of endogenous signals, such as inflammatory cytokines and chemokines, as discussed below. This latter function allows efficient mobilization of effector forces to combat the invaders.

In contrast, the adaptive immune system, which is found only in vertebrates, uses two types of antigen receptors that are generated by somatic mechanisms during the development of each individual organism. The two types of antigen receptors are the T-cell receptor (TCR) and the immunoglobulin receptor (IgR), which are expressed on two specialized cell types, T-lymphocytes and B-lymphocytes, respectively. The specificities of these antigen receptors are generated at random during the maturation of lymphocytes by the processes of somatic gene rearrangement, random pairing of receptor subunits, and by a template-independent addition of nucleotides to the coding regions during the rearrangement.

Recent studies have demonstrated that the innate immune system plays a crucial role in the control of initiation of the adaptive immune response and in the induction of appropriate cell effector responses. (Fearon et al. (1996) Science 272:50-3; Medzhitov et al. (1997) Cell 91:295-8). Indeed, it is now well established that the activation of naive T-lymphocytes requires two distinct signals: one is a specific antigenic peptide recognized by the TCR, and the other is the so called co-stimulatory signal, B7, which is expressed on APCs and recognized by the CD28 molecule expressed on T-cells. (Lenschow et al. (1996) Annu. Rev. Immunol. 14:233-58). Activation of naive $CD4^+$ T-lymphocytes requires that both signals, the specific antigen and the B7 molecule, are expressed on the same APC. If a naive CD4 T-cell recognizes the antigen in the absence of the B7 signal, the T-cell will die by apoptosis. Expression of B7 molecules on APCs, therefore, controls whether or not the naive CD4 T-lymphocytes will be activated. Since CD4 T-cells control the activation of CD8 T-cells for cytotoxic functions, and the activation of B-cells for antibody production, the expression of B7 molecules determines whether or not an adaptive immune response will be activated.

Recent studies have also demonstrated that the innate immune system plays a crucial role in the control of B7 expression. (Fearon et al. (1996) Science 272:50-3; Medzhitov et al. (1997) Cell 91:295-8). As mentioned earlier, innate immune recognition is mediated by PRRs that recognize PAMPs. Recognition of PAMPs by PRRs results in the activation of signaling pathways that control the expression of a variety of inducible immune response genes, including the genes that encode signals necessary for the activation of lymphocytes, such as B7, cytokines and chemokines. (Medzhitov et al. (1997) Cell 91:295-8; Medzhitov et al. (1997) Nature 388:394-397). Induction of B7 expression by PRR upon recognition of PAMPs thus accounts for self/nonself discrimination and ensures that only T-cells specific for microorganism-derived antigens are normally activated. This mechanism normally prevents activation of autoreactive lymphocytes specific for self-antigens.

Receptors of the innate immune system that control the expression of B7 molecules and cytokines have recently been identified. (Medzhitov et al. (1997) Nature 388:394-397; Rock et al. (1998) Proc. Natl. Acad. Sci. USA, 95:588-93). These receptors belong to the family of Toll-like receptors (TLRs), so called because they are homologous to the *Drosophila* Toll protein which is involved both in dorsoventral patterning in *Drosophila* embryos and in the immune response in adult flies. (Lemaitre et al. (1996) Cell 86:973-83). In mammalian organisms, such TLRs have been shown to recognize PAMPs such as the bacterial products LPS, peptidoglycan, and lipoprotein. (Schwandner et al. (1999) J. Biol. Chem. 274:17406-9; Yoshimura et al. (1999) J. Immunol. 163:1-5; Aliprantis et al. (1999) Science 285:736-9).

Vaccines have traditionally been used as a means to protect against disease caused by infectious agents. However, with the advancement of vaccine technology, vaccines have been used in additional applications that include, but are not limited to, control of mammalian fertility, modulation of hormone action, and prevention or treatment of tumors.

The primary purpose of vaccines used to protect against a disease is to induce immunological memory to a particular microorganism or antigen. More generally, vaccines are needed to induce an immune response to specific antigens, whether they belong to a microorganism or are expressed by tumor cells or other diseased or abnormal cells. Division and differentiation of B- and T-lymphocytes that have surface receptors specific for the antigen generate both specificity and memory.

In order for a vaccine to induce a protective immune response, it must fulfill the following requirements: 1) it must include the specific antigen(s) or fragment(s) thereof that will be the target of protective immunity following vaccination; 2) it must present such antigens in a form that can be recognized by the immune system, e.g., a form resistant to degradation prior to immune recognition; or it must deliver a DNA vaccine encoding such antigens that will be synthesized by the vaccinated host, stable against degradation and be presentable to be recognized by the immune system and 3) it must activate APCs to present the antigen to CD4$^+$ T-cells, which in turn induce B-cell differentiation and other immune effector functions as well as to CD8$^+$ and CD17$^+$ cells to activate cellular immunity.

Conventional vaccines contain suspensions of attenuated or killed microorganisms, such as viruses or bacteria, incapable of inducing severe infection by themselves, but capable of counteracting the unmodified (or virulent) species when inoculated into a host. Usage of the term has now been extended to include essentially any preparation intended for active immunologic prophylaxis (e.g., preparations of killed microbes of virulent strains or living microbes of attenuated (variant or mutant) strains; microbial, fungal, plant, protozoan, or metazoan derivatives or products; synthetic vaccines). Examples of vaccines include, but are not limited to, cowpox virus for inoculating against smallpox, tetanus toxoid to prevent tetanus, whole-inactivated bacteria to prevent whooping cough (pertussis), polysaccharide subunits to prevent streptococcal pneumonia, and recombinant proteins to prevent hepatitis B.

Although attenuated vaccines are usually immunogenic, their use has been limited because their efficacy generally requires specific, detailed knowledge of the molecular determinants of virulence. Moreover, the use of attenuated pathogens as vaccines is associated with a variety of risk factors that may compromise their safety for individuals to be vaccinated. Even more troublesome is the general experience since the initial attenuation of pathogens as vaccines by Pasteur is that as one introduces attenuating mutations there is a concomitant decrease in immunogenicity. This is because attenuating mutations decrease the ability of the attenuated vaccine to colonize the vaccinated host or to replicate and persist in that host in lymphoid tissues needed to induce the needed immune responses necessary to confer protective immunity.

The problem with synthetic vaccines (subunit, killed/inactivated pathogens, etc.), on the other hand, is that while they are generally safe they are often non-immunogenic or non-protective. This is because the immunogenic components are limited by the amount introduced in the vaccine at the time of vaccination and these components might be degraded and not persist for a long enough period of time to induce effective immune responses.

Because of these limitations in immunogenicity of many synthetic and attenuated vaccines, it is advantageous to augment that immunity by the co-administration of adjuvants with the vaccine at the time of vaccination. Adjuvants act in a variety of ways, such as by prolonging the stability and presence of the vaccine in host tissues or my stimulating the host immune system to produce cytokines and chemokines to recruit cells of the immune system to the site of vaccination or to stimulate components of the innate immune system to augment vaccine recognition and enhancement of induced immune responses. Unfortunately, there are very few adjuvants used with human vaccines due to safety concerns and the need to validate safety and efficacy with a particular vaccine in clinical trials. Consequently, vaccines are often administered without adjuvants or use alum that is safe but of limited effectiveness. More recently, mono-phosphoryl lipid A (MPLA) has been developed as a safe adjuvant to recruit innate immunity via interaction with TLR4 in a non-inflammatory manner.

An adjuvant is defined as any substance that increases the immunogenicity of admixed antigens. Although certain chemicals are often considered to be adjuvants, they are in effect akin to carriers and are likely to act by stabilizing antigens and/or promoting their interaction with antigen-presenting cells. The best adjuvants are those that mimic the ability of microorganisms to activate the innate immune system. Pure antigens do not induce an immune response because they fail to induce the costimulatory signal (e.g., B7.1 or B7.2) necessary for activation of lymphocytes. Thus, a key mechanism of adjuvant activity has been attributed to the induction of costimulatory signals by microbial, or microbial-like, constituents carrying PAMPs that are routine constituents of adjuvants. (Janeway et al. (1989) Cold Spring Harb. Symp. Quant. Biol., 54:1-13). As discussed above, the recognition of these PAMPs by PRRs induces the signals necessary for lymphocyte activation (such as B7) and differentiation (effector cytokines). Adjuvants currently typically used for vaccines in humans include Alum and mono-phosphoryl lipid A (MPLA).

Adjuvants are often used in molar excess of antigens and thus can trigger an innate immune response in many cells that do not come in contact with the target antigen. This non-specific induction of the innate immune system to produce the signals that are required for activation of an adaptive immune response can lead to an excessive inflammatory response that renders many of the most potent adjuvants clinically unsuitable.

BRIEF DESCRIPTION OF THE DRAWINGS

FIG. 2. Induction of TLR4, NOD1 and NOD2 signaling by *Salmonella* strains ($\chi$9052 and $\chi$12499) on HEK-Blue-mTLR4/mNOD1/mNOD2 cell lines. HEK-Blue cell lines, expressing mTLR4, mNOD1 or mNOD2, were stimulated with $\chi$9052 and $\chi$12499. TLR/NOD activation was measured by SEAP activity after incubation of HEK-Blue-mTLR4 (A), HEK-Blue-mNOD1 (B) or HEK-Blue-mNOD2 (C) cells with $\chi$9052 and $\chi$12499. MDP (100 ng/ml) or LPS (100 ng/ml) were used as positive controls. $\chi$9052 and $\times$12499 were grown in LB broth with D-alanine+

DAP+arabinose, sedimented at room temperature, washed with BSG and suspended in tissue culture medium. MDP—muramyl dipeptide FIG. 3. Survival of χ12517 and χ12518 after inoculation into non-permissive growth conditions. X12517 and χ12518 were grown in unpurple broth with DAP+D-alanine or unpurple broth with arabinose up to OD 0.9 bacterial cells were harvested and resuspended with PBS to desire concentration. Diluted bacteria were inoculated in un-purple broth for the lysis study. In every hour culture were plated on LB agar plates with DAP+D-alanine or LB agar plates with only arabinose and bacteria were counted FIG. 4. Swimming motility phenotypes of different S. *Typhimurium* mutant strains. Bacterial suspension was spotted onto the middle of the supplemented LB plates with 0.3% agar and incubated at 37° C. for 7 h. The diameter of the colonies was measured in centimeters.

Figure 5:
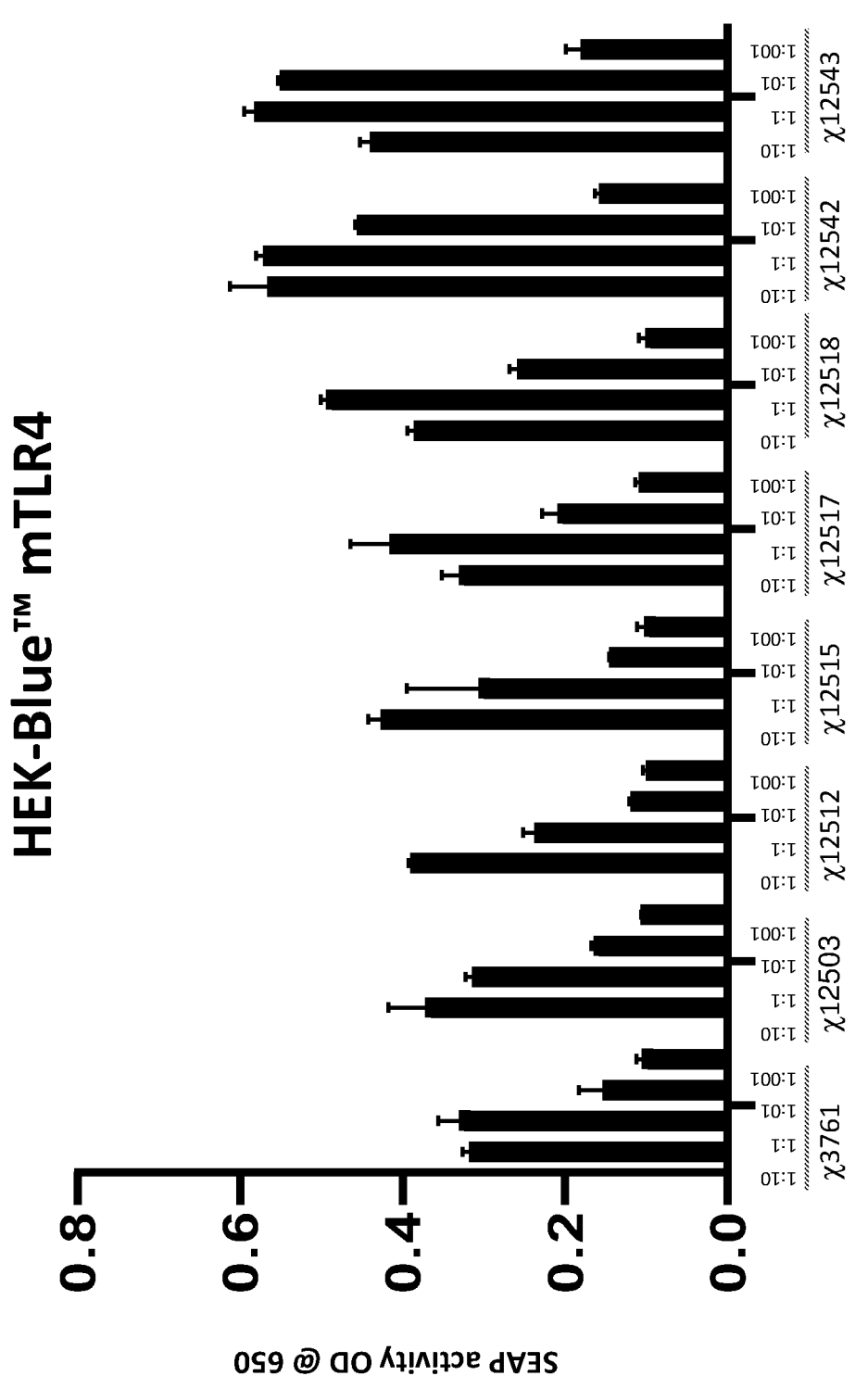

FIG. 5. Activation of TLR4 displayed on HEK cells by different S. *Typhimurium* mutant strains FIG. 6. Activation of TLR5 displayed on HEK cells by different S. *Typhimurium* mutant strains. HEK-Blue™ mTLR5 cells were stimulated with various *Salmonella* strains at different MOI of 10 or 1 or 0.01 or 0.001. After 24 h incubation, NF-kB-induced SEAP were determined by reading the OD at 650 nm. The response ratio was calculated by dividing the OD at 650 nm for the treated cells by the OD at 650 nm for the untreated cells.

Figure 7:
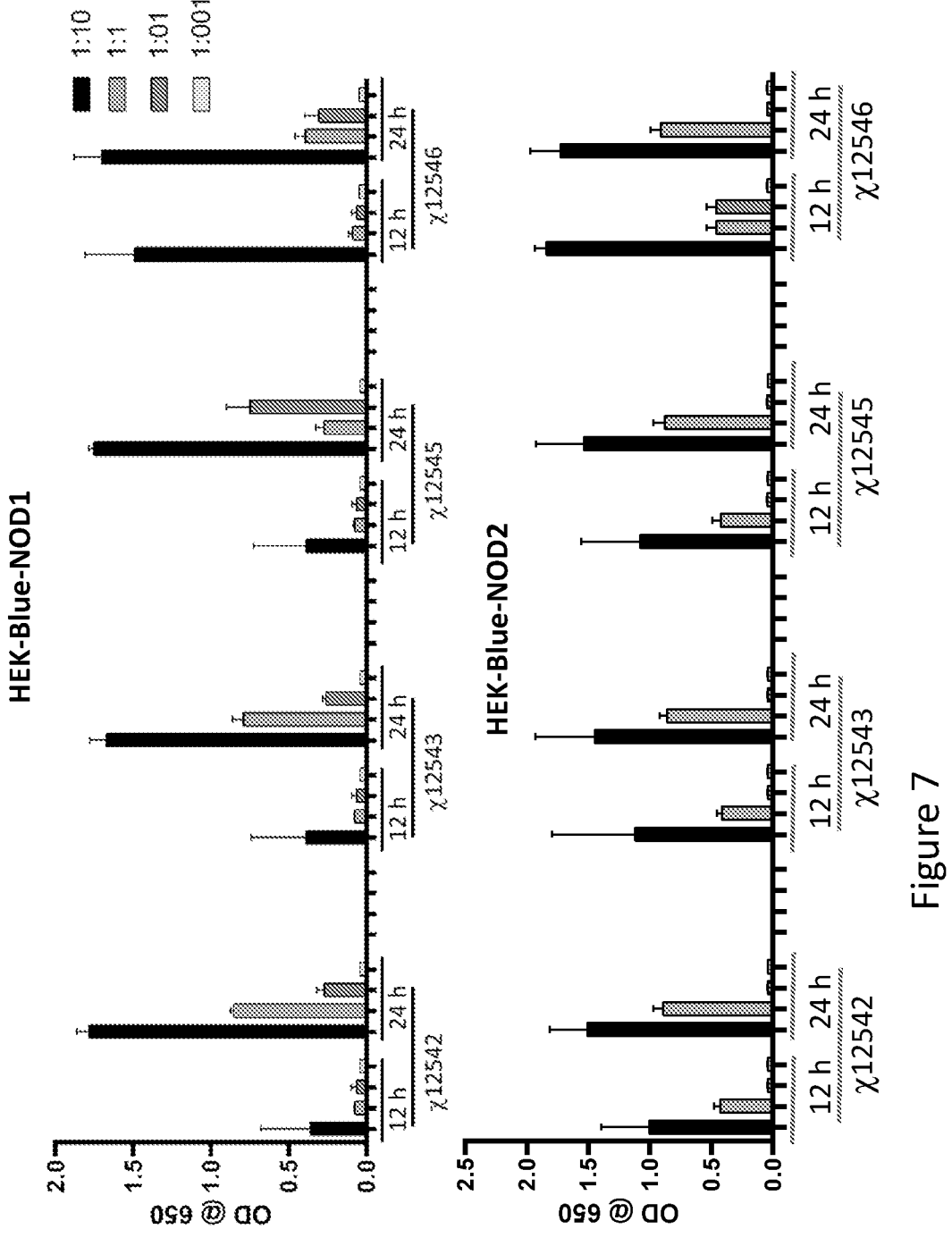
Figure 8:
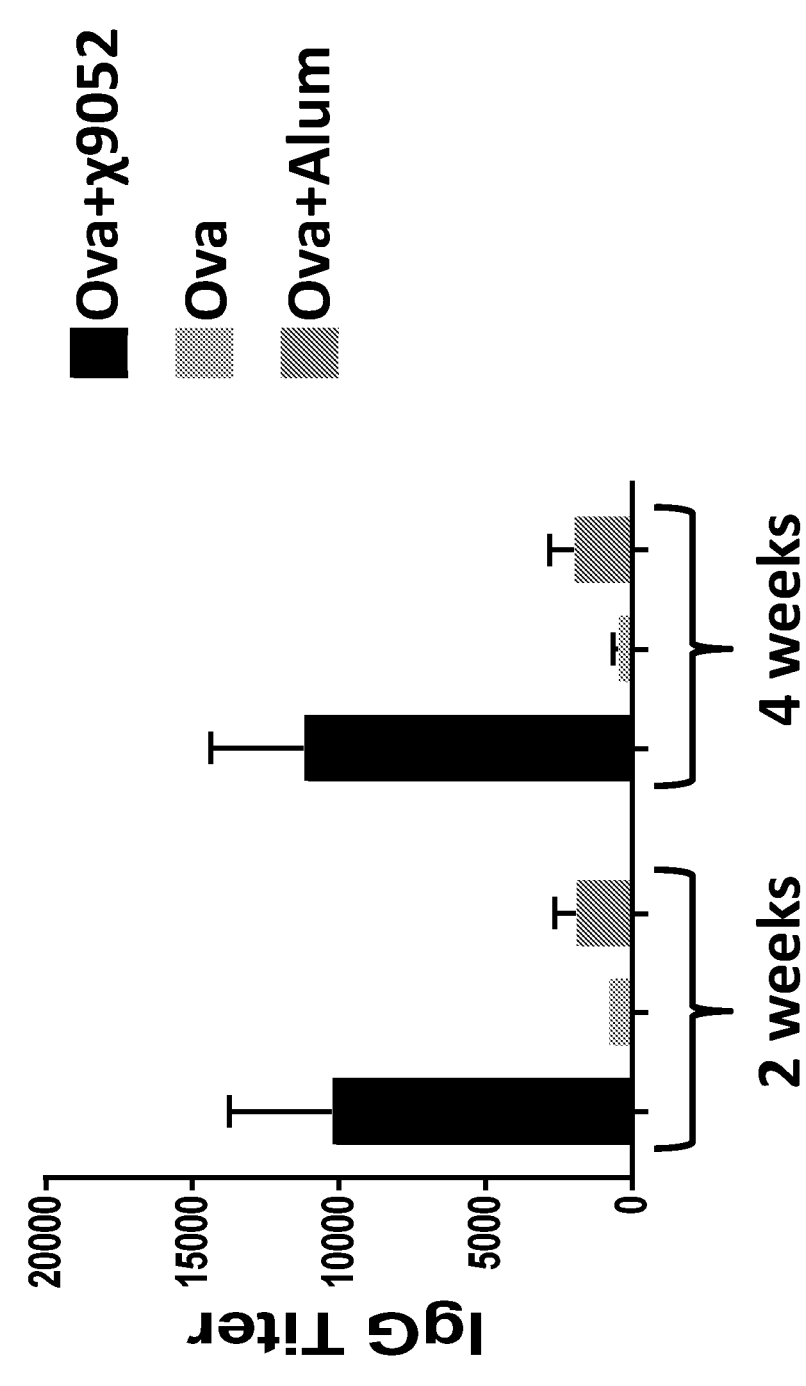

FIG. 7. Activation of Nod1 and Nod2 present in HEK cells by different S. *Typhimurium* mutant strains FIG. 8. Enhanced production of antibody production against Ova by co-administration of Family 1 *Salmonella* adjuvant strain χ9052. 5×106 CFU of χ9052 s.c.; 100 µg Ovalbumen s.c.; 50 µl Alum s.c.

FIG. 9. *Mycobacterium tuberculosis* H37Rv titers in spleens of mice vaccinated with *Mycobacterium bovis* Bacille Calmette-Guerin (BCG) with and without inoculation with ENIIRA strain χ12499 or with χ12499 alone.

FIG. 10. *Mycobacterium tuberculosis* H37Rv titers in spleens of mice vaccinated with *M. bovis* BCG alone or with PIESV χ12068 (pYA4891) or with ENIIRA strains χ12517 or ×12518.

FIG. 11. *Mycobacterium tuberculosis* H37Rv titers in lungs of mice vaccinated with *M. bovis* BCG and/or χ12068 (pYA4891) with or without inoculation with ENIIRA strain χ12518.

Figure 12A:
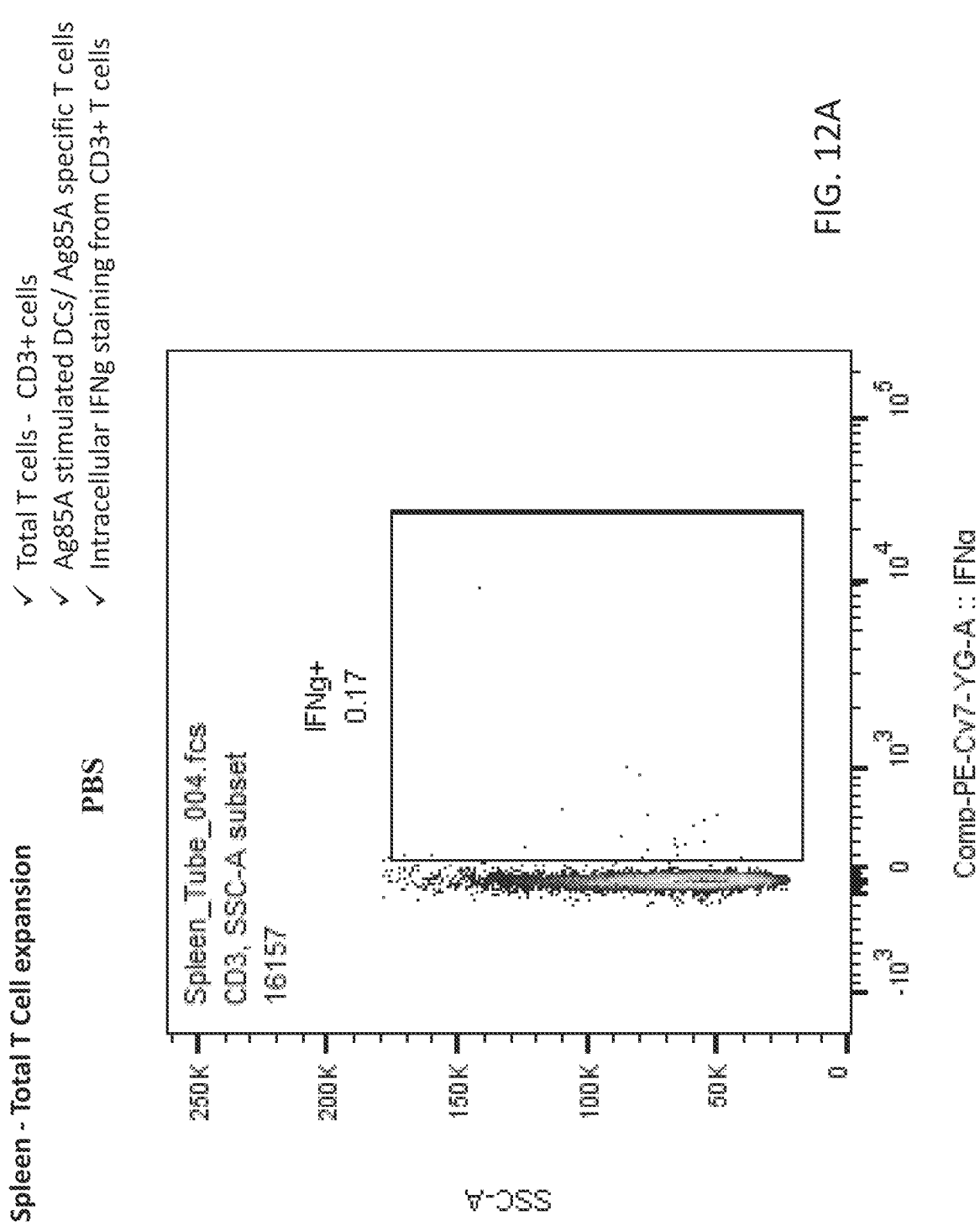
Figure 12C:
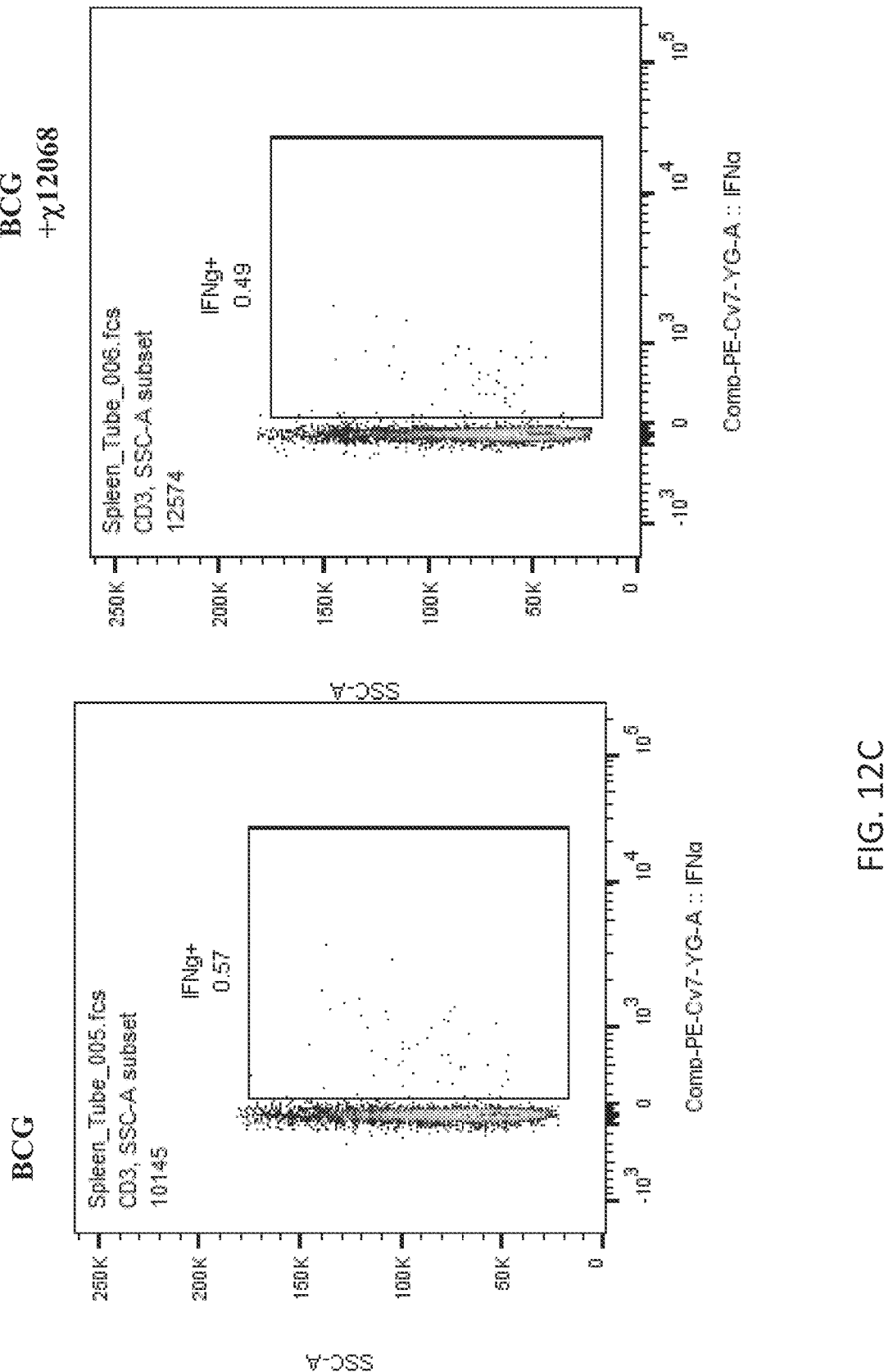
Figure 12D:
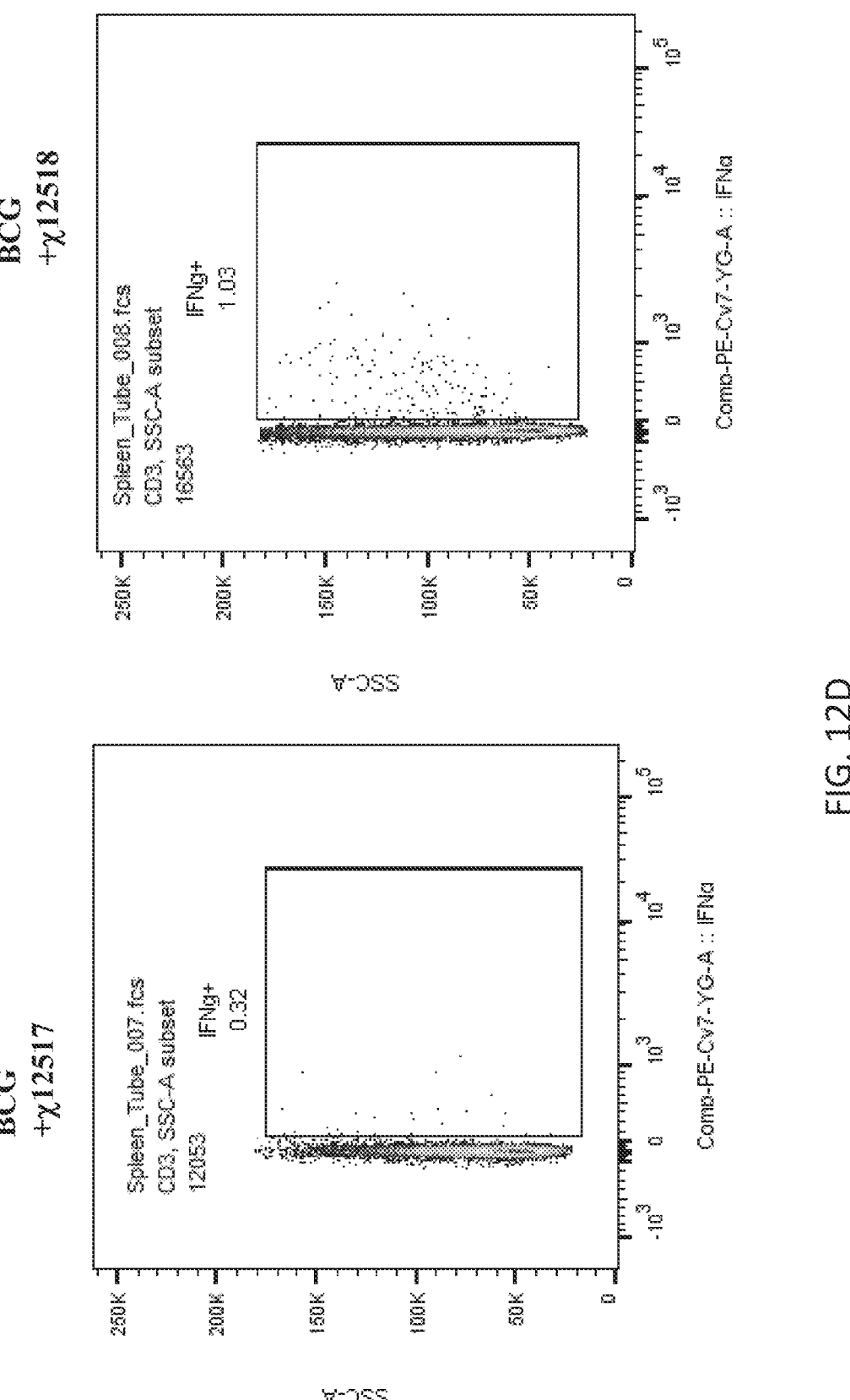

FIG. 12. Analysis of splenic lymphocytes from groups of mice used in Experiment 15 showing expansion of total CD3+ cells stimulated with Ag85A with production of INFγ and the ability of Ag85A to stimulate proliferation using CFSE staining.

FIG. 13. Comparison of the abilities of the AAS strains χ12517 and χ12518 to activate NF-κB synthesis via interactions with TLR4 and TLR5 and with the ability of the wild-type parent χ3761 and purified LPS and flagellin.

FIG. 14. Ability of Attenuated Adjuvant *Salmonella* (AAS) in Experiment 20 to enhance levels of protection of mice against *M. tuberculosis* H37Rv challenge. Left panel: Titers of Mtb H37Rv in lungs six weeks after challenge. Right panel: Titers of Mtb H37Rv in spleens six weeks after challenge-note that the titers for the last 3 groups in which no colonies were detected by plating undiluted suspensions are based on the titers if 1 colony had been detected. The inocula and routes of administration are denoted at the bottom of the Figure (see text for titers of inocula).

Figure 15:
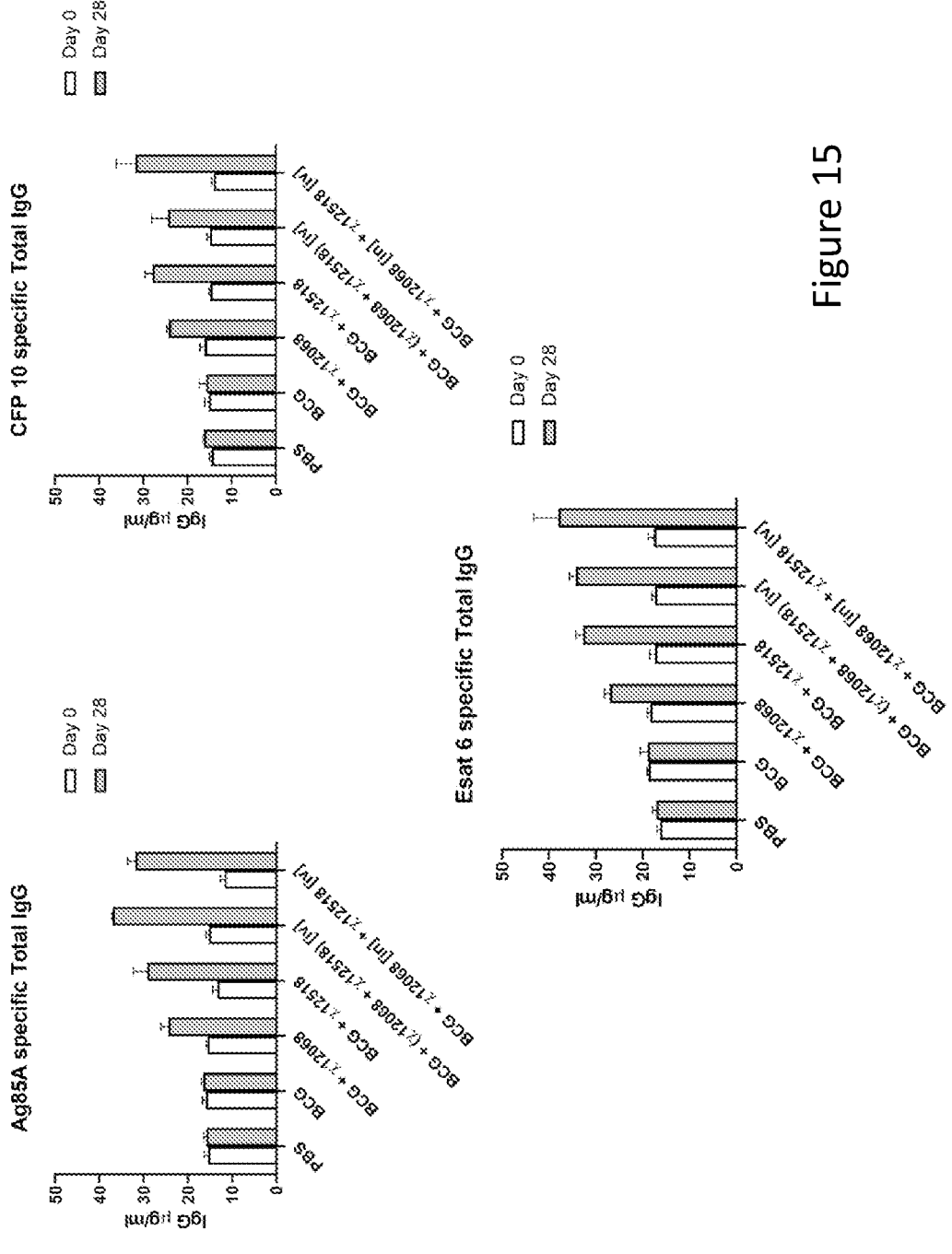

FIG. 15. Antibody titers against the Mtb antigens Ag85A, CFP10 and ESAT-6 in the Groups of mice studied in Experiment 20.

FIG. 16. Western blot analyses of AAS strains to synthesize the truncated FliC180 protein in the presence and absence of synthesizing the FljB phase II flagellin.

FIG. 17. Motility of AAS strains evaluated for flagellin synthesis in FIG. 16 and lack of demonstrated motility in a mutant strain with a (hin-fljBA) phase lock deletion mutation.

Figure 18:
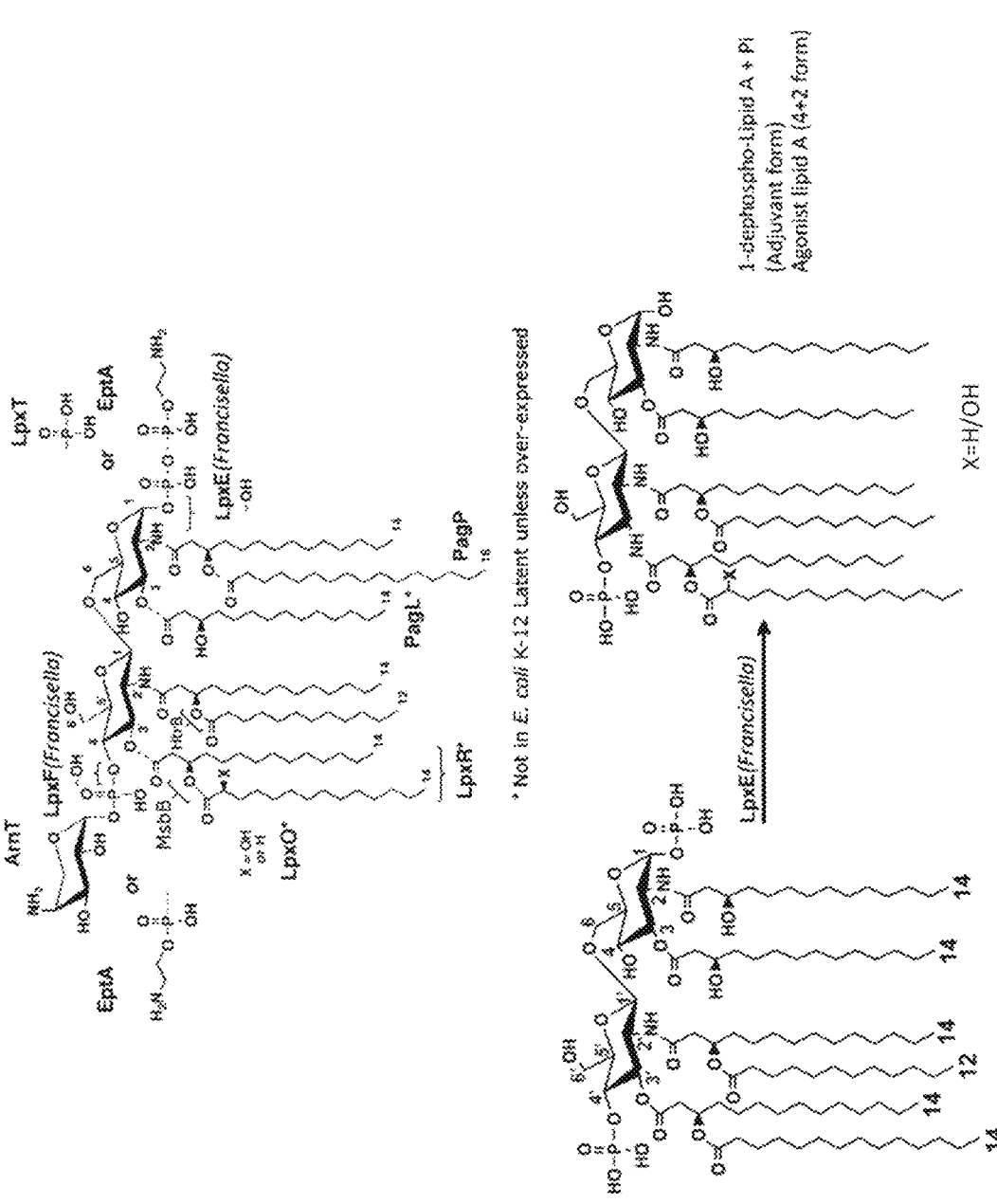

FIG. 18. Structure of S. *Typhimurium* lipid A with indication of the modifications/structures controlled by the indicated S. *Typhimurium* genes. The bottom panel displays the removal of the 1'PO$_4$ from lipid A caused by the expression of the *Francisella tularensis* lpxE gene. The expression of the *F. tularensis* lpxF gene leads to the loss of the 4'PO$_4$ (not shown).

Figure 19:
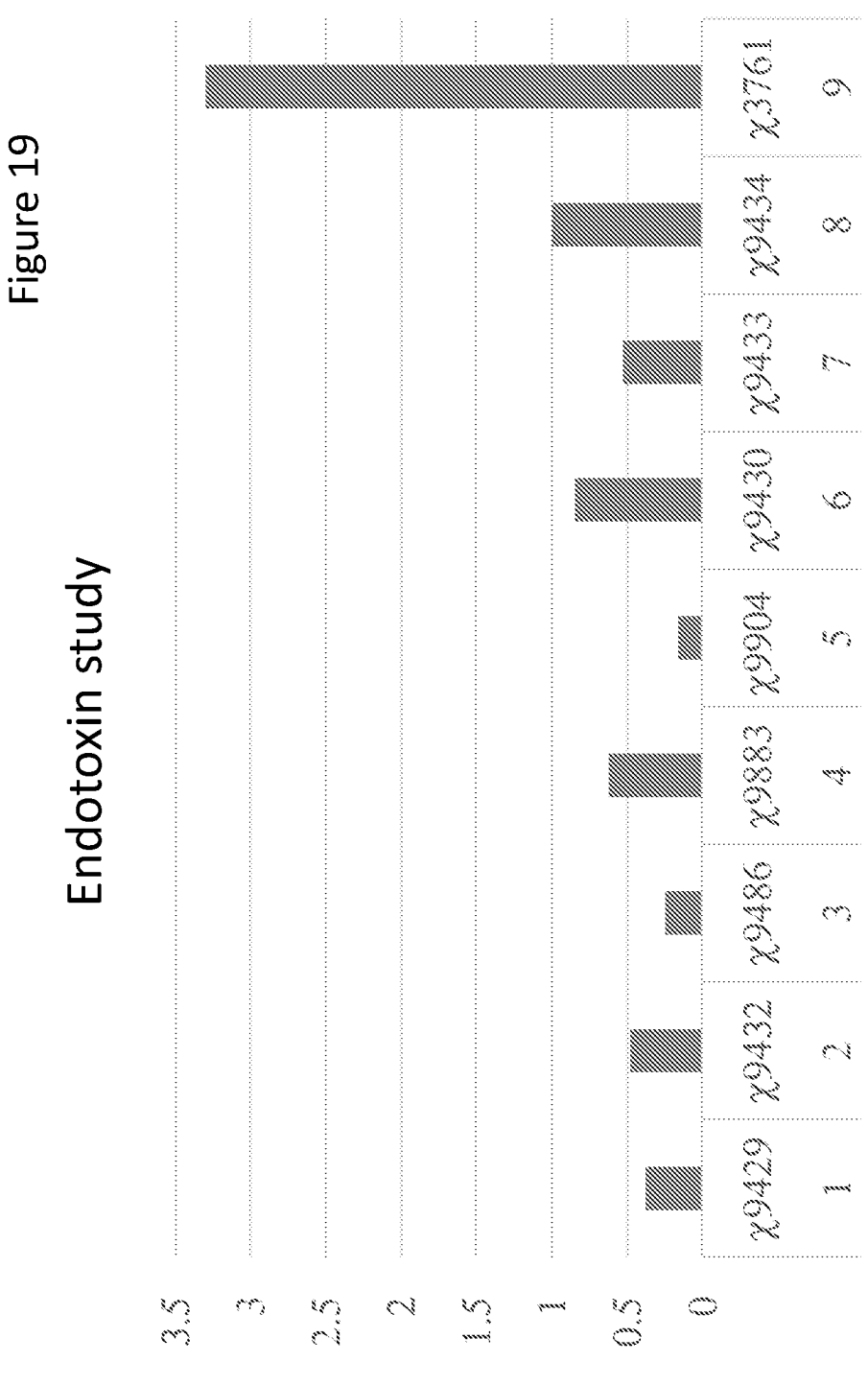

FIG. 19. Determination of endotoxic activities of S. *Typhimurium* strains dependent on genotype. See text for detailed methods and genotypes of strains.

Figure 20:
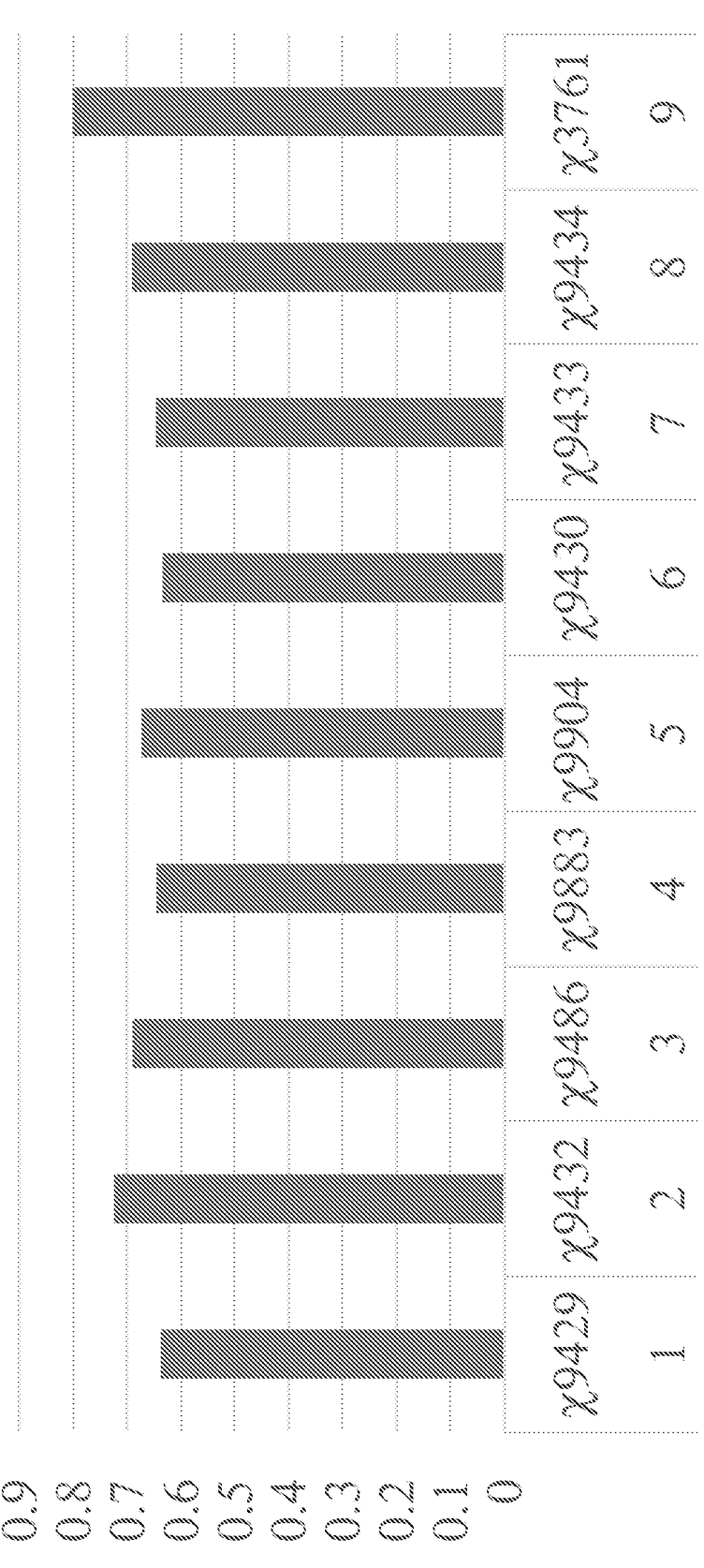

FIG. 20. Activation of NF-κB synthesis by interaction with HEK cells displaying TLR4 in same strains evaluated for endotoxin activities displayed in FIG. 17.

Figure 21:
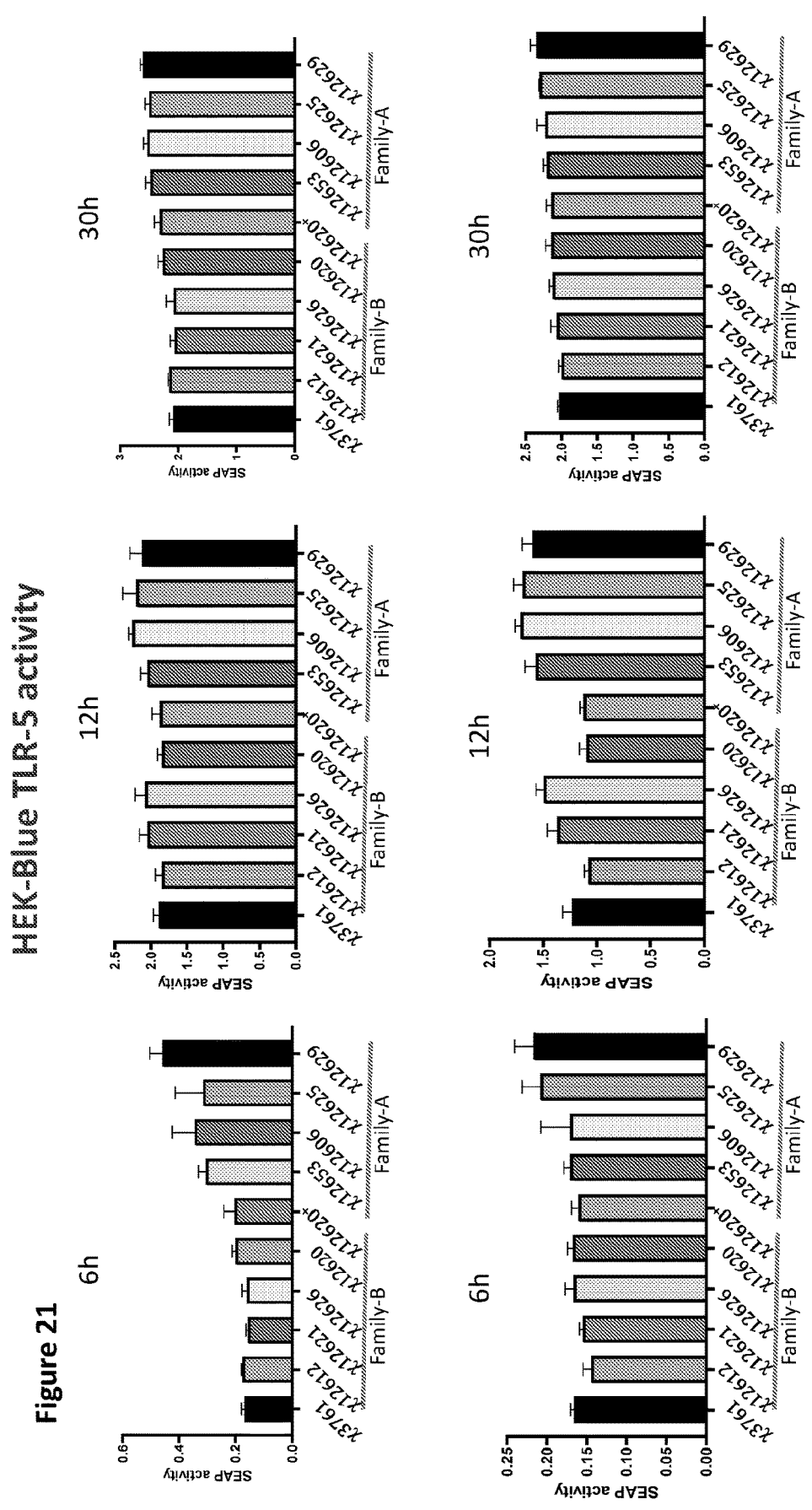

FIG. 21. Activation of NFκB synthesis in HEK cells displaying TLR5 by Family A and B SDAAS strains. See text for detailed methods and genotypes of strains evaluated.

Figure 22:
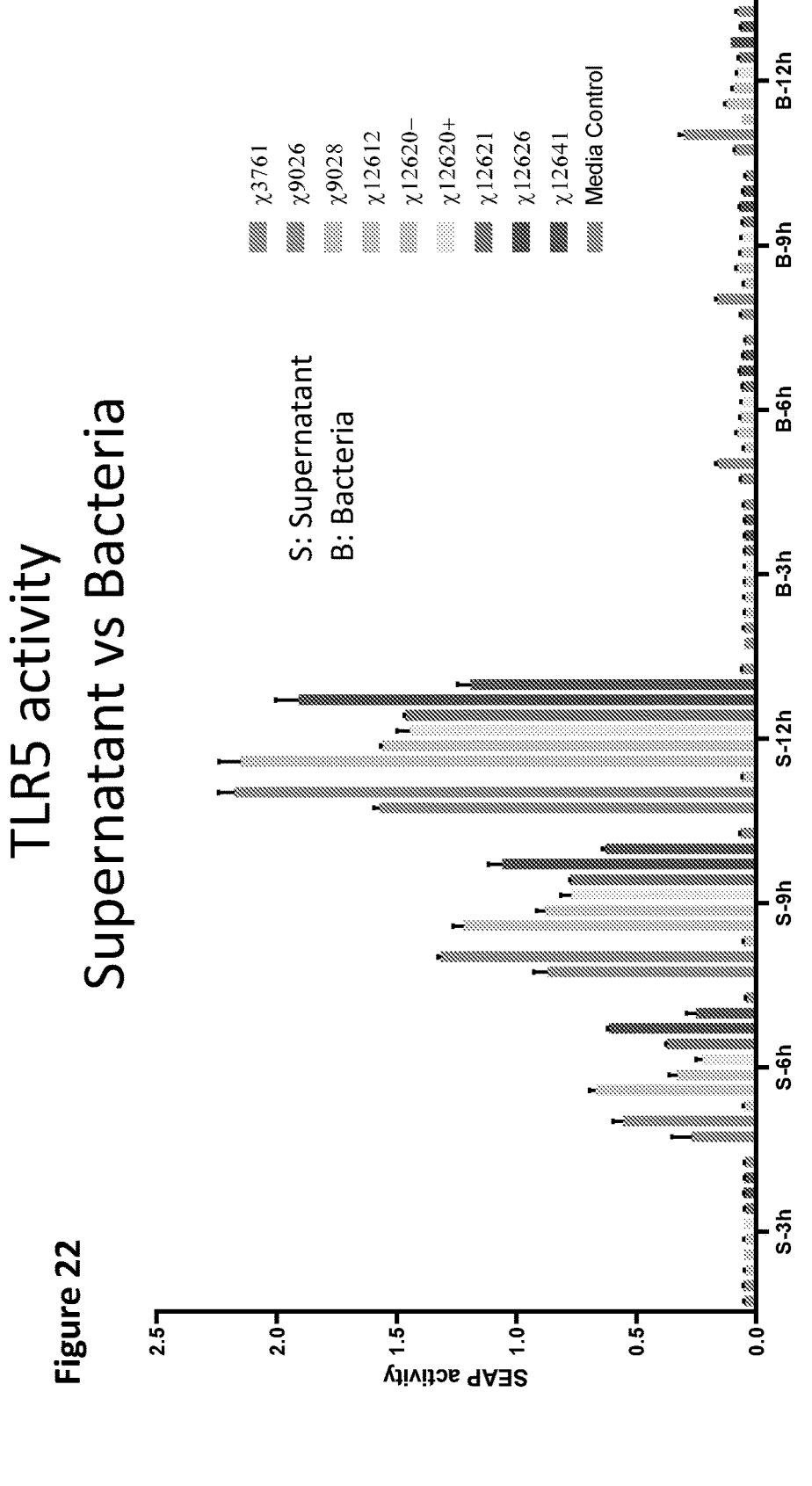

FIG. 22. Demonstration that TLR5 activating flagellin is a secreted gene product released into the supernatant fluid and not remaining attached to surface of SDAAS cells. See text for description of methods and genotypes of tested strains.

Figure 23:
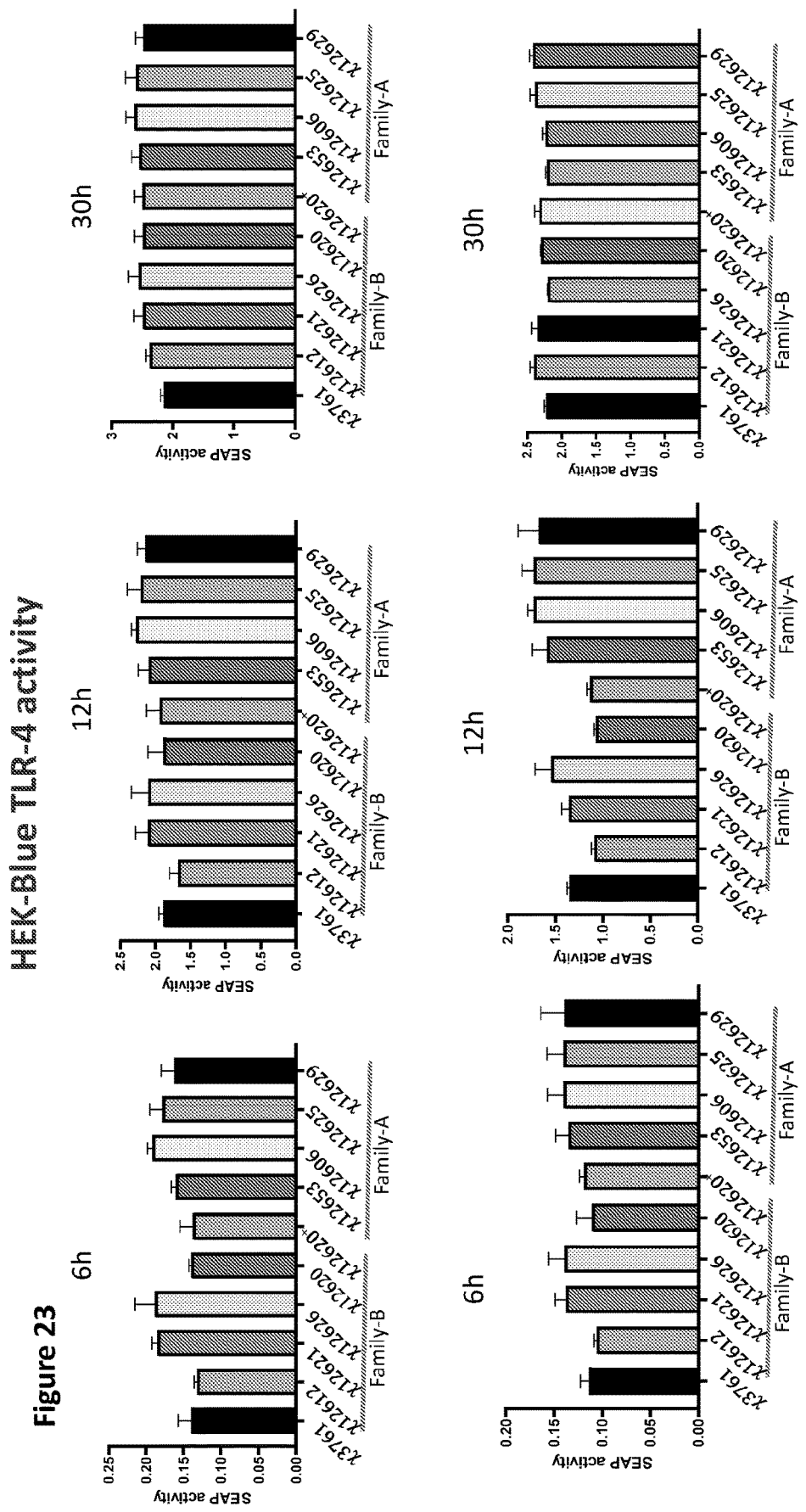

FIG. 23. Activation of NFκB synthesis in HEK cells displaying TLR4 by Family A and B SDAAS strains. See text for detailed methods and genotypes of strains evaluated.

Figure 24:
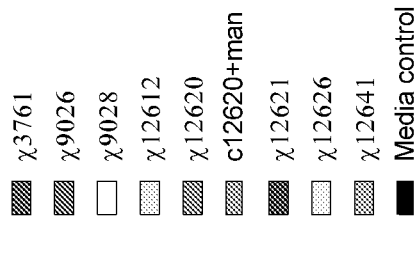

FIG. 24. Demonstration that TLR4 activating modified and unmodified lipid A is present in supernatant of SDAAS strain cultures as well as remaining bound in the outer bacterial cell surface. See text for details of the methods used, the genotype of strains evaluated and an explanation of this unexpected observation.

Figure 25:
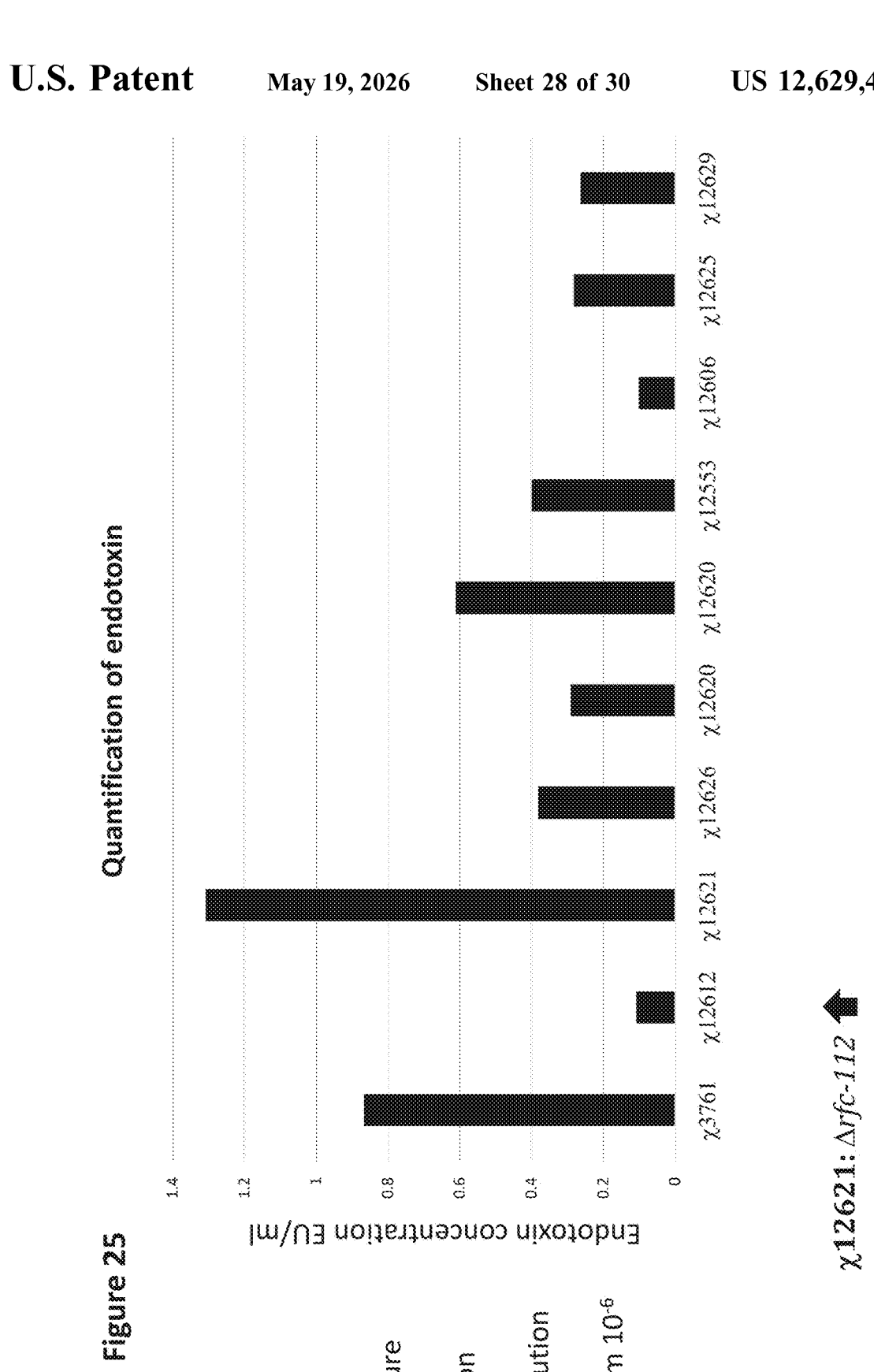

FIG. 25. Evaluation of Family A and B SDAAS strains for endotoxic activities. See text for description of study and genotypes of strains evaluated.

FIG. 26. Evaluation of SDAAS strains for activation of NFκB synthesis in HEK cells internally displaying TLR8 recognizing ssRNA. See text for methods and genotypes of strains evaluated.

Figure 27:
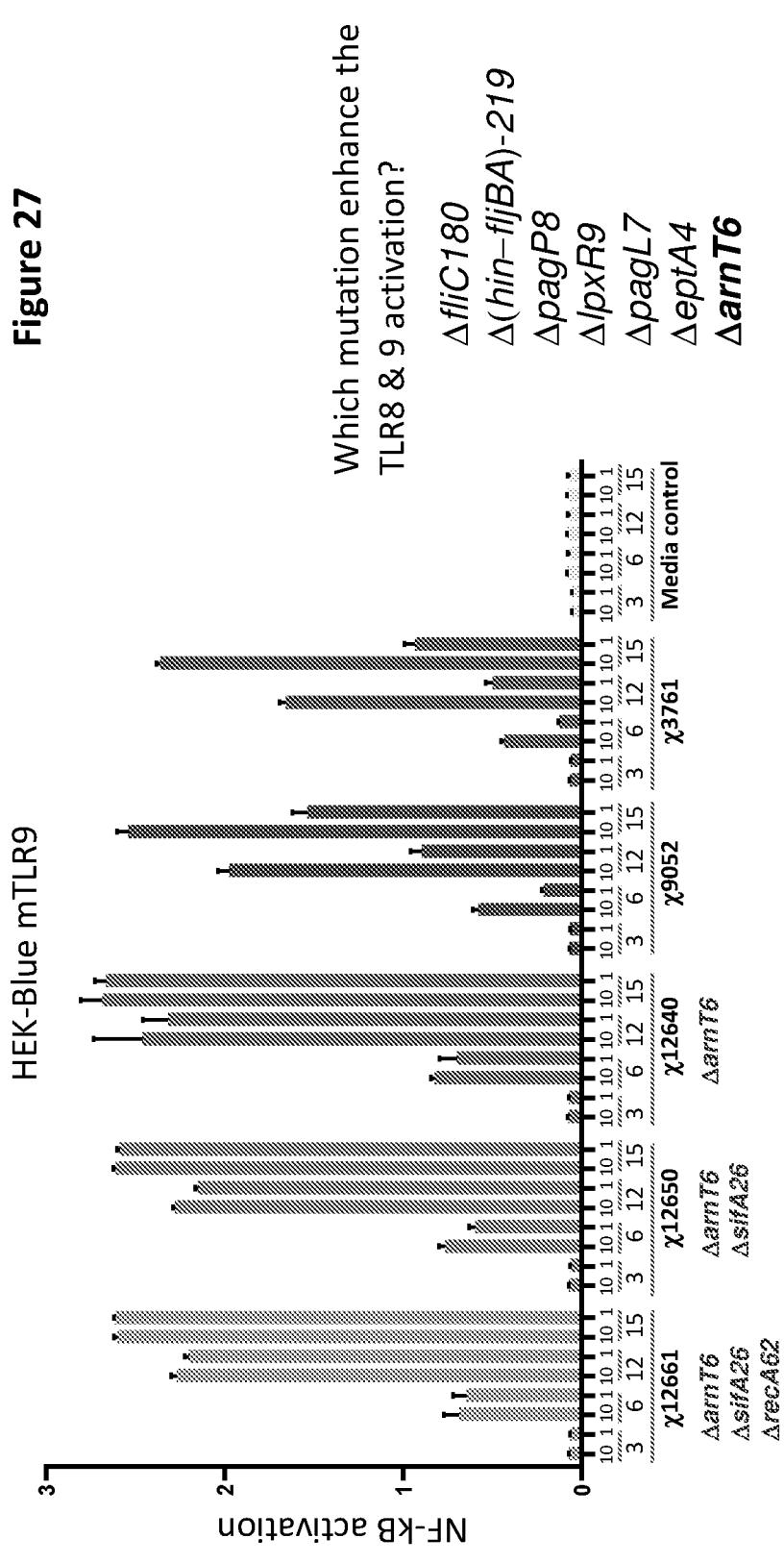

FIG. 27. Evaluation of SDAAS strains for activation of NFκB synthesis in HEK cells internally displaying TLR9 recognizing CpG sequences in DNA. See text for methods and genotypes of strains evaluated.

DETAILED DISCLOSURE

Successful pathogens have evolved to either infect the host in a stealth mode to be undetectable and/or suppress, modulate or circumvent induction of immunity, synthesize subterfuge antigens that induce immune responses that confer no protective immunity and/or devise means to colonize and persist in the host. *Salmonella* vaccine vectors have been continuously modified to eliminate these means as they are discovered and characterized. In addition, other modifications to enhance an induction of innate immune response in the absence of excess inflammation have been made with *Salmonella* vaccine vectors. Additionally, because live bacterial vaccines have the potential to persist in the environment if shed, a method to solve this problem has been devised. This method achieves regulated delayed lysis and thereby ensures that viable vaccine cells do not persist in vivo or survive if shed into the environment.

Based on these attributes and the observation that *Salmonella* vaccine vector strains with these properties are entirely safe when administered to two-hour old mice or to pregnant mice or to protein-malnourished mice or to immunodeficient SCID mice, *Salmonella* strains with some of these properties are used herein to design strains with unique attributes to enhance their safety and efficacy when used as adjuvants. These self-destructing attenuated adjuvant *Salmonella* (SDAAS) strains are designed for use with a diversity of vaccines to augment their abilities to induce protective immunity or have desired abilities to alter physiological functions or combat cancers.

Vaccines for the prevention of multiple infections caused by many pathogens are nonexistent. Currently existing vaccines often only provide partial protective immunity, or, require repeat vaccinations to provide adequate immunity to a subject. Recombinant attenuated *Salmonella* vaccine (RASV) vectors for synthesizing and delivering protective antigens encoded by genes from pathogens have been studied. In contrast to the RASV vectors previously described, empty vector control strains which do not deliver a protective antigen invariably but surprisingly provide low levels of protective immunity to a challenge pathogen. While this low level often exceed the level of immunity conferred by buffered saline, this level was significantly less than in animals receiving vaccine strains delivering protective antigens. Consequently, this low-level protective immunity against bacterial, viral and parasitic pathogens occurs as a result of vaccinating animal hosts with empty vector control RASVs.

Consequently, the discovery of and improvements provided herein of live self-destructing *Salmonella* strains for serving as potent adjuvants (Sal-Adj) for enhancing induction of protective immunity by subunit and live ineffectual vaccines is paramount for the production of universally effective adjuvant strains. This discovery and the ensuing improvements enable use of Sal-Adj constructs to induce low-level protective immunity to challenge of unvaccinated animals and humans to various bacterial, viral and parasitic pathogens. Because of the principal means by which these Sal-Adj strains exert their beneficial activities (as determined in the studies conducted), they are also referred to as ENhanced Innate Immunity Response Activators (ENIIRAs) and, more recently, as Self-Destructing Attenuated Adjuvant *Salmonella* (SDAAS) strains. Optimal doses, routes and times of administration to enhance induction of protective immunity against infection and persistence by pathogens will be elucidated herein. In a similar way, the RASV vector strains now improved with features to diminish their abilities to subvert induction of immunity and increasing their immunogenicity by enhancing stimulation of innate immunity are now termed Protective Immunity Enhanced *Salmonella* Vaccine (PIESV) vectors.

Definitions

As used herein the specification, "a" or "an" may mean one or more, unless clearly indicated otherwise. As used herein in the claims, when used in conjunction with the word "comprising," the words "a" or "an" may mean one or more than one.

As used herein, "codon" means, interchangeably, (i) a triplet of ribonucleotides in an mRNA which is translated into an amino acid in a polypeptide or a code for initiation or termination of translation, or (ii) a triplet of deoxyribonucleotides in a gene whose complementary triplet is transcribed into a triplet of ribonucleotides in an mRNA which, in turn, is translated into an amino acid in a polypeptide or a code for initiation or termination or translation. Thus, for example, 5'-TCC-3' and 5'-UCC-3' are both "codons" for serine, as the term "codon" is used herein.

The terms "comprise," "have," and "include" are open-ended linking verbs. Any forms or tenses of one or more of these verbs, such as "comprises," "comprising," "has," "having," "includes," and "including," are also open-ended. For example, any method that "comprises," "has" or "includes" one or more steps is not limited to possessing only those one or more steps and also covers other unlisted steps.

The term "consisting essentially of" when used in conjunction with adjuvant containing compositions described herein refers to a composition comprising a Sal-Adj or ENIIRA or SDAAS strain and a pharmaceutical carrier without any other immune response enhancing components.

The term "agent" as used herein refers to either adjuvant and/or vaccine.

As used herein, the term "adjuvant" refers to an agent that stimulates and/or enhances an immune response in a subject. An adjuvant can stimulate and/or enhance an immune response in the absence of an antigen and/or can stimulate and/or enhance an immune response in the presence of an antigen. Exemplary embodiments of adjuvants disclosed herein are ENIIRA or SDAAS strains.

The term "administering" or "administration" of an agent as used herein means providing the agent to a subject using any of the various methods or delivery systems for administering agents or pharmaceutical compositions known to those skilled in the art. Agents described herein may be administered by oral, intradermal, intravenous, intramuscular, intraocular, intranasal, intrapulmonary, epidermal, subcutaneous, mucosal, or transcutaneous administration.

The term "co-administration" or "co-administering" as used herein refers to the administration of an active agent before, concurrently, or after the administration of another active agent such that the biological effects of either agents overlap.

The term "gene", as used herein, refers to a nucleic acid sequence that encodes and expresses a specific protein. In some embodiments, a gene may include a regulatory sequence of a 5'-non-coding sequence and/or a 3'-non-coding sequence.

An "immune response enhancing amount" is that amount of an adjuvant administered sufficient to enhance an immune response of vaccine administration in a subject compared to vaccine administration without adjuvant administration. An immune response enhancing amount can be administered in one or more administrations.

As used herein, the term "immunogen" refers to an antigen that is recognized as unwanted, undesired, and/or foreign in a subject.

As used herein, the term "immune response" includes a response by a subject's immune system to a vaccine. Immune responses include both cell-mediated immune responses (responses mediated by antigen-specific T cells and non-specific cells of the immune system) and humoral immune responses (responses mediated by antibodies present in the plasma lymph, tissue fluids and mucosal secretions). The term "immune response" encompasses both the initial responses to an immunogen as well as memory responses that are a result of "acquired immunity."

The term "codon-optimized" as used herein refers to sequences that have been modified from their natural form to incorporate codons that are highly expressed or preferred by the organism in which they are introduced. Oligonucleotide and/or gene syntheses of pathogen specified protective and putative protective antigens may be codon-optimized to enhance translational efficiency in *Salmonella* by using codons used most frequently by highly expressed *Salmonella* genes and with codon selection to make the final sequence within about 2-3% of the average 52% GC content of the *Salmonella* genome. In some instances, codons are also changed to stabilize mRNA by "destroying" RNase E cleavage sites to prolong mRNA half-life. (see McDowall K J, Kaberdin V R, Wu S W, Cohen S N, Lin-Chao S. Site-specific RNase E cleavage of oligonucleotides and inhibition by stem-loops. Nature. 1995; 374 (6519): 287-90. Epub 1995 Mar. 16. doi: 10.1038/374287a0. PubMed PMID: 7533896 and Lin-Chao S, Wong T T, McDowall K J, Cohen S N. Effects of nucleotide sequence on the specificity of rne-dependent and RNase E-mediated cleavages of RNA I encoded by the pBR322 plasmid. J Biol Chem. 1994; 269 (14): 10797-803. Epub 1994 Apr. 8. PubMed PMID: 7511607), which are incorporated herein by reference. Provided below are preferred codons (1 letter symbol and codon):

F-tcc
S-tct
Y-tac
C-tgc
W-tgg
I-atc
M-atg
L-ctg
P-ccg
H-cac
Q-cag
R-cgt
V-gtt
T-acc
N-aac
K-aaa
A-gcg
D-gat
E-gaa
G-ggt Based on the foregoing list, one or more modifications to the natural sequence may be made to reflect the above codon for the appropriate amino acid.

As used herein, "nucleic acid" or "nucleic acid sequence" refers to polynucleotides, such as deoxyribonucleic acid (DNA) or ribonucleic acid (RNA), oligonucleotides, fragments generated by the polymerase chain reaction (PCR), and fragments generated by any of ligation, scission, endonuclease action, and exonuclease action. Nucleic acid molecules can be composed of monomers that are naturally-occurring nucleotides (such as DNA and RNA), or analogs of naturally-occurring nucleotides (e.g., a-enantiomeric forms of naturally-occurring nucleotides), or a combination of both. The term "nucleic acid" or "nucleic acid sequence" also pertains to codon optimized nucleic acid sequences as defined herein.

As used herein, the phrase "stimulating or enhancing an immune response" refers to an increase in an immune response in the subject following administration of a vaccine with an adjuvant of the disclosed embodiments relative to the level of immune response in the subject when a vaccine has been administered without an adjuvant.

As used herein, the term "vaccine" refers to an immunogen or a composition comprising an immunogen that elicits an endogenous immune response in a subject (e.g., a human or animal). The endogenous immune response may result in, for example, the switching of a Th1 biased immune response to a Th2 biased immune response, the activation or enhancement of T effector cell responses and/or the reduction of T regulatory cell response, the activation of antigen-specific naive lymphocytes that may then give rise to antibody-secreting B cells or antigen-specific effector and memory T cells or both, and/or the direct activation of antibody-secreting B cells.

The term "pharmaceutically acceptable carrier" as used herein refers to one or more formulation materials suitable for accomplishing or enhancing the successful delivery of the pharmaceutical composition of the Sal-adj or SDAAS strains disclosed herein. As used herein, the term "carrier" refers to a pharmaceutically acceptable solid or liquid filler, diluent or encapsulating material. A water-containing liquid carrier can contain pharmaceutically acceptable additives such as acidifying agents, alkalizing agents, antimicrobial preservatives, antioxidants, buffering agents, chelating agents, complexing agents, solubilizing agents, humectants, solvents, suspending and/or viscosity-increasing agents, tonicity agents, wetting: agents or other biocompatible materials. A tabulation of ingredients listed by the above 15 categories, may be found in the *U.S. Pharmacopeia National Formulary,* 1857-1859, (1990). Examples of liquid carriers include, but are not limited to, water, saline, dextrose, glycerol, ethanol and mixtures thereof.

The term "protective immunity" as used herein refers to induction of an immune response upon administration of a vaccine sufficient to confer protection against a pathogen or to have a therapeutic effect by arresting a disease such as cancer.

Overview and Preliminary Studies

1. Bacterial Strains for Adjuvant Compositions.

Many S. *Typhimurium* strains with individual and combinations of deletion and deletion-insertion mutations have been isolated/constructed and all the suicide vectors for these constructions are available to move these mutations into strains to create new Sal-Adj/ENIIRA/SDAAS strains.

Table 1 lists the mutations and their associated phenotypic attributes that were used in these studies. Based on our prior results and the considerations discussed above, we began with three parental strains that exhibit lysis in vivo but with different periods of time needed for lysis and will therefore disperse into tissues away from the inoculation site to different extents. All these strains exhibit complete biological containment features being unable to persist in vivo or survive if released into the environment.

Family A: χ9052 Δalr-3 ΔdadB4 ΔasdA33—requires D-alanine (*Salmonella* has two alanine racemases) and diaminopimelic acid (DAP) that are unique essential constituents of peptidoglycan that provides the rigid layer of the bacterial cell wall. D-alanine and DAP are only synthesized by bacteria and are totally absent in animal tissues.

Family B: χ12499 Δalr-3 $\Delta P_{dadB66}$::TT araC $P_{araBAD}$ dadB $\Delta P_{asdA55}$::TT araC $P_{araBAD}$ asd—requires presence of arabinose since synthesis of D-alanine and DAP are totally dependent on arabinose-induced synthesis of the dadB-encoded alanine racemase and the asdA-encoded aspartate semialdehyde dehydrogenase. The second alanine racemase that synthesizes D-alanine is absent due to the Δalr-3 mutation. Arabinose is absent in animal tissues but this strain undergoes several cell divisions in vivo until the dadB- and asdA-encoded enzymes are diluted by cell division so that D-alanine and DAP synthesis are insufficient to maintain peptidoglycan integrity.

Family C: χ11730 $\Delta P_{murA25}$::TT araC $P_{araBAD}$ murA ΔasdA27::TT araC $P_{araBAD}$ c2 Δ(wza-wcaM)-8 ΔrelA198::

araC $P_{araBAD}$ lacI TT—must be used with a lysis plasmid that also has araC $P_{araBAD}$ regulation of the murA and asdA genes (see next section) to yield a strain that is totally dependent on arabinose-induced synthesis of the enzymes needed to synthesize DAP and muramic acid (another unique essential constituent of peptidoglycan). Depending on the complementing plasmid copy number used, this strain will disseminate more widely and attain higher titers in animal tissues prior to onset of lysis than strains in Families A and B.

The various mutations that are being used to conduct studies to determine the optimal means to stimulate innate immunity that is not excessively inflammatory are listed in Table 1 along with the mutations present in the Family A, B and C starting strains.

TABLE 1

| Mutations and associated phenotypes in S. Typhimurium adjuvant strains[a] | |
| --- | --- |
| Genotype | Phenotype |
| A. Deletion and deletion-insertion mutations to facilitate regulated delayed lysis in vivo | |
| $\Delta P_{murA}$::TT araC $P_{araBAD}$ murA | makes synthesis of MurA, the first enzyme in the synthesis of muramic acid, dependent on arabinose in growth medium and ceases synthesis in vivo due to absence of arabinose (1,2). MurA decreases due to cell division in vivo to ultimately cause lysis and death (2). The murA defect is complemented by MurA⁺ plasmid vectors (1). $\Delta$mur A mutations are lethal since the product of the gene is phosphorylated that precludes its uptake by *Salmonella* cells. |
| $\Delta$asdA | encodes aspartate semialdehyde dehydrogenase essential for synthesis of diaminopimelic acid (DAP) necessary for peptidoglycan synthesis (3). |
| $\Delta P_{asdA}$::TT araC $P_{araBAD}$ asdA $\Delta$alr | makes synthesis of AsdA dependent on presence of arabinose encodes one of two alanine racemases essential for synthesis of D-alanine necessary for peptidoglycan synthesis (4). |
| $\Delta$dadB | encodes one of two alanine racemases essential for synthesis of D-alanine necessary for peptidoglycan synthesis (4). |
| $\Delta P_{dadB66}$::TT araC $P_{araBAD}$ dadB | makes synthesis of DadB dependent on presence of arabinose |
| $\Delta$(wza-wcaM) | eliminates twenty enzymes needed to synthesize several exopolysaccharides that promote biofilm formation facilitating persistence and synthesis of GDP-fucose required for colanic acid synthesis (5), which protects cells undergoing cell wall-less death from lysing (6). These exopolymers are also immunosuppressive. |
| $\Delta$relA | the relA mutation uncouples growth regulation from a dependence on protein synthesis, an important attribute in strains with regulated delayed lysis (7, 8) |
| B. Mutations enabling regulation of genes that might be present on plasmid vectors in conjunction with strains undergoing regulated delayed lysis in vivo | |
| $P_{trc}$ | a promoter expressed at high level under both anaerobic and aerobic conditions and repressed by LacI (9, 10) |
| $\Delta$relA::araC $P_{araBAD}$ lacI TT | the arabinose-dependent synthesis of the LacI repressor is to enable a regulated delayed expression of DNA sequences under the control of $P_{trc}$ (11) |
| $\Delta$asdA::TT araC $P_{araBAD}$ c2 | the Asd enzyme is essential for the synthesis of DAP required for peptidoglycan synthesis (12). The arabinose-dependent synthesis of the C2 repressor enables a regulated delayed expression of DNA sequences under control of C2 repressed promoters (1). The $\Delta$asdA mutation is complemented by Asd⁺ plasmids (13). |
| Phage P22 $P_R$ | promoter is repressible by arabinose-dependent synthesis of the C2 repressor (14) |
| C. Mutations altering synthesis of LPS components | |
| $\Delta$pagP::$P_{lpp}$ lpxE mutation | causes regulated delayed in vivo synthesis of the codon-optimized lpxE gene from *Francisella tularensis* to cause synthesis of the non-toxic adjuvant form of LPS lipid A monophosphoryl lipid A (MPLA)(15). The pagP mutation also eliminates a means by which *Salmonella* alters LPS lipid A in vivo to decrease recruitment of innate immunity by interaction with TLR4 (16) |
| $\Delta$pagL | eliminates a means by which *Salmonella* alters LPS components in vivo to decrease recruitment of innate immunity by interaction with TLR4 (16) |
| $\Delta$lpxR | eliminates another means by which *Salmonella* alters LPS components in vivo to decrease recruitment of innate immunity by interaction with TLR4 (16) |
| $\Delta$arnT | eliminates a means by which *Salmonella* alters LPS lipid A in vivo to decrease recruitment of innate immunity by interaction with TLR4 (51) |
| $\Delta$eptA | eliminates a means by which *Salmonella* alters LPS lipid A in vivo to decrease recruitment of innate immunity by interaction with TLR4 (52) |
| $\Delta$waaC | eliminates an enzyme needed to synthesize LPS core resulting in a deep-rough phenotype and also renders *Salmonella* totally attenuated (49) |
| $\Delta$waaG | eliminates an enzyme needed to synthesize LPS core resulting in a medium-rough phenotype and also renders *Salmonella* totally attenuated (49) |

TABLE 1-continued

| Mutations and associated phenotypes in S. Typhimurium adjuvant strains[a] | |
| --- | --- |
| Genotype | Phenotype |
| ΔwaaL | eliminated the enzyme that joins the LPS O-antigen chain to the LPS core resulting in a moderate-rough phenotype and also renders *Salmonella* totally attenuated (49) |
| | D. Mutations altering synthesis of flagellar components |
| ΔfliC180 | a specific mutation in the fliC gene encoding the Phase I flagellin protein (17) that contains the TLR5 receptor and a CD4 T-cell epitope. The mutation prevents synthesis of flagella. |
| ΔfliC2426 | deletes fliC gene to eliminate synthesis of Phase I flagellin (17) |
| ΔfliB217 | deletes fljB gene to eliminate synthesis of Phase II flagellin (17) |
| Δ(hin-fljBA) | deletes the sequence necessary for phase switching of flagellin synthesis and eliminates synthesis of the phase II flagellin and the repressor of the fliC gene |
| | E. Mutations altering synthesis of fimbrial components |
| ΔP$_{stc}$::P$_{murA}$ stc | causes constitutive synthesis of the in vivo expressed Stc fimbriae that contribute to immunogenicity (18) |
| ΔstcABCD | eliminates synthesis of Stc fimbriae (18) |
| ΔP$_{saf}$::P$_{murA}$ saf | causes constitutive synthesis of the in vivo expressed Saf fimbriae that contribute to immunogenicity (18) |
| ΔsafABCD | eliminates synthesis of Saf fimbriae (18) |
| | F. Mutations eliminating or diminishing effective immunogenicity |
| ΔsifA | enables *Salmonella* to escape the SCV for lysis in cytosol (19) and eliminates a means of immunosuppression (20) |
| ΔsteE | |
| | G. Mutations leading to degradation of DNA within Salmonella cells |
| ΔrecA | enhances rate of DNA digestion in *Salmonella* cells as a consequence of recombination to liberate DNA fragments with CpG sequences and also renders *Salmonella* totally attenuated (53) |

[a]Δ = deletion;
TT = transcription terminator;
P = promoter

35

Table 2 lists the suicide plasmids used to move the mutations including deletion and deletion-insertion mutations listed and described in Table 1 into the Sal-Adj/ENIIRA strains constructed including the Family A, B and C strains listed above and their derivatives described in following sections and Examples as well as in strains yet to be constructed.

TABLE 2

| Suicide vectors for constructing the mutations in Table 1 | | |
| --- | --- | --- |
| Genotype | Suicide Vector | Marker |
| A. Deletion and deletion-insertion mutations to facilitate regulated delayed lysis in vivo | | |
| ΔP$_{murA}$::TT araC P$_{araBAD}$ murA | pYA4686 | Cm |
| ΔasdA | pYA3736 | Cm |
| ΔP$_{asdA}$::TT araC P$_{araBAD}$ asdA | pG8R71 | Cm |
| Δalr | pYA3667 | Cm |
| ΔdadB | pYA3668 | Cm |
| ΔP$_{dadB66}$::TT araC P$_{araBAD}$ dadB | pG8R73 | Cm |
| Δ(wza-wcaM) | pYA4368 | Cm |
| ΔrelA | pYA3679 | Cm |
| B. Mutations enabling regulation of genes that might be present on plasmid vectors in conjunction with strains undergoing regulated delayed lysis in vivo | | |
| ΔrelA::araC P$_{araBAD}$ lacI TT | pYA4064 | Cm |
| ΔasdA::TT araC P$_{araBAD}$ c2 | pYA4138 | Cm |
| C. Mutations altering synthesis of LPS components | | |
| ΔpagP::P$_{lpp}$ lpxE | pYA4295 | Cm |
| ΔpagL | pYA4284 | Cm |
| ΔlpxR | pYA4287 | Cm |
| ΔarnT | pYA4286 | Cm |
| ΔeptA | pYA4283 | Cm |
| ΔwaaC | pYA5473 | Cm |
| ΔwaaG | pYA4896 | Cm |
| ΔwaaL | pYA4900 | Cm |

TABLE 2-continued

| Suicide vectors for constructing the mutations in Table 1 | | |
| --- | --- | --- |
| Genotype | Suicide Vector | Marker |
| D. Mutations altering synthesis of flagellar components | | |
| ΔfliC180 | pYA3729 | Cm |
| ΔfliC2426 | pYA3702 | Cm |
| ΔfliB217 | pYA3548 | Tet |
| Δ(hin-fljBA) | pG8R306 | Cm |
| E. Mutations altering synthesis of fimbrial components | | |
| ΔP$_{stc}$::P$_{murA}$ stc | pYA5053 | Cm |
| ΔstcABCD | pYA5007 | Tet |
| ΔP$_{saf}$::P$_{murA}$ saf | pYA5055 | Cm |
| ΔsafABCD | pYA4586 | Tet |
| F. Mutations eliminating or diminishing effective immunogenicity | | |
| ΔsifA | pYA3716 | Cm |
| G. Mutations leading to degradation of DNA within *Salmonella* cells | | |
| ΔrecA | pYA4680 | Cm |

$^a$ Δ = deletion;
TT = transcription terminator;
P = promoter

2. Plasmids for Adjuvant Strains with Regulated Delayed Lysis In Vivo. Family C

Figure 1:
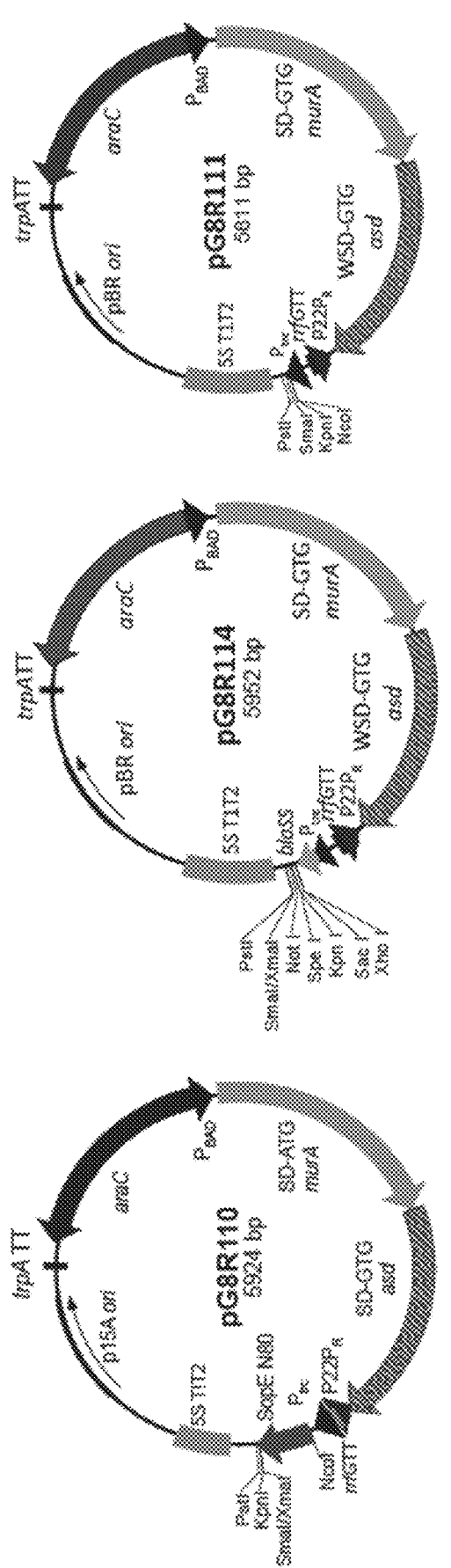
FIG. 1. Plasmid maps. (A) Lysis vector pG8R111, pBR ori; pYA4589 p15A ori; and pYA4595 pSC101 ori. (B) Lysis vectors with improved T2SS bla SS pG8R112, pSC101 ori; pG8R113, p15A ori, and pG8R114, pBR ori. (C) Lysis vector with T3SS SopE N-80 pG8R110, p15A ori.

Family C Sal-Adj (SDAAS) strains will be used in conjunction with plasmids conferring a regulated delayed lysis in vivo phenotype (FIG. 1). This phenotype is due to the araC P$_{araBAD}$-regulated murA and asd genes with GTG start codons to decrease translation efficiency and the P22 P$_R$ (located in opposite orientation to transcription of the araC P$_{araBAD}$ GTG-murA GTG-asd genes) that is repressed by the C2 repressor encoded in the ΔasdA27::TT araC P$_{araBAD}$ c2 mutation. MurA, AsdA and C2 are synthesized when Family C strains are grown with arabinose but cease to be synthesized in vivo. Thus, as C2 concentration decreases due to cell division in vivo, P$_R$-directed anti-sense mRNA synthesis commences to block translation of residual asdA and murA mRNA. Transcription terminators (TT) flank all plasmid domains for controlled lysis, replication and gene expression so that expression in one domain does not affect activities of another domain. The time of onset of in vivo lysis can be controlled, in part, by using plasmids with different copy numbers. These plasmids, especially those with Type 2 and 3 secretion systems (T2SS; T3SS), can be used to synthesize and deliver different effector molecules such as single and double stranded RNA, flagellins, pilins, lipo-proteins or to enable synthesis and delivery of macromolecules such as teichoic acid, lipo-teichoic acid, mannan, etc. to enhance induction of innate immune responses.

3. Observations with Unexpected Ability of Empty Vector Control RASV Strains to Confer Low-Level Protective Immunity to Pathogens or Decreased Ability of Pathogens to Multiply in Hosts or Reduce Performance.

As stated above, we have observed, in developing RASV/PIESV vectored vaccines, that the empty vector control groups (having a vector plasmid not encoding a protective antigen) invariably had higher survival or performance after challenge than the control groups receiving buffered saline (BS). This was especially true with vaccine vector strains that undergo lysis in various cell compartments in vivo. This implied that we might be recruiting innate immunity via activation of internal Nod and TLR9 receptors by release of peptidoglycan components and DNA intracellularly. We present results from some of these studies in Table 3.

TABLE 3

| Empty vector PIESVs and protective immunity* | | | | | |
| --- | --- | --- | --- | --- | --- |
| | | | | Percent Survival | |
| Pathogen | RASV | Path challenge | BS | PIESV-Ag | PIESV + Ag |
| Influenza | PIESV-Flu | Influenza WSN Av (3) | 16 | 29 | 90 |
| *Yersinia pestis* | PIESV-Yp | *Y pestis* (s.c.) Av (3) | 0 | 38 | 83 |
| *S. pneumoniae* | PIESV-Sp | *S. pneumoniae* Av (7) | 0 | 5 | 61 |
| *M. tuberculosis* | PIESV-Mtb | *M. tuberculosis* | Empty vector control reduced Mtb colonization more than BS (3 comparisons) | | |
| *C. perfringens* | RASV-Cp | *C. perfringens* | Empty vector reduced lesions & mortality, enhanced feed conversion & weight gain more than BS (4 comparisons) | | |
| *E. tenella* | PIESV-Eimeria | *Eimeria* | Empty vector enhanced feed conversion & weight gain more than BS (2 comparisons) | | |

*First 4 studies in inbred mice and last 2 studies in outbred chickens

The empty vector PIESV strains used for the results presented in Table 3 are very analogous to the Family C ENIIRA/SDAAS strains although some of these strains did not have the regulated delayed lysis in vivo phenotype.

The empty vector PIESV strains used for the results presented in Table 3 are very analogous to the Family C ENIIRA/SDAAS strains although some of these strains did not have the regulated delayed lysis in vivo phenotype.

4. Interaction of Family A and B Strains with HEK Cells Displaying TLR and Nod Factors.

To evaluate the ability of *Salmonella* strains with differing genotypes to stimulate innate immune responses, we have used HEK293 cells with a NFκB-inducible secreted embryonic alkaline phosphatase (SEAP) reporter gene (Invivo-Gen) and displaying Nod1, Nod2 and TLR4. We initially determined that all three Family A, B and C strains containing a plasmid encoding GFP were highly invasive into HEK cells. The χ9052 and χ12499 strains were grown in LB broth to maximize expression of the SPI-1 invasion phenotype, sedimented at room temperature and suspended in tissue culture medium. HEK cells at $2 \times 10^5$ cells/ml were mixed with bacterial cells at a MOI of 10 in a volume of 200 μl in 96 well plates. Unattached bacteria were removed by washing in tissue culture medium and then plates were incubated at 37° C. in 5% $CO_2$ over 24 h with periodic scanning at 650 nm for production of the blue reagent due to secretion of alkaline phosphatase from the HEK cells. FIG. 2 presents the results. χ9052 was best at activating Nod1, whereas both strains activated Nod2 equal to or better than muramyl dipeptide (MDP). Both strains activated TLR4 better than LPS at all times measured.

5. Enhanced NFκB in HEK Cells Displaying TLR5.

S. *Typhimurium* χ9026 with ΔfljB217 ΔfliC180 mutations that overproduces a truncated FliC flagellin having the receptor for TLR5 stimulates significantly higher levels of IL6 and TNFα production in GALT and MLN cells than the non-flagellated χ9028 strain with ΔfljB217 ΔfliC2426 and also stimulates higher levels of NF-kB production in HEK cells displaying the murine TLR5. Expansion of the data in analyzing interaction of Sal-Adj/ENIIRA strains with HEK cells is presented in the Examples.

EXAMPLES

Example 1: Materials and Methods

Bacterial Strains, Media and Bacterial Growth.

All Sal-Adj/ENIIRA/SDAAS strains as well as other strains possessing individual mutations used in strain constructions are derived from the highly virulent S. *Typhimurium* UK-1 strain χ3761 (21). LB broth and agar (22) will be used as complex media for propagation and plating of *Salmonella* strains. Purple broth (PB) (Difco), which is devoid of arabinose (Ara), was also used since LB contains low levels of arabinose. MacConkey agar with 0.5% lactose (Lac) and 0.1% Ara were used to enumerate bacteria recovered from mice. *Mycobacterium tuberculosis* H37Rv was propagated in Middlebrook 7H9 broth (Difco) supplemented with 10% albumin, dextrose and sodium chloride (ADS). Middlebrook 7H11 agar, supplemented with 10% ADS was used to determine bacterial CFU titers in the lungs and spleens of immunized mice challenged with *M. tuberculosis*. Bacterial growth was monitored spectrophotometrically and by plating for colony counts. S. *Typhimurium* PIESV strain χ12068 carrying the plasmid pYA4891 was used in two of the experiments described in Example 5. χ12068 has the following genotype: (ΔP$_{murA25}$::TT araC P$_{araBAD}$ murA ΔasdA27::TT araC P$_{araBAD}$ c2 Δpmi-2426 Δ(wza-wcaM)-8 ΔrelA197::araC P$_{araBAD}$ lacI TT ΔrecF126 ΔsifA26 ΔwaaL46 ΔpagL12::TT araC P$_{araBAD}$ waaL), which has the regulated delayed lysis in vivo phenotype and escapes the SCV to lyse in the cytosol to deliver antigens to the proteosome for class I presentation to induce CD8+, CD17+ and NKT-dependent immune responses. The plasmid pYA4891 is designed for use in regulated delayed lysis in vivo PIESVs and is a derivative of pYA4589, described in FIG. 1. Plasmid pYA4891 carries genes encoding three *M. tuberculosis* antigens: Ag85A, ESAT-6 and CFP-10 (31). Ag85A is one of three highly conserved mycolyl transferases integral to the synthesis of mycolic acids, an essential component of the mycobacterial cell envelope. Antigens 85A, B and C transport mycolyl residues from the mycobacterial cytoplasm to the growing chains of mycolic acids (38). The antigens ESAT-6 and CFP-10 of *M. tuberculosis* are two secreted proteins that are important virulence factors and are two of the most protective antigens of *M. tuberculosis* (39-41). *M. tuberculosis* ESAT-6 and its homologue TB10.4 are components of two subunit vaccines against *M. tuberculosis* that have been shown to be protective in immunized mice (31,41) and guinea pigs (41) and are currently in Phase IIa human clinical trials (42). In χ12068 (pYA4891), Ag85A is exported from χ12068 via the *Salmonella* Type 2 secretion system during in vivo growth; ESAT-6 and CFP-10 are delivered from χ12068 by the *Salmonella* Type 3 secretion system directly into host cell cytoplasm during in vivo growth. All three antigens are delivered into the cytoplasm of host cells upon lysis of χ12068, following regulated delayed lysis.

Molecular and Genetic Procedures

Methods for DNA isolation, restriction enzyme digestion, DNA cloning and use of PCR and real-time PCR for construction and verification of bacterial strains and vectors are standard (23). Defined deletion mutations with and without specific insertions have been constructed for all mutations listed in Table 1 using flanking sequences derived from the S. *Typhimurium* parent χ3761. These mutations are introduced using either phage P22HTint (24, 25) transduction of suicide vectors integrated into the deletion mutation followed by selection for sucrose resistance (26) or by conjugational transfer of suicide vectors using standard methods (27, 28) with the suicide vector donor strains χ7213 and χ7378 (29). Plasmid constructs were evaluated by DNA sequencing and for ability of sugar-regulated sequences to specify synthesis of proteins using gel electrophoresis and western blot analyses (30).

Strain Characterization

Sal-Adj/ENIIRA/SDAAS strains were fully characterized at each step in their construction. Genetic attributes were confirmed by PCR with appropriate primers. Measurement of LPS core and O-antigen were performed after electrophoresis using silver-stained gels (88). This analysis is done after every step in any strain construction to eliminate possible spontaneous variants if they arise. We also validate the complete sensitivity of all Sal-Adj/ENIIRA/SDAAS strains to all antibiotics that might ever be used to treat *Salmonella* infections. Metabolic attributes are evaluated using API-20E tests. The presence of the recA mutation is determined by inability to undergo recombination using P22 transduction and extreme sensitivity to UV light.

Swimming motility was assessed on LB plates solidified with 0.3% agar and supplemented with appropriate supplements (arabinose or DAP or D-alanine). Strains were grown statically overnight in the appropriate media. The next day, 50 μl of this culture was inoculated into 2 ml of the appropriate media and grown with aeration at 37° C. to an optical density at 600 nm (OD600) of 0.8 to 0.85. One milliliter samples of cultures were pelleted at 4,500×g and were resuspended in 1 ml BSG. Five microliter samples of bacterial suspension were spotted onto the middle of the plates, which were then incubated at 37° C. for 7 h.

Production and secretion of flagellin was determined by shearing appendages from cells in culture using a Waring blender. After removal of cells by centrifugation, proteins in the supernatant were precipitated with TCA and then hydrolyzed by boiling in SDS buffer prior to electrophoresis. Antiserum against FliC and FljB flagellin were used to detect production of the Phase I and Phase II flagellins, respectively, by western blotting.

Production of fimbrial adhesins is determined using antisera to the Saf and Stc fimbrial subunits by western blot analyses after electrophoresis of precipitated protein fractions obtained after shearing bacterial strains in a blender to remove flagellar and fimbrial appendages (as described above).

Measurement of growth and lysis after inoculation of bacteria into media not permissive for growth was evaluated spectrophotometry and by dilution and plate counting to determine viable cell titers. For these evaluations we used Purple broth since it totally lacks the sugars arabinose, mannose and rhamnose that are present at very low concentrations in LB broth. We also use un-Purple broth that just lacked the pH indicator dye. In some studies, we also used MOPS minimal media with and without supplements DAP, D-alanine, arabinose and/or rhamnose. Bacterial strains were grown statically overnight in the appropriate media supplemented with 0.1% arabinose and/or 50 μg DAP and/or 20 μg D-alanine. The next day, 50 μl of this culture was inoculated into 2 ml of the appropriate media and grown with aeration at 37° C. to an optical density at 600 nm (OD600) of 0.8 to 0.85. Cells were then centrifuged twice and washed and resuspended in un-Purple broth at a cell density of about $5 \times 10^7$ CFU/ml and then grown with rotary aeration at 37° C. Absorbancies at $OD_{600\ nm}$ were monitored continuously and dilutions for plate counts on permissive agar medium made at 30 and/or 60 min intervals.

Cell Culture Methods and Use of HEK293 Cells to Monitor Initiation of Innate Immune Responses HEK293 cells with the murine TLR1, TLR2, TLR4, TLR4 MD2 CD14, TLR5, TLR5 CD14, TLR6, TLR8, TLR9, Nod1 and Nod2 were used with the NF-κB SEAP reporter system to enable read outs at A650 nm. Sal-Adj/ENIIRA/SDAAS strains were grown to maximize their invasiveness and determine bacterial cell attachment to, invasion into and survival in HEK cells and monitor stimulation of NF-κB production by HEK cells over a 24 h period. More specifically, Salmonella strains were grown in LB with appropriate supplements at 37° C. to an optical density at 600 nm (OD600) of 0.8 to 0.9. Bacteria were harvested by centrifugation at 4,500×g at room temperature and were resuspended in endotoxin free water at the densities required to produce the desired dose ENIIRA/SDAAS strain as multiplicity of infection (MOI 10, 1, 01 and 001) relative to HEK cell density in the appropriate volume. Bacterial samples of 20 μl were added per well in a flat-bottom 96-well cell culture plate.

HEK-Blue™ mTLR4 or HEK-Blue™ mTLR5 or HEK-Blue™ mNOD1 or HEK-Blue™ mNOD2 cells were purchased from InvivoGen, San Diego, CA, USA. The cells were cultured at 37° C. in 5% $CO_2$ in 25 vented flasks using Eagle's Minimum Essential Medium (EMEM) ATCC® 30-2003™ containing heat-inactivated fetal bovine serum (FBS), penicillin/streptomycin, and Normocin™ (Invivo-Gen). Cells were grown to 50-70% confluence and were resuspended in HEK-Blue detection media at a cell density $2\text{-}5 \times 10^6$ viable cells per milliliter. Cell suspensions of 180 μl were added to the previous bacterial samples added to the 96-well cell culture plate. Plates were incubated at 37° C. in 5% $CO_2$ for 24 h. SEAP activity was determined using a spectrophotometer at 650 nm. The response ratios were calculated by dividing the OD at 650 nm for the treated cells by the OD at 650 nm for the untreated cells.

Animal Experimentation to Monitor Safety and Efficacy of Sal-Adj/ENIIRA/SDAAS Constructs Administered by Different Routes to Young Adult Mice Ten-fold dilutions ($10^4\text{-}10^8$ CFU) of S. Typhimurium χ12517 or χ12518 strains were administered by intravenous (I.V.) or subcutaneous (S.C.) or intranasal (I.N.) routes to 6-week-old female BALB/c mice by following our standard procedures (49). Briefly, adjuvant strains were grown statically overnight in the appropriate media. The next day, 100 μl of each culture was inoculated into 5 ml of the appropriate media and grown with aeration at 37° C. to an optical density at 600 nm (OD600) of 0.8 to 0.85. Cultures were pelleted at 4,500×g at room temperature and were resuspended in BSG at the densities required to produce the desired dose in the appropriate volume. A volume of 20 μl of bacterial suspension containing the appropriate dose was inoculated by the various routes at day 0. Mice were monitored for death twice a day up to 3 weeks.

Animal Experimentation to Monitor Safety and Efficacy of Sal-Adj/ENIIRA/SDAAS Constructs to Augment Immune Responses to Ovalbumin (Ova)

Imject Alum was purchased from Thermo Scientific (cat #77161) and ova albumin was purchased from Sigma (A2512-1G). Ova albumin was dissolved in BSG with a stock concentration 2 mg/ml. Adjuvant strain χ9052 was grown statically overnight in LB supplemented with DAP and D-alanine. The next day, 100 μl of this culture was inoculated into 5 ml of the appropriate media and grown with aeration at 37° C. to an optical density at 600 nm (OD600) of 0.8 to 0.9. Bacteria were harvested by centrifugation at 4,500×g at room temperature and were resuspended in BSG at the densities required to produce the desired dose in the appropriate volume. Above suspension of 500 μl was emulsified with 500 μl Imject Alum by repeatedly passing through a syringe needle. Each mouse was inoculated subcutaneously with 100 μl of suspension. Six-week-old BALB/c mice were divided into three groups of five mice each named Group-I [Ova (100 μg)+χ9052 ($5 \times 10^6$)], Group-II [Ova (100 μg)] and Group-III [Ova (100 μg)+ Imject Alum (50 μl)]. Animals were immunized subcutaneously. Blood was sampled from immunized mice for antibody determination by ELISA at 2, 4 and 6 weeks postinoculations.

Animal Studies to Determine Ability of Sal-Adj/ENIIRA/SDAAS Constructs to Augment Level of Protective Immunity Against M. tuberculosis (Mtb) Challenge of BCG Immunized Mice C57/BL6 mice of both sexes were given a s.c. dose of $5 \times 10^6$ CFU of M. bovis BCG Pasteur (ATCC 35734) on day 0 without and with varying doses in CFU of different Sal-Adj constructs by s.c. ($1 \times 10^5$ CFU), i.n. ($1 \times 10^7$ CFU), and i.v. ($5 \times 10^4$ CFU) routes. On day 28, sera were collected from all mice. In addition, two mice from each group were euthanized, livers and spleens were removed, processed and used for flow cytometric analyses. On day 35 all mice were infected with aerosolized M. tuberculosis H37Rv (50 to 100 bacteria per mouse) using a Glas-Col Inhalation Instrument (31). Six weeks after challenge, mice were euthanized, lungs and spleens removed aseptically, tissues homogenized, homogenates diluted and samples plated on Middlebrook 7H11+10% ADS agar plates (Difco). Plates were incubated at 37° C. for 3-4 weeks to determine the Mtb CFU in these organs.

Monitoring Immune Responses

Antigen Preparation

Purified Ova was obtained commercially. *M. tuberculosis* antigens Ag85A, ESAT-6 and CFP-10 were purified as His-tagged proteins from recombinant *E. coli*. These antigens were used for immunoassays as described below.

ELISA

Serum antibodies were measured in blood collected by submandibular bleeding. We determined the concentrations of IgG and IgA against Ova in μg/ml and the concentrations of IgG against Ag85A, ESAT-6 and CFP-10 in μg/ml. To distinguish between Th1 and Th2 responses, we determined titers of IgG1 and IgG2a for Ova and titers of IgG1 and IgG2b for Ag85A, ESAT-6 and CFP-10. The 96-well plates were coated with 100 ng Ova or with 0.5 to 1 μg of each *M. tuberculosis* antigen. Free binding sites were blocked with the SEABLOCK Blocking Buffer (Thermo Fisher). Anti-Ova titers or anti-Ag85A, anti-ESAT-6 or anti-CFP-10 titers in the serum (dilution 1:100) were detected with biotinylated goat anti-mouse IgG, IgG1, IgG2a or IgA for Ova and biotinylated goat anti-mouse IgG, IgG1 or IgG2b for Ag85A, ESAT-6 and CFP-10 (Southern Biotechnology) followed by incubation with a streptavidin-alkaline phosphatase conjugate (Southern Biotechnology). Color development (absorbance at 405 nm) with p-nitrophenyl phosphate (Thermo Fisher Scientific) was recorded with an automated ELISA plate reader (EL311SX; Biotek). Unconjugated mouse antibodies (Southern Biotechnology) (IgG, 5 μg/ml to 40 ng/ml; IgG1, IgG2a or IgG2b, 1 μg/ml to 8 ng/ml; IgA 62.5 ng/ml to 0.46 ng/ml) were serially diluted and coated on a 96-well plate in duplicate. Standard curves were generated by plotting the OD405 values against the representative concentrations of the diluted unconjugated antibody solutions and fitted to a 4-parameter logistic curve (R2>0.98). The absorbance values of experimental samples were fit into the standard curve to interpolate antibody concentrations. All samples were analyzed in triplicate. We also used ELISPOT assays (32) in initial studies to determine whether antigen-specific IgA and IgG secreting peripheral blood lymphocytes are induced 10 to 15 days after vaccination with Ova and adjuvants.

Cellular Immune Responses and Flow Cytometry Analyses

These more detailed evaluations of immune responses induced have been and will be continually used as optimal Sal-Adj/SDAAS constructs are identified and their use evaluated with vaccine constructs and preparations to ultimately be tested.

Flow Cytometry

Flow cytometry was used to quantitate populations of antigen-specific CD4+ and CD8+ T cells and antigen-specific cytokine-secreting cells in the lungs and spleens of mice immunized with *M. bovis* BCG in combination with Sal-Adj/SDAAS constructs. Lymphocytes were isolated from homogenized lungs and spleens of immunized or PBS control mice by centrifugation of the cell lysates through Percoll gradients. After washing the purified lymphocytes with PBS, the cells were simulated with 10 μg/ml of purified protein antigens for 24 h. Fc blocking reagent was used to prevent non-specific binding of antibodies to Fc receptors on the lymphocytes. Surface staining using anti-mouse fluorophore-labelled antibodies (Biolegend), followed by fixation of the cells with 4% para-formaldehyde was used to identify subsets of lymphocytes. Gating on both CD4 and CD8 was done on the CD3+ lymphocyte population to detect the percent of antigen-specific CD4+ and CD8+ cells expressing effector KLRG1, PD1 or memory CD62L, CD127 molecules. To detect intracellular cytokines, lymphocytes were stained for surface markers CD3, CD44, CD4 and CD8, followed by treatment with BD Sciences Cytofix/Cytoperm and stained intracellularly with combinations of IFN-γ and TNF-α antibodies. All samples were analyzed in the Department of Infectious Diseases and Immunology Flow Cytometry Core Facility on an 8-color FACSCanto, 18-color FACSFortessa flow cytometer with a SH800Z Cell Sorter. Data analyses and statistical comparisons among the samples from immunized and non-immunized mice was done using the Flow JO software.

Splenomegaly.

To determine protection against challenge with *M. tuberculosis* H37Rv, the spleens and lungs are weighed individually after they are removed from the euthanized mice. The number of CFUs determined from plating samples of homogenized lungs and spleens are reported as CFU per gram of tissue. When spleens were removed from mice immunized with ENIIRA/SDAAS strains, it was immediately evident by visual observation, that some spleens were significantly enlarged, compared to the spleens of unimmunized mice or mice immunized with *M. bovis* BCG or mice immunized with PIESV χ12068 (pYA4891).

Statistical Analyses

All results were analyzed using the most appropriate statistical test from the SAS program to evaluate the relative significance or lack thereof of results obtained.

Example 2. Construction and Characterization of Sal-Adj/ENIIRA/SDAAS Strains a. Introduction Sal-Adj/ENIIRA/SDAAS strains of the starting genotypes for the Family A, B and C strains were initially compared to determine which most enhances induced immune responses to Ova and protective immunity to *M. tuberculosis* challenge. This was because it is possible that strains from different families will each be more efficacious in one evaluative test than the other. In these initial studies, the Family A and B strains were found to be most efficacious, in all probability since they invade efficiently and undergo lysis more rapidly. In accord with this, Family C strains that underwent regulated lysis in vivo more rapidly, induced higher innate immune responses than did Family C strains that underwent more cell divisions in vivo prior to lysis. These rates and numbers of cell divisions in vivo prior to commencement of lysis is regulated by altering levels of expression of genes for virulence attributes, synthesis of peptidoglycan precursors and repressors by modification of promoter, SD and start-codon sequences and/or by altering the spacing between these elements and/or by alterations in plasmid copy numbers. Based on these results we are continuing to develop improved Family C strains as the PIESV vector strains as vaccine constructs for protective antigen and DNA vaccine delivery to prevent infectious diseases. Since recruitment and induction of innate immunity initially upon vaccination would be most beneficial in augmenting induction of acquired immunity by a vaccine, we have focused on developing the Family A and B ENIIRA/SDAAS strains to serve as superior adjuvants because they invade host cells and lyse quickly to deliver PAMPs/MAMPs to quickly activate induced innate immune responses.

Comparative evaluation of the survival of Family A and B strains after growth in Purple broth with arabinose and

23

Figure 3:
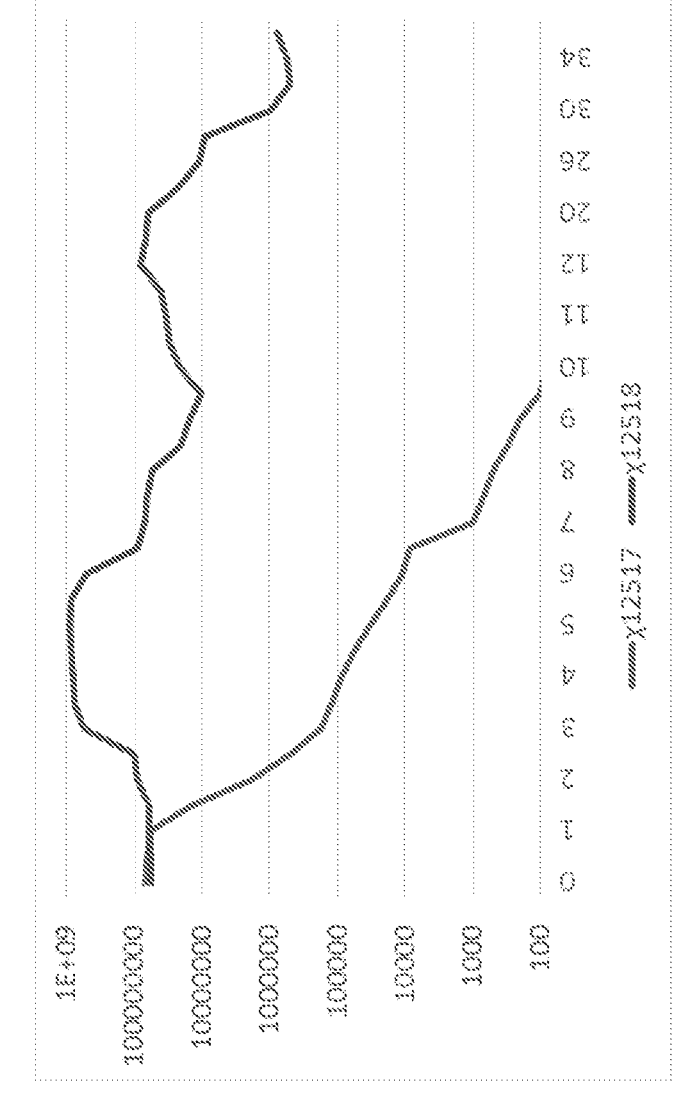

24 inoculation into medium without arabinose indicated rapid lysis and death of the Family A strain χ9052 whereas the Family B strain χ12499 increased in cell number for several cell divisions before lysis and death commenced (FIG. 3). These results were as expected and suggested that the Family A and B strains might be more efficacious in inducing innate immune responses due to this short-term proliferation in vivo prior to onset of lysis. While this could be beneficial, it was possible that the Family B strains might also be more inflammatory. These considerations thus guided the design of safe efficacious ENIIRA/SDAAS strains to recruit early onset innate immunity. Sal-Adj/ ENIIRA/SDAAS strains derived from the Family A and B strains were made with combinations of genetic modifications to enable determining which mutations were beneficial or were marginal in benefit. This then enabled us to further optimize and enhance induced innate immune responses. The phenotypic properties associated with each mutation in the strains constructed are presented in Table 1 and Table 2 lists the suicide vectors used to introduce the various mutations into the strains constructed.

b. Sal-Adj/ENIIRA/SDAAS Strains Constructed

Table 4 lists the strains constructed from the Family A strain χ9052. The properties associated with the mutations present are described in following sections.

TABLE 4

| Family A strain genotypes and derivations | | |
| --- | --- | --- |
| Chi number | Genotype | Parent |
| χ9052 | Δalr-3 ΔdadB4 ΔasdA33 | χ8901 |
| χ12503 | Δalr-3 ΔdadB4 ΔasdA33 ΔfliC180 | χ9052 |
| χ12512 | Δalr-3 ΔdadB4 ΔasdA33 ΔfliC180 ΔpagP81::$P_{lpp}$ lpxE | χ12503 |
| χ12515 | Δalr-3 ΔdadB4 ΔasdA33 ΔfliC180 ΔpagP81::$P_{lpp}$ lpxE ΔpagL7 | χ12512 |
| χ12517 | Δalr-3 ΔdadB4 ΔasdA33 ΔfliC180 ΔpagP81::$P_{lpp}$ lpxE ΔpagL7 ΔlpxR9 | χ12515 |
| χ12553 | Δalr-3 ΔdadB4 ΔasdA33 ΔfliC180 Δ(hin-fljBA)-219 | χ12503 |
| χ12554 | Δalr-3 ΔdadB4 ΔasdA33 ΔfliC180 ΔpagP81::$P_{lpp}$ lpxE ΔpagL7 ΔlpxR9 Δ(hin-fljBA)-219 | χ12517 |
| χ12555 | Δalr-3 ΔdadB4 ΔasdA33 ΔfliC180 ΔpagP81::$P_{lpp}$ lpxE ΔpagL7 ΔwaaC41 | χ12515 |
| χ12556 | Δalr-3 ΔdadB4 ΔasdA33 ΔfliC180 ΔpagP81::$P_{lpp}$ lpxE ΔpagL7 ΔwaaG42 | χ12515 |
| χ12557 | Δalr-3 ΔdadB4 ΔasdA33 ΔfliC180 ΔpagP81::$P_{lpp}$ lpxE ΔpagL7 ΔwaaL46 | χ12515 |
| χ12558 | Δalr-3 ΔdadB4 ΔasdA33 ΔfliC180 ΔpagP81::$P_{lpp}$ lpxE ΔpagL7 ΔlpxR9 ΔwaaC41 | χ12517 |
| χ12559 | Δalr-3 ΔdadB4 ΔasdA33 ΔfliC180 ΔpagP81::$P_{lpp}$ lpxE ΔpagL7 ΔlpxR9 ΔwaaG42 | χ12517 |
| χ12560 | Δalr-3 ΔdadB4 ΔasdA33 ΔfliC180 ΔpagP81::$P_{lpp}$ lpxE ΔpagL7 ΔlpxR9 ΔwaaL46 | χ12517 |

Table 5 lists the strains constructed from the Family 2 strain χ12499. The properties associated with the mutations present are described in following sections.

TABLE 5

| Family B strain genotypes and derivations | | |
| --- | --- | --- |
| Chi number | Genotype | Parent |
| χ12499 | Δ$P_{asdA55}$::TT araC $P_{BAD}$ asd Δalr-3 Δ$P_{dadB66}$::TT araC $P_{BAD}$ dadB | χ12498 |
| χ12504 | Δ$P_{asdA55}$::TT araC $P_{BAD}$ asd Δalr-3 Δ$P_{dadB66}$::TT araC $P_{BAD}$ dadB ΔfliC180 | χ12499 |
| χ12513 | Δ$P_{asdA55}$::TT araC $P_{BAD}$ asd Δalr-3 Δ$P_{dadB66}$::TT araC $P_{BAD}$ dadB ΔfliC180 ΔpagP81::$P_{lpp}$ lpxE | χ12504 |
| χ12516 | Δ$P_{asdA55}$::TT araC $P_{BAD}$ asd Δalr-3 Δ$P_{dadB66}$::TT araC $P_{BAD}$ dadB ΔfliC180 ΔpagP81::$P_{lpp}$ lpxE ΔpagL7 | χ12513 |
| χ12518 | Δ$P_{asdA55}$::TT araC $P_{BAD}$ asd Δalr-3 Δ$P_{dadB66}$::TT araC $P_{BAD}$ dadB ΔfliC180 ΔpagP81::$P_{lpp}$ lpxE ΔpagL7 ΔlpxR9 | χ12516 |
| χ12542 | Δ$P_{asdA55}$::TT araC $P_{BAD}$ asd Δalr-3 Δ$P_{dadB66}$::TT araC $P_{BAD}$ dadB ΔfliC180 ΔpagP81::$P_{lpp}$ lpxE ΔpagL7 ΔlpxR9 ΔwaaC41 | χ12518 |
| χ12543 | Δ$P_{asdA55}$::TT araC $P_{BAD}$ asd Δalr-3 Δ$P_{dadB66}$::TT araC $P_{BAD}$ dadB ΔfliC180 ΔpagP81::$P_{lpp}$ lpxE ΔpagL7 ΔlpxR9 ΔwaaG42 | χ12518 |
| χ12544 | Δ$P_{asdA55}$::TT araC $P_{BAD}$ asd Δalr-3 Δ$P_{dadB66}$::TT araC $P_{BAD}$ dadB ΔfliC180 ΔpagP81::$P_{lpp}$ lpxE ΔpagL7 ΔlpxR9 ΔwaaL46 | χ12518 |
| χ12545 | Δ$P_{asdA55}$::TT araC $P_{BAD}$ asd Δalr-3 Δ$P_{dadB66}$::TT araC $P_{BAD}$ dadB ΔfliC180 ΔwaaC41 | χ12504 |
| χ12546 | Δ$P_{asdA55}$::TT araC $P_{BAD}$ asd Δalr-3 Δ$P_{dadB66}$::TT araC $P_{BAD}$ dadB ΔfliC180 ΔwaaG42 | χ12504 |
| χ12547 | Δ$P_{asdA55}$::TT araC $P_{BAD}$ asd Δalr-3 Δ$P_{dadB66}$::TT araC $P_{BAD}$ dadB ΔfliC180 Δ(hin fljBA)-219 | χ12504 |
| χ12548 | Δ$P_{asdA55}$::TT araC $P_{BAD}$ asd Δalr-3 Δ$P_{dadB66}$::TT araC $P_{BAD}$ dadB ΔfliC180 ΔpagP81::$P_{lpp}$ lpxE ΔpagL7 ΔlpxR9 Δ(hin fljBA)-219 | χ12518 |

TABLE 5-continued

| | Family B strain genotypes and derivations | |
|---|---|---|
| Chi number | Genotype | Parent |
| χ12549 | ΔP$_{asdA55}$::TT araC P$_{BAD}$ asd Δalr-3 ΔP$_{dadB66}$::TT araC P$_{BAD}$ dadB ΔfliC180 ΔwaaL46 | χ12504 | c. Construction of Strains with Alterations in LPS Structure

S. *Typhimurium* is a gram-negative bacterium that contains LPS in its outer membrane. One vital component of LPS is lipid A that has a repeating disaccharide with six attached lipid acyl chains. Lipid A constitutes the potent endotoxin that can cause sepsis and death. The level of sensitivity to this endotoxin varies considerably among animal species with cattle, horses, dogs and humans being far more sensitive than chickens and even mice (34). It is also the lipid A that interacts as an agonist with TLR4 to recruit an innate immune response. However, *Salmonella* has evolved as a successful pathogen so as to infect more successfully by reducing the ability of its lipid A to trigger innate immunity by modifications that reduce the agonist activity of its lipid A. This is accomplished by decorating the lipid acyl chains with small molecules. Since lysis of ENIIRA/SDAAS strains immediately release the LPS with the lipid A endotoxin, we constructed strains χ12717 (Family A) and χ12518 (Family B) with the ΔpagP81::P$_{lpp}$ lpxE deletion-insertion mutation so that the strain synthesizes the non-toxic adjuvant mono-phosphoryl lipid A rather than the toxic lipid A while retaining its ability to activate TLR4 via the MD2 (rather than MyD88) pathway (33). Inactivation of the pagP gene is important since its gene product modifies lipid A to reduce its agonist activity. The promoter from the *E. coli* lipoprotein gene (lpp) is one of the strongest promoters since the lipoprotein synthesized is the most abundant protein in gram negative bacteria. It is used here to drive the constitutive expression of the lpxE gene from *Francisella tularensis* that eliminates a 4' phosphate decoration of the lipid A disaccharide that is responsible for endotoxicity. This alteration thus precludes excess inflammation due to release of endotoxin in vivo although release of other cell constituents in Family B strains that undergo several cell divisions in vivo prior to onset of lysis might still be too inflammatory at high doses.

We therefore evaluated the relative attenuation/virulence of these two strains in mice by delivery of doses of $10^4$, $10^5$, $10^6$ and $10^7$ CFU by the i.v. route, doses of $10^5$, $10^6$, $10^7$ and $10^8$ CFU by the i.n, and s.c. routes, and $10^9$ CFU by the oral route. All mice survived challenge at all doses by all routes when infected with the Family A strain χ12517. However, some mice died when infected with the Family B strain χ12518 at doses above $10^6$ CFU by the i.v, and i.n. routes and above $10^7$ CFU by the s.c. route, while all mice survived oral inoculation. These results indicated that the several cell divisions in vivo of the Family B strains, due to the regulated delayed lysis in vivo attribute would necessitate animal studies using lower doses and ultimately for the need to introduce additional mutations to preclude excess inflammatory responses leading to mortality.

The ΔpagL7 and ΔlpxR9 mutations were also included to eliminate two additional means that *Salmonella* uses to lessen recruitment of innate immunity by reducing the agonist activity of lipid A (15). The benefits of these two mutations to enhancing TLR4 recruitment is demonstrated below in studies with HEK cells displaying the TLR 4 ligand. The eptA and arnT mutations (Table 1) have also been included in some ENIIRA/SDAAS strains as they also encode enzymes that lessen the agonist activity of lipid A.

Since some of the Family B derived strains administered at high doses by parenteral routes (i.v., s.c.) were too inflammatory, we constructed strains with deletion mutations in the waaC, waaG and waaL genes that eliminate synthesis of the middle LPS core, outer LPS core and LPS O-antigen, respectively, to confer complete attenuation. Since the waaC and waaG mutations reduce synthesis and display of flagella and might possibly reduce secretion of flagellin that is important for recruiting innate immunity via interaction with TLR5, the use of strains with the waaL mutation is preferred. Subsequently, we evaluated SDAAS strains such as χ12626 and χ12649 with the ΔwbaP45 mutation as a different means to block coupling of the LPS O-antigen to the LPS core.

d. Construction of Strains with Alterations in Flagella and Flagellin Release

A non-flagellated strain χ9028 with the ΔfliC2426 and ΔfljB217 mutations and strain χ9026 in which the ΔfliC2426 mutation is replaced with the ΔfliC180 mutation to result in synthesis and release of a truncated flagellin that activates TLR5 (see Overview/Preliminary studies) were used in initial evaluations. We initially constructed Family A and B strains with the ΔfliC180 mutation since initial results showed that this mutation enhanced production and release of the FliC flagellin that activates TLR5. In addition, the phase-lock mutation Δ(hin-fljBA)-219 was introduced so that the FliC protein is made by all Sal-Adj/ENIIRA/SDAAS cells. The fljB mutation eliminates the ability of these strains to synthesize the Phase II flagellin and the fljA mutation eliminates synthesis of the repressor that would block transcription of the fliC gene that specifies the Phase I flagellin. A further enhancement in flagellin production was achieved, in one embodiment, by introducing another mutation (cfs) that causes constitutive high-level flagellin synthesis.

Figure 4:
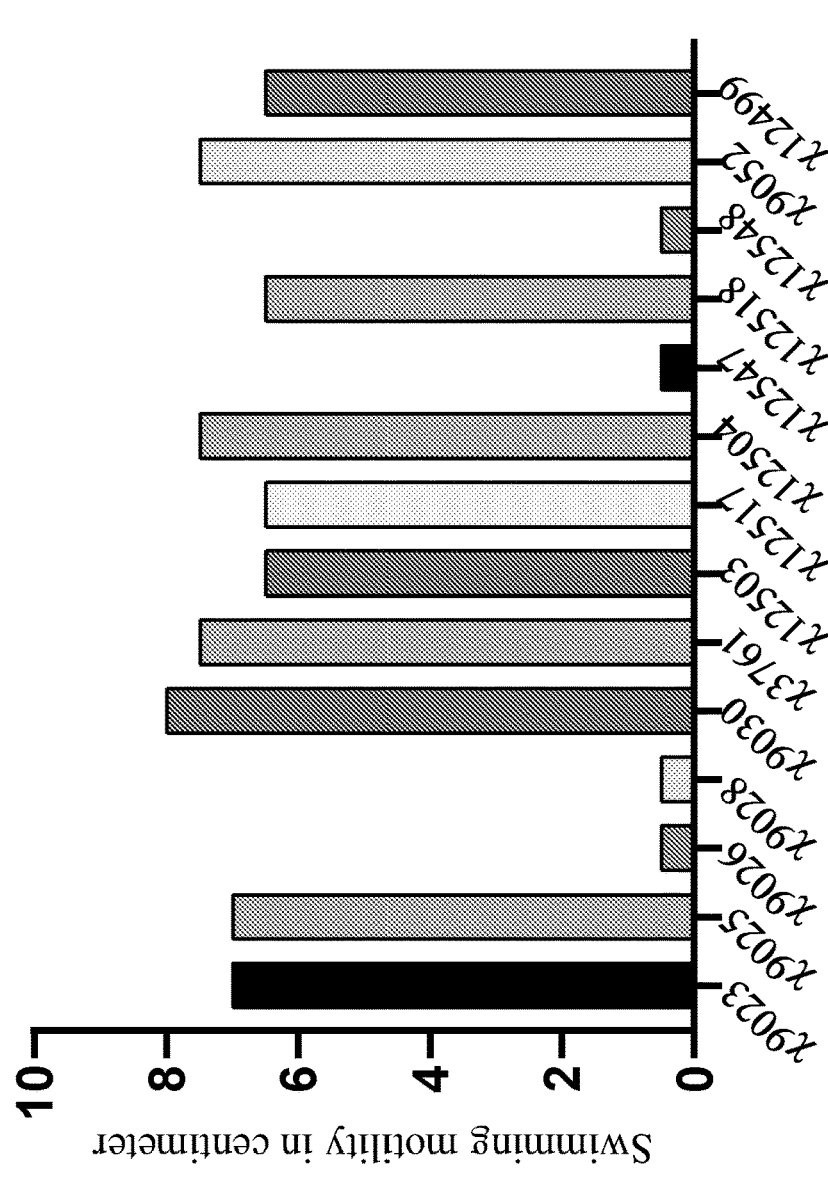

As shown in FIG. 4, strains with the ΔfliC180 mutation still display motility if they have a wild-type fljB gene but are unable to exhibit motility when a fljB mutation is present, which is achieved by inclusion of the phase-lock mutation Δ(hin-fljBA)-219 that we introduced into many Family A and B strains. Nevertheless, all strains with the ΔfliC180 mutation produce secreted flagellin as revealed by western blotting but this flagellin is unable to assemble into functional flagella to convey motility to cells.

e. Construction of Strains with Alterations in Display of Fimbriae

*S. typhimurium* has 12 operons that specify synthesis of fimbriae (18) and most of these are subject to regulation such that they are only synthesized in certain environments. We recently identified four fimbrial operons using the IVET system to identify in vivo expressed genes that are synthesized in the spleen after oral infection whereas the other eight fimbrial operons were not expressed (18). It was also determined that constitutive synthesis of the in vivo-synthesized Saf and Stc fimbriae significantly enhanced induction of protective immunity of a RASV/PIESV strain (18). Strains will therefore be evaluated for interaction with HEK cells and enhancing Ova immune responses lacking the other fimbrial operons expressed in vivo with either the deletion-insertion mutation $\Delta P_{ste53}::P_{murA}$ stc or $\Delta P_{saf55}::P_{murA}$ saf to cause constitutive synthesis of Ste or Saf fimbriae.

f. Other Constructions

In the initial comparison of the Family A, B and C parental lysis strains, derivatives were compared with the $\Delta$sifA26 mutation that eliminates a means of immunosuppression and enables S. *Typhimurium* cells to escape from the *Salmonella*-containing vesicle (SCV) such that lysis can occur in the cytosol. In RASV/PIESV strains that undergo regulated delayed lysis in vivo, escape from the SCV enables lysis of some vaccine cells to occur in the cytosol for delivery of protective antigens to the proteosome for Class I presentation and enhanced induction of CD8-dependent cellular immunity. Although individual cells of ENIIRA/SDAAS strains with the regulated delayed in vivo lysis attribute, can lyse prior to invasion into host cells or after invasion into cells whether contained in the SCV or after escape from the SCV (due to a $\Delta$sifA mutation) or after escape from a host cell undergoing pyroptosis, such lysis will release peptidoglycan components, RNA and DNA. Since peptidoglycan components activate Nod1 and Nod2, released RNA can activate TLR8 and CpG containing DNA sequences activate TLR9, the location of the release of these components will impact the level of activation of Nod1, Nod2, TLR8 and TLR9 that are located internally in host cells. On average, ENIIRA/SDAAS strains with the $\Delta$sifA26 mutation would therefore be expected to better activate Nod1, Nod2, TLR8 and TLR9.

The recA mutation blocks genetic recombination but about 10 percent of cells at each cell division undergo Rec-less cell death since occasional recombination between replicating chromosomes leads to rapid unregulated degradation of DNA. Consequentially, ENIIRA/SDAAS strains with recA mutations should be more efficient in liberating DNA fragments containing CpG sequences to activate TLR9. An additional benefit is that recA mutants of S. *Typhimurium* are totally avirulent and do not induce disease symptoms when administered to animal hosts. We have therefore inserted the $\Delta$recA62 mutation into candidate ENIIRA/SDAAS strains.

Some *Salmonella* pathogenicity island (SPI) 2 genes are effectors that can dampen induction of innate immune responses. The steE gene seems to be in this category such that ENIIRA strains unable to synthesize the steE gene product are investigated for impact on induction of innate immune responses using the HEK cell lines.

g. Characterization of Constructed ENIIRA/SDAAS Strains

All constructed ENIIRA/SDAAS strains are evaluated for the correctness of the introduced mutations and the phenotypes expected are confirmed using all the methods described in Example 1. In this regard, Family A strains such as χ12517 commence to lyse as they attempt to grow in any medium lacking DAP and D-alanine such that cultures completely lyse within several hours after transfer from a permissive growth medium to a non-permissive growth condition in the absence of DAP and D-alanine (FIG. 3). Family B strains, however, will undergo several cell divisions after transfer to non-permissive media since the enzymes for synthesis of DAP and D-alanine that cease to be synthesized are diluted by half at each cell division until their concentration is insufficient to enable synthesis of sufficient DAP and D-alanine to enable peptidoglycan synthesis. This behavior is observed for χ12518 (FIG. 3) during the first several hours of growth under non-permissive growth conditions. However, for cultures tested under high cell density lysis leads to destruction of the peptidoglycan cell wall layer to release its constituents DAP and D-alanine that are now free to be incorporated into peptidoglycan in surviving cells to cause an increase in viable cell titer. If, however, cultures of χ12518 are inoculated into non-permissive growth conditions at densities of $1 \times 10^5$ CFU or lower, death by lysis continues until the culture is devoid of viable cells.

h. Discussion

As each of the Sal-Adj/ENIIRA/SDAAS strains described above is constructed its properties are being fully validated. The abilities of these strains in comparison to parent and control strains to stimulate NF-κB production in HEK cells having different TLR and Nod factors were evaluated (Example 3). These results also led to synthesis of strains with combinations of mutations and the conduct of animal studies to determine which combination of mutations yields a Sal-Adj/ENIIRA/SDAAS strain(s) with greatest ability to enhance immune responses to Ova (Example 4) and protection against Mtb (Example 5).

Example 3. Evaluation of Sal-Adj/ENIIRA/SDAAS Strains to Activate Synthesis of NF-kB Production in HEK293 Cells Strains constructed in the Example 2 research were initially tested and compared for their ability to interact with and stimulate HEK293 cells with TLR1, TLR2, TLR4 (two types), TLR5 (two types), TLR6, TLR9, Nod1 and Nod2 using methods described in Example 1 M&M. Most evaluations have been with Family A strains since they commence to lyse immediately upon placing in non-permissive conditions in the absence of arabinose (see FIG. 3 above) such that lysis would occur during and after invasion of cells. In this regard, Family B strains are able to undergo several cell divisions after placing in non-permissive conditions in the absence of arabinose such that they will not be lysing after adding to HEK cells. This is because *Salmonella* cell division in infected cells ranges from 8 to more than 20 hours depending on cell type compared to less than an hour for most in vitro growth conditions. These inferences are validated by the results presented in FIG. 2 above in which the Family A strain χ9052 is more active in recruiting a response in HEK cells with the internal Nod1 receptor than is the Family B strain χ12499 (See FIG. 2B).

Results observed in evaluation of several Family A and Family B strains in assays of NFκB recruitment in HEK cells displaying TLR4 are presented in FIG. 5. In these studies, we varied the multiplicity of infection (MOI) of ENIIRA strains to HEK cells from 0.001:1 to 10:1. Based on these and other evaluations, Family B strains such as χ12518 were better recruiters than Family A strains such as χ12517. In addition, removal of the O-antigen or parts of the LPS core further enhanced recruitment of NFκB (compare χ12518 versus χ12542 and χ12543. All ENIIRA/SDAAS strains were more active in TLR4 activation than the wild-type parent χ3761.

Figure 6:
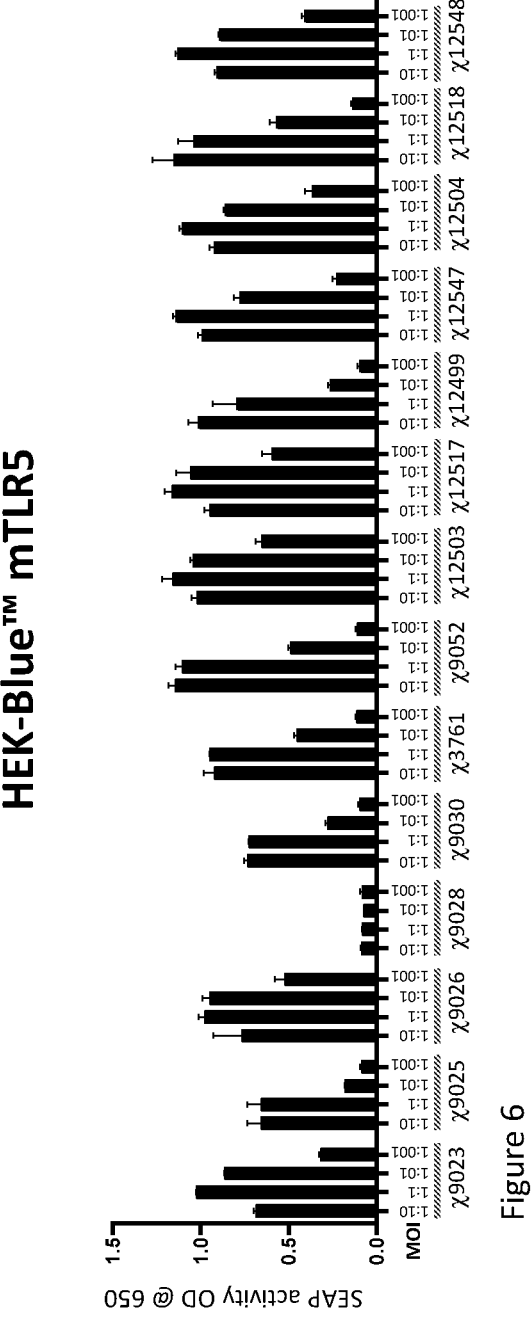

Results observed in evaluation of several Family A and Family B strains in assays of NFκB recruitment in HEK cells displaying TLR5 are presented in FIG. 6. We also include data for control strains in FIG. 6 that evaluate mutant strains derived from the wild-type parent strain χ3761. The only strain unable to activate TLR5 is χ9028 that is unable to synthesize flagellin or flagella due to the ΔfliC2426 and ΔfljB217 mutations. Thus, all the strains with the ΔfliC180 mutation activate TLR5 even though many are non-motile due to the fljB deletion mutation.

As noted above in reference to the FIG. 2 data, Family A strains are better at activating Nod1 than are Family B strains due to their more rapid lysis after entry into cells. Nevertheless, Family B strains with either ΔwaaC41 or ΔwaaG42 with or without the ΔpagP81::P$_{lpp}$ lpxE deletion-insertion mutation are proficient in activating Nod1 and Nod2 (FIG. 7). This unexpected result may be due to the sensitivity of strains lacking the LPS O-antigen and especially parts of the outer LPS core polysaccharide since they are very sensitive to complement-mediated cytotoxicity and other host natural defense barriers such as acidification and production of defensins.

Example 4. Evaluation of Sal-Adj/ENIIRA/SDAAS Strains by s.c., i.n, and Oral Routes with s.c. Administration of Ova Suspended in Buffered Saline or Alum and Monitoring Antibody Responses to Ova Because of total avirulence, we concentrated on testing the adjuvant activity of the Family A parental strain χ9052. The results presented in FIG. 8 reveal very clearly that co-administration of the ENIIRA strain with Ova was far superior to administering Ova with the standard Alum adjuvant in eliciting serum IgG antibodies against Ova. Studies with Family B strains such as with the avirulent derivative χ12544 (Table 5) have just commenced with the expectation that they will likely be better than Family A strains in these assays measuring enhanced antibody production to subunit vaccines. In this regard, because of the ability of Family B strains to undergo several rounds of cell division in vivo prior to lysis, we expect them to be effective at lower doses that needed for Family A strains

Example 5. Evaluation of the Ability of ENIIRA/SDAAS Strains to Augment Ability of BCG to Diminish Infection of Mice with M. tuberculosis H37RV (Mtb) and Whether Also Enhances the Ability of a PIESV Construct Delivering Mtb Protective Antigens to Further Protect Against Mtb Infection and Proliferation Three experiments have been conducted in which ENIIRA/SDAAS strains have been administered in combination with M. bovis BCG, which is currently the only vaccine approved for human use to prevent infections by M. tuberculosis and development of TB. In all of these experiments, BCG was administered s.c. with 5×10⁴ CFU of BCG, either alone or in combination with ENIIRA/SDAAS strains and/or the PIESV χ12068 (pYA4891). All immunizations/inoculations were given once. All experiments included a group of mice that were administered 100 µl of phosphate-buffered saline PBS on Day 0; these were unimmunized control mice. Thirty-five days after immunization, all mice were challenged with a low-dose aerosol of virulent M. tuberculosis H37Rv, such that each mouse received 50-100 bacteria per lung. On day 28 in Experiments 15 and 20 (FIGS. 10 and 11), blood was collected from all mice to determine antibody titers to the mycobacterial Antigen 85A, which is produced by both BCG and M. tuberculosis. In Experiments 15 and 20, two mice from each group were euthanized on day 28, their lungs and spleens homogenized and processed for flow cytometry, to evaluate T-cell responses to Ag85A and, in Experiment 20, to two M. tuberculosis antigens (ESAT-6 and CFP-10) produced by the PIESV χ12068 (pYA4891) construct. Approximately 6 weeks after challenge, mice were euthanized, lungs and spleens were removed, homogenized and plated for CFU determinations.

In Experiment 14 (FIG. 9), the ENIIRA/SDAAS strain was χ12499 (Family B) (ΔP$_{asdA55}$::TT araC P$_{BAD}$ asd Δalr-3 ΔP$_{dadB66}$::TT araC P$_{BAD}$ dadB), which was administered by itself or in combination with BCG by either s.c. administration of 1×10⁵ CFU of χ12499 or by i.v. administration of 1×10⁴ CFU of χ12499. Only M. tuberculosis CFU determinations were done in this experiment and we found that mice that had been immunized with the combination of BCG+χ12499 administered i.v. had CFUs of approximately 2×10⁴ in their spleens, compared to titers of 1×10⁵ CFU in the spleens of mice immunized with BCG alone and titers of 3×10⁵ CFU in the spleens of the unimmunized control mice, suggesting that administration of χ12499 by the i.v. route enhanced the protection afforded by BCG (FIG. 9). In the lungs of these mice, co-administration of χ12499 (i.v.) with BCG yielded CFU titers that were lower than the unimmunized control mice (5×10⁵ for immunized mice compared to 2×10⁶ CFU for unimmunized mice), but were not as low as mice immunized with BCG alone (4×10⁵ CFU).

In Experiment 15 (FIG. 10), co-administration of BCG with two ENIIRA/SDAAS strains (χ12517 (Family A) (Δalr-3 ΔdadB4 ΔasdA33 ΔfliC180 ΔpagP81::P$_{lpp}$ lpxE ΔpagL7 ΔlpxR9) and χ12518 (Family B) (ΔP$_{asdA55}$::TT araC P$_{araBAD}$ asd Δalr-3 ΔP$_{dadB66}$::TT araC P$_{BAD}$ dadB ΔfliC180 ΔpagP81::P$_{lpp}$ lpxE ΔpagL7 ΔlpxR9)), both delivered by i.v. (5×10⁴ CFU) or the PIESV χ12068 (pYA4891) (ΔP$_{murA25}$::TT araC P$_{araBAD}$ murA ΔasdA27::TT araC P$_{araBAD}$ c2 Δ(wza-wcaM)-8 Δpmi-2426 ΔrelA197::araC P$_{araBAD}$ lacI TT ΔrecF126 ΔsifA26 ΔwaaL46 ΔpagL12::TT araC P$_{araBAD}$ waaL+M. tuberculosis antigens Ag85A, ESAT-6 and CFP-10)), delivered by i.v. (5×10⁴ CFU) was evaluated. In this experiment, the CFU titers of M. tuberculosis in the lungs of mice immunized with the combination of BCG+χ12068 (pYA4891) were 5.5×10⁴ CFU, compared to titers of 2×10⁵ CFU in BCG-immunized mice and 2×10⁶ CFU in unimmunized control mice. Mice immunized with BCG+χ12517 or BCG+χ12518 had titers that were the same as mice immunized with BCG alone (2×10⁵ CFU). In the spleens of the mice in this experiment (FIG. 10), the titers of M. tuberculosis in mice immunized with the combination of BCG+χ12518 were 1.5×10³ CFU, compared to titers of 4×10⁴ CFU in mice immunized with BCG+χ12068 (pYA4891) and approximately 6×10⁴ CFU in mice immunized with BCG alone or BCG+χ12517. The titers in the unimmunized control mice were 2.5×10⁵ CFU. Flow cytometry analyses of the percentage of total T cells and dendritic cells (DCs) secreting Interferon-γ (IFN-γ) in response to Ag85A indicated that the highest percentage of IFN-γ-secreting T cells and DCs were from the spleens of mice immunized with BCG+χ12518, although all immunized mice had higher percentages of IFN-γ-secreting T cells and DCs in their spleens than the unimmunized control mice.

In Experiment 20 (FIG. 11), we repeated the comparisons of mice immunized with BCG+χ12068 (pYA4891), delivered i.v., and BCG+χ12518, delivered i.v., compared to mice immunized with BCG alone and to unimmunized mice. We also compared mice immunized with BCG+χ12068 (pYA4891)+χ12518, both delivered by i.v. injection of a total of 5×10⁴ CFU and mice immunized with BCG+χ12068 (pYA4891), delivered by intranasal (i.n.) administration of 1×10⁵ CFU, plus χ12518 delivered by i.v. injection (5×10⁴

CFU). (The titers of *M. tuberculosis* in the spleens of the mice from this experiment are provided in Example 8.) FIG. 11 shows the CFU titers of *M. tuberculosis* H37Rv in the lungs. Mice vaccinated with BCG alone or BCG+χ12068 (pYA4891) had titers that were more than one log lower than the CFU titers in the unimmunized mice. Mice immunized with the combination of BCG+χ12068 (pYA4891)+χ12518 (both delivered i.v.) had titers that were two logs lower than the titers in the unimmunized mice. Mice that were immunized with the combination of BCG+χ12518 or BCG+ χ12068 (pYA4891) (delivered i.n.)+χ12518 (delivered i.v) also had significantly lower CFU titers in their lungs, compared to unimmunized mice. These collective results were most surprising since the highly significant enhancement of the efficacy of BCG in reducing Mtb multiplication has never been previously observed. Thus, the ability of ENIIRA/SDAAS strains to enhance the effectiveness of BCG vaccination could have a profound global benefit in prevention of *M. tuberculosis* infections. This is highly significant since tuberculosis is now the number one cause of global deaths from any infectious disease. We have determined total IgG antibody responses in the sera of these mice to Ag85A, ESAT-6 and CFP-10. We found that IgG levels to Ag85A were higher in mice immunized with combinations of BCG and an ENIIRA/SDAAS strain or PIESV χ12068 (pYA4891), compared to mice immunized with BCG alone, with the highest levels in mice immunized with BCG+χ12068 (pYA4891)+χ12518, regardless of whether χ12068 (pYA4891) was delivered by i.v. or by i.n. inoculation. We also found that mice immunized with BCG+ χ12068 (pYA4891), delivered i.n., +χ12518 had the highest levels of total IgG against ESAT-6 and CFP-10. We also conducted flow cytometric analyses on the spleens and lungs of mice in this experiment. In the spleens, mice immunized with the combination of BCG+χ12068 (pYA4891) delivered i.n.+χ12518 had the highest percentages of IFN-γ-secreting CD4$^+$ T cells responding to ESAT-6, compared to mice in each of the other groups. Mice immunized with that combination also had the highest percentages of IFN-γ-secreting CD8$^+$ T cells responding to Ag85A, ESAT-6 and CFP-10. In the lungs of these mice, immunization with the combination of BCG+χ12068 (pYA4891) delivered i.n.+χ12518 induced the highest or close to highest levels of IFN-γ-secreting CD8$^+$ T cells in response to Ag85A, ESAT-6 or CFP-10 among all of the groups of immunized mice. In both lungs and spleens, mice immunized with the combinations of BCG+χ12518 strains or BCG+χ12068 (pYA4891) or BCG+ χ12518+χ12068 (pYA4891) all induced higher percentages of IFN-γ-secreting CD4$^+$ and CD8$^+$ T cells than mice immunized with BCG alone.

The results from the three experiments described above demonstrate that co-administration of BCG with ENIIRA/ SDAAS strains plus χ12068 (pYA4891) enhances the ability of BCG to protect mice against aerosol challenge with *M. tuberculosis* and that co-administration enhances both antibody and T-cell responses that is likely to contribute to protection against challenge. If found to be true in humans, the impact will be highly significant.

Splenomegaly: In experiments in which mice were immunized subcutaneously with *M. bovis* BCG alone or in combination with ENIIRA/SDAAS strains or the PIESV χ12068 (pYA4891) or both an ENIIRA strain and χ12068 (pYA4891), splenomegaly was observed in mice immunized with BCG and an ENIIRA strain. In Experiment 14, where the ENIIRA strain was χ12499 (Family B), 2 out of 9 mice immunized with χ12499 (delivered s.c.) alone, 2 out of 10 mice immunized with the combination of BCG+χ12499

(both delivered s.c) and 7 out of 8 mice immunized with the combination of BCG (delivered s.c.)+χ12499 (delivered i.v.) had significantly enlarged spleens, compared to the spleens of control mice (PBS administered s.c) and mice immunized with BCG alone, in which none of the mice had enlarged spleens. In Experiment 15, in which mice were immunized with BCG alone (delivered s.c.) or BCG (delivered s.c.) in combination with the PIESV χ12068 (pYA4891) or Family A ENIIRA strain χ12517 or Family B ENIIRA strain χ12518 (each administered i.v), only mice immunized with the combination of BCG+χ12518 had enlarged spleens. In Experiment 20, mice were immunized with BCG alone (delivered s.c.) and in combination with the PIESV χ12068 (pYA4891), delivered i.v., the Family B ENIIRA strain χ12518 (delivered i.v.), χ12068 (pYA4891) and χ12518 (both delivered i.v.) or χ12068 (pYA4891), delivered intranasally, and χ12518, delivered i.v. All groups of mice immunized with χ12518 (which was always administered i.v.) had mice with enlarged spleens. At present, we do not know why some mice in these three experiments developed enlarged spleens.

However, these results are in accord with other observations that indicate that the Family B strain χ12518 (ΔP$_{asdA55}$::TT araC P$_{BAD}$ asd Δalr-3 ΔP$_{dadB66}$::TT araC P$_{BAD}$ dadB ΔfliC180 ΔpagP81::P$_{lpp}$ lpxE ΔpagL7 ΔlpxR9) is possibly too inflammatory because it multiplies too many cell divisions prior to lysis. Although this can be addressed by using lower doses, we are now testing the benefits of including the ΔwaaL46 (χ12544), ΔwbaP45 and with or without ΔsifA26 and/or ΔrecA62 mutations on ensuring complete attenuation while retaining and even augmenting the beneficial adjuvant activities.

Example 6. Modification of ENIIRA/SDAAS Strains to Display PAMPS/MAMPs that Activate Innate Immune Receptors Displayed by Diverse Bacterial, Viral, Fungal and Parasite Pathogens Our group has displayed capsular polysaccharides specified by genes from gram-negative and gram-positive bacterial species on the surface of *Salmonella* strains. We have also expressed lipo-proteins and protein appendages encoded by genes from diverse pathogens. In addition, since the ENIIRA/SDAAS strains are designed to lyse, they can liberate plasmids engineered to display single-stranded and double-stranded RNAs as displayed by and serving as PAMPS for RNA viruses and for RNA released by living pathogenic microbes. It is thus possible to modify ENIIRA strains to induce innate immune responses that could differ and be more appropriate and efficacious in enhancing immunity to be induced by a diversity of vaccines targeting prevention of infection by diverse bacterial, viral, fungal and parasite pathogens.

Example 7. Non-Specific Protection Against Infection by Other Pathogens

It has been found that administration of the Sal-Adj/ ENIIRA/SDAAS constructs induces low-level protective immunity to challenge of unvaccinated animals to various bacterial, viral and parasite pathogens as revealed by the data in Table 3 in which the empty vector PIESV strains are representative of Family C ENIIRA strains. These results are impactful in the protection, in some examples, of military personnel and civilians against a biothreat as well as to contend with epidemics. These ENIIRA strains will also have utility in augmenting levels of protective immunity of subunit and killed vaccines and even of attenuated vaccines that do not induce robust protective immunity of long duration, such as BCG (see Example 5). It can also be expected that the level of innate immunity induced by administering ENIIRA strains will be of reasonably long duration. In fact, these strains will probably be effective in inducing memory innate immune responses. The data in Table 3 supports this since the challenge infections to which protection was conferred by vaccination with empty vector PIESV strains were 30 or more days after primary vaccination.

Note: During the course of research to discover and then improve use of live self-destructing *Salmonella* as adjuvants to enhance recruitment of innate immunity to augment eventual levels of acquired immunity, we simplified terminology from calling these Sal-Adj strains to ENIIRA strains to the simpler and more descriptive Self-Destructing Attenuated Adjuvant *Salmonella* (SDAAS) strains as used in the following examples.

Example 8. Additional Data Pertaining to Studies Demonstrating Enhancement of Levels of Protection Against *Mycobacterium tuberculosis* Challenge of Mice Inoculated with BCG with SDAAS Strain and a PIESV Delivering Mtb Antigens Studies on induction of immunity to *M. tuberculosis* (Mtb) infections are time-consuming due to the very slow growth of Mtb such that colony counts to determine bacterial densities require 4 weeks or so of incubation to obtain data. Thus, data from Experiments 14, 15 and 20 described in Example 5 continued for several months after the PCT application was filed. Analyses of induced immune responses in mice used in these studies also continued. FIG. 12 presents data on immune responses induced in Experiment 15. In this study, spleens were harvested and total CD3+ T cells were analyzed for ability to undergo proliferation in response to the mycobacterial antigen Ag85A using the CFSE dye dilution technology. Compared to the PBS control, lymphocytes from mice stimulated with BCG and the Family B strain $\chi$12518 showed slightly more proliferation than the T cells from mice co-inoculated with BCG and the Family A strain $\chi$12517. This same trend was also observed in regard to the ability of Ag85A to stimulate production of INFγ (FIG. 12). In accord with these findings in Experiment 15, we had also evaluated the $\chi$12517 and ×12518 cultures for their relative abilities to activate synthesis of NF-κB by interaction with TLR 4 and TLR5 displayed by HEK cells. Results shown in FIG. 13, demonstrate the clear superiority of the Family B strain $\chi$12518 for activation via both TLR4 and TLR5 and also does so in comparison to pure preparations of LPS and flagellin.

At the time of filing the PCT application, there were no colonies on plating undiluted spleen suspensions from mice inoculated with BCG and the Family B SDAAS strain $\chi$12518 independent of receiving the PIESV strain $\chi$12068 (pYA4891). We thought that maybe there was an inhibition in rate of growth due to the inoculation treatments so we only presented data from the lung suspension cultures (FIG. 11) and continued the incubation of plates for an additional two weeks (6 weeks in total). Still no colonies appeared on the plates with the undiluted spleen suspensions and we thus represent the data from lung cultures in FIG. 11 on an expanded ordinate scale in the left panel of FIG. 14 also displaying the results from the Mtb titers in the spleens of mice subjected to the different treatments in the right panel (using the same ordinate scale). The surprising and unexpected results were that combination of s.c. administration of BCG with i.v. administration of the Family B SDAAS strain $\chi$12518 at a dose of $5\times10^4$ CFU resulted in apparent inability of the aerosolized Mtb H37Rv to successfully traverse from the lung to systemic tissues such as the spleen or to be precluded from survival if getting to the spleen. Although induction of antibodies against mycobacterial proteins might not contribute to protective immunity against Mtb infections as would cellular immune responses, the co-administration of the SDAAS strain $\chi$12518 did enhance induction of antibody responses against Mtb antigens (FIG. 15). It should be emphasized that to the best of our knowledge the results presented in FIG. 14, demonstrating prevention of Mtb to colonize spleens after Mtb aerosol infection of vaccinated mice have never been observed by any investigator for any anti-Mtb vaccine. This offers the hope that co-administration of an SDAAS strain with BCG or some modified BSG or some other anti-Mtb vaccine could result in protective immunity to pulmonary tuberculosis in humans (a feat that BCG immunization alone is incapable of accomplishing). This, of course, will require evaluation in human clinical trials.

Example 9. Further Modifications of Family A and B SDAAS Strains to Investigate Effects of Additional Mutational Alterations to Enhance Safety and Effectiveness of Adjuvant Activities As described in Example 5, inoculation of the Family B SDAAS strain $\chi$12518 at a dose of $5\times10^4$ CFU i.v. caused significant splenomegaly that was not observed with oral or s.c inoculation and at lower doses by the i.v. route. As a consequence, we commenced to construct derivatives of the Family A strain $\chi$12517 and the Family B strain $\chi$12518 with additional mutations to enhance recruitment of innate immunity while reducing potential toxicity upon lysis of the strains in vivo. Many of these SDAAS strains with such modifications were listed in Tables 4 and 5 in Example 2 and additional SDAAS strains were constructed after filing of the PCT application. These newer AAS strains are included in Table 8 with the new mutations and their associated genotypes and phenotypes described in Table 6. Table 7 lists the suicide vectors used to generate the new AAS strains whose properties are presented and discussed in the following Examples.

Table 6. Additional Mutations with Associated Phenotypes Enhancing Adjuvant Activity and/or Safety of AAS Strains A. Deletion and Deletion-Insertion Mutations to Facilitate Regulated Delayed Lysis In Vivo $\Delta P_{asdA}$::TT rhaRS $P_{rhaBAD}$ asdA and $\Delta P_{asdA}$::TT $P_{rhaBAD}$ asdA make synthesis of AsdA dependent on presence of rhamnose.

$\Delta P_{dadB}$::TT rhaRS $P_{rhaBAD}$ dadB and $\Delta P_{dadB}$::TT $P_{rhaBAD}$ dadB make synthesis of DadB dependent on presence of rhamnose.

In one case the repression-activation of the $P_{rhaBAD}$ promoter can use the encoded *E. coli* rhaRS gene products or the endogenous *Salmonella* rhaRS gene products whereas in the case in which the *E. coli* rhaRS genes were excluded from the inserted regulatory cassette, the $P_{rhaBAD}$ is subject to control by only the *Salmonella* rhaRS gene products.

C. Mutations Altering Synthesis of LPS Components $\Delta$lpxR::$P_{lpp}$ lpxF mutation causes regulated delayed in vivo synthesis of the codon-optimized lpxF gene from *Francisella tularensis* to cause synthesis of the nontoxic adjuvant form of LPS lipid A that lacks the 4' phosphate on lipid A. The lpxR mutation eliminates a means by which *Salmonella* alters LPS lipid A in vivo to decrease recruitment of innate immunity by interaction with TLR4 (16)

Δpmi eliminates gene for phosphomannose isomerase such that LPS O-antigen synthesis is dependent on presence of non-phosphorylated mannose in growth medium (47)

Δrfc eliminates an enzyme that couples units of LPS O-antigen composed of 4 or 5 sugars to result in long-chain LPS O-antigen polymers (48)

ΔwbaP eliminates an enzyme needed to couple the first LPS O-antigen subunit onto the LPS core (49)

H. Mutations Enhancing Adjuvant Activity and Safety of Strains

ΔsopB decreases induction of inflammatory response for strains delivered on a mucosal surface (43) and increases induction of mucosal immunity (44)

ΔsopF enables *Salmonella* to escape the SCV (45)

ΔsseL decreases induction of pyroptosis (46)

ΔtlpA decreases induction of pyroptosis (46)

ΔpurA imposes an obligate requirement for non-phosphorylated adenine that is essential and absent in animal tissues; is thus totally attenuating (50)

The suicide vectors used to introduce the mutations listed in Table 6 into new AAS strains are listed in Table 7.

The new SDAAS strains constructed are listed in Table 8.

TABLE 7

Suicide vectors for constructing SDAAS strains with mutations listed in Table 6

A. Deletion and deletion-insertion mutations to facilitate regulated delayed lysis in vivo

| | | |
|---|---|---|
| $\Delta P_{dadB66}$::TT rhaRS $P_{rhaBAD2}$ dadB | pG8R340 | Cm |
| $\Delta P_{dadB66}$::TT rhaRS $P_{rhaBAD1}$ dadB | pG8R352 | Cm |
| $\Delta P_{dadB66}$::TT $P_{rhaBAD1}$ dadB | pG8R353 | Cm |
| $\Delta P_{asdA55}$::TT rhaRS $P_{rhaBAD1}$ asdA | pG8R354 | Cm |
| $\Delta P_{asdA55}$::TT $P_{rhaBAD1}$ asdA | pG8R355 | Cm |

C. Mutations altering synthesis of LPS components

| | | |
|---|---|---|
| $\Delta$lpxR:$P_{lpp}$ lpxF | pYA4289 | Cm |
| $\Delta$pmi | pYA3546 | Tet |
| $\Delta$rfc | pYA4717 | Cm |
| $\Delta$wbaP | pYA4899 | Cm |

H. Mutations enhancing adjuvant activity and safety of strains

| | | |
|---|---|---|
| $\Delta$sopB | pYA3733 | Cm |
| $\Delta$sopF | | |
| $\Delta$sseL | pYA4621 | Cm |
| $\Delta$tlpA | pYA4620 | Cm |
| $\Delta$purA | pG8R126 | Cm |

TABLE 8

Newly constructed AAS strains

Family A strains (genotypes and derivations)

| | | |
|---|---|---|
| χ12565 | Δalr-3 ΔdadB4 ΔasdA33 ΔfliC180 ΔpagP81::$P_{lpp}$ lpxE ΔpagL7 ΔlpxR9 ΔrecA62 | χ12517 |
| χ12606 | Δalr-3 ΔdadB4 ΔasdA33 ΔfliC180 Δ(hin-fljBA)-219 ΔpagP8 | χ12553 |
| χ12608 | Δalr-3 ΔdadB4 ΔasdA33 ΔfliC180 ΔpagP81::$P_{lpp}$ lpxE ΔpagL7 ΔlpxR9 ΔsifA26 | χ12517 |
| χ12625 | Δalr-3 ΔdadB4 ΔasdA33 ΔfliC180 Δ(hin-fljBA)-219 ΔpagP8 ΔlpxR9 | χ12606 |
| χ12629 | Δalr-3 ΔdadB4 ΔasdA33 ΔfliC180 Δ(hin-fljBA)-219 ΔpagP8 ΔlpxR9 ΔpagL7 | χ12625 |
| χ12638 | Δalr-3 ΔdadB4 ΔasdA33 ΔfliC180 Δ(hin-fljBA)-219 ΔpagP8 ΔlpxR9 ΔpagL7 ΔeptA4 | χ12629 |
| χ12640 | Δalr-3 ΔdadB4 ΔasdA33 ΔfliC180 Δ(hin-fljBA)-219 ΔpagP8 ΔlpxR9 ΔpagL7 ΔeptA4 ΔarnT6 | χ12638 |
| χ12650 | Δalr-3 ΔdadB4 ΔasdA33 ΔfliC180 Δ(hin-fljBA)-219 ΔpagP8 ΔlpxR9 ΔpagL7 Δepta4 ΔarnT6 Δsifa26 | χ12640 |
| χ12661 | Δalr-3 ΔdadB4 Δasda33 ΔfliC180 Δ(hin-fljBa)-219 ΔpagP8 ΔlpxR9 ΔpagL7 Δepta4 ΔarnT6 Δsifa26 ΔrecA62 | χ12650 |

Family B strains (genotypes and derivations)

| | | |
|---|---|---|
| χ12564 | Δalr-3 Δ$P_{dadB66}$::TT araC $P_{araBAD}$ dadB Δ$P_{asdA55}$::TT araC $P_{araBAD}$ asdA ΔfliC180 Δreca62 | χ12504 |
| χ12566 | Δalr-3 Δ$P_{dadB66}$::TT araC $P_{araBAD}$ dadB Δ$P_{asdA55}$::TT araC $P_{araBAD}$ asdA ΔfliC180 ΔpagP81::$P_{lpp}$ lpxE ΔpagL7 ΔlpxR9 ΔrecA62 | χ12518 |
| χ12567 | Δalr-3 Δ$P_{dadB66}$::TT araC $P_{araBAD}$ dadB Δ$P_{asdA55}$::TT araC $P_{araBAD}$ asdA ΔfliC180 ΔpagP81::$P_{lpp}$ lpxE ΔpagL7 ΔlpxR9 ΔwaaL46 ΔrecA62 | χ12544 |
| χ12568 | Δalr-3 Δ$P_{dadB66}$::TT araC $P_{araBAD}$ dadB Δ$P_{asdA55}$::TT araC $P_{araBAD}$ asdA ΔfliC180 ΔwaaL46 ΔrecA62 | χ12549 |
| χ12570 | Δalr-3 Δ$P_{dadB66}$::TT araC $P_{araBAD}$ dadB Δ$P_{asdA55}$::TT araC $P_{araBAD}$ asdA ΔfliC180 ΔpagP81::$P_{lpp}$ lpxE ΔpagL7 ΔlpxR9 ΔarnT6 | χ12518 |
| χ12571 | Δalr-3 Δ$P_{dadB66}$::TT araC $P_{araBAD}$ dadB Δ$P_{asdA55}$::TT araC $P_{araBAD}$ asdA ΔfliC180 ΔpagP81::$P_{lpp}$ lpxE ΔpagL7 ΔlpxR9 Δ(hin-fljBA)-219 ΔarnT6 | χ12548 |

TABLE 8-continued

| | Newly constructed AAS strains | |
|---|---|---|
| χ12583 | Δalr-3 ΔP$_{dadB66}$::TT araC P$_{araBAD}$ dadB Δ$_{PasdA55}$::TT araC P$_{araBAD}$ asdA ΔfliC180 ΔpagP81::P$_{lpp}$ lpxE ΔpagL7 ΔlpxR9 ΔeptA4 | χ12518 |
| χ12584 | Δalr-3 ΔP$_{dadB66}$::TT araC P$_{araBAD}$ dadB ΔP$_{asdA55}$::TT araC P$_{araBAD}$ asdA ΔfliC180 ΔpagP81::P$_{lpp}$ lpxE ΔpagL7 ΔlpxR9 Δ(hin-fljBA)-219 ΔeptA4 | χ12548 |
| χ12585 | Δalr-3 ΔP$_{dadB66}$::TT araC P$_{araBAD}$ dadB ΔP$_{asdA55}$::TT araC P$_{araBAD}$ asdA ΔfliC180 ΔpagP81::P$_{lpp}$ lpxE ΔpagL7 ΔlpxR9 Δ(hin-fljBA)-219 ΔarnT6 ΔeptA4 | χ12571 |
| χ12586 | Δalr-3 ΔP$_{dadB66}$::TT araC P$_{araBAD}$ dadB ΔP$_{asdA55}$::TT araC P$_{araBAD}$ asdA ΔfliC180 ΔpagP81::P$_{lpp}$ lpxE ΔpagL7 ΔlpxR9 ΔarnT6 ΔeptA4 | χ12570 |
| χ12603 | Δalr-3 ΔP$_{dadB66}$::TT araC P$_{araBAD}$ dadB ΔP$_{asdA55}$::TT araC P$_{araBAD}$ asdA ΔfliC180 Δ(hin-fljBA)-219 ΔpagP8 | χ12547 |
| χ12604 | Δalr-3 ΔP$_{dadB66}$::TT araC P$_{araBAD}$ dadB ΔP$_{asdA55}$::TT araC P$_{araBAD}$ asdA ΔfliC180 ΔpagP8 ΔpagL7 ΔlpxR9 Δ(hin-fljBA)-219 | χ12548 |
| χ12605 | Δalr-3 ΔP$_{dadB66}$::TT araC P$_{araBAD}$ dadB ΔP$_{asdA55}$::TT araC P$_{araBAD}$ asdA ΔfliC180 Δ(hin-fljBA)-219 ΔpagP8 ΔpagL7 | χ12603 |
| χ12609 | ΔP$_{asdA55}$::TT araC P$_{araBAD}$ asd Δalr-3 ΔP$_{dadB66}$::TT araC P$_{araBAD}$ dadB ΔfliC180 ΔpagP81::P$_{lpp}$ lpxE ΔpagL7 ΔlpxR9 ΔsifA26 | χ12518 |
| χ12610 | ΔP$_{asdA55}$::TT araC P$_{araBAD}$ asd Δalr-3 ΔP$_{dadB66}$::TT araC P$_{araBAD}$ dadB ΔfliC180 ΔpagP8 ΔpagL7 ΔlpxR9 Δ(hin-fljBA)-219 ΔsifA26 | χ12604 |
| χ12611 | ΔP$_{asdA55}$::TT araC P$_{araBAD}$ asd Δalr-3 ΔP$_{dadB66}$::TT araC P$_{araBAD}$ dadB ΔfliC180 ΔsifA26 | χ12504 |
| χ12612 | ΔP$_{asdA55}$::TT araC P$_{araBAD}$ asd Δalr-3 ΔP$_{dadB66}$::TT araC P$_{araBAD}$ dadB ΔfliC180 ΔpagP81::P$_{lpp}$ lpxE ΔpagL7 ΔlpxR9 Δ(hin-fljBA)-219 ΔarnT6 ΔeptA4 ΔsifA26 | ᴋ12585 |
| χ12620 | ΔP$_{asdA55}$::TT araC P$_{araBAD}$ asd Δalr-3 ΔP$_{dadB66}$::TT araC P$_{araBAD}$ dadB ΔfliC180 ΔpagP81::P$_{lpp}$ lpxE ΔpagL7 ΔlpxR9 Δ(hin-fljBA)-219 ΔarnT6 ΔeptA4 ΔsifA26 Δpmi-2426 | χ12612 |
| χ12621 | ΔP$_{asdA55}$::TT araC P$_{araBAD}$ asd Δalr-3 ΔP$_{dadB66}$::TT araC P$_{araBAD}$ dadB ΔfliC180 ΔpagP81::P$_{lpp}$ lpxE ΔpagL7 ΔlpxR9 Δ(hin-fljBA)-219 ΔarnT6 ΔeptA4 ΔsifA26 Δrfc-112 | χ12612 |
| χ12623 | Δalr-3 ΔP$_{dadB66}$::TT araC P$_{araBAD}$ dadB ΔP$_{asdA55}$::TT araC P$_{araBAD}$ asdA ΔfliC180 ΔpagP8 ΔpagL7 ΔlpxR9 Δ(hin-fljBA)-219 ΔeptA4 | χ12604 |
| χ12626 | ΔP$_{asdA55}$::TT araC P$_{araBAD}$ asd Δalr-3 ΔP$_{dadB66}$::TT araC P$_{araBAD}$ dadB ΔfliC180 ΔpagP81::P$_{lpp}$ lpxE ΔpagL7 ΔlpxR9 Δ(hin-fljBA)-219 ΔarnT6 ΔeptA4 ΔsifA26 ΔwbaP45 | χ12612 |
| χ12639 | Δalr-3 ΔP$_{dadB66}$::TT araC P$_{araBAD}$ dadB ΔP$_{asdA55}$::TT araC P$_{araBAD}$ asdA ΔfliC180 ΔpagP8 ΔpagL7 ΔlpxR9 Δ(hin-fljBA)-219 ΔeptA4 ΔarnT6 | χ12623 |
| χ12641 | ΔP$_{asdA55}$::TT araC P$_{araBAD}$ asd Δalr-3 ΔP$_{dadB66}$::TT araC P$_{araBAD}$ dadB ΔfliC180 ΔpagP81::P$_{lpp}$ lpxE ΔpagL7 ΔlpxR9 Δ(hin-fljBA)-219 ΔarnT6 ΔeptA4 ΔsifA26 ΔwaaL46 | χ12612 |
| χ12648 | ΔP$_{asdA55}$::TT araC P$_{araBAD}$ asd Δalr-3 ΔP$_{dadBxx}$::TT rhaSR P$_{rhaBAD}$ dadB ΔfliC180 ΔpagP81::P$_{lpp}$ lpxE ΔpagL7 ΔlpxR9 Δ(hin-fljBA)-219 ΔarnT6 ΔeptA4 ΔsifA26 | χ12612 |
| χ12649 | ΔP$_{asdA55}$::TT araC P$_{araBAD}$ asd Δalr-3 ΔP$_{dadBxx}$::TT rhaSR P$_{rhaBAD}$ dadB ΔfliC180 ΔpagP81::P$_{lpp}$ lpxE ΔpagL7 ΔlpxR9 Δ(hin-fljBA)-219 ΔarnT6 ΔeptA4 ΔsifA26 ΔwbaP45 | χ12626 |
| χ12668 | ΔP$_{asdA55}$::TT araC P$_{araBAD}$ asd Δalr-3 ΔP$_{dadB66}$::TT araC P$_{araBAD}$ dadB ΔfliC180 ΔpagP81::P$_{lpp}$ lpxE ΔpagL7 ΔlpxR9 Δ(hin-fljBA)-219 ΔarnT6 ΔeptA4 ΔsifA26 ΔrecA62 | χ12612 |
| χ12669 | ΔP$_{asdA55}$::TT araC P$_{araBAD}$ asd Δalr-3 ΔP$_{dadB66}$::TT araC P$_{araBAD}$ dadB ΔfliC180 ΔpagP81::P$_{lpp}$ lpxE ΔpagL7 ΔlpxR9 Δ(hin-fljBA)-219 ΔarnT6 ΔeptA4 ΔsifA26 ΔwbaP45 ΔrecA62 | χ12626 |

Example 10. Maximizing Synthesis and Delivery of a FliC Flagellin Subunit to Interact with TLR5 to Activate Induction of Innate Immunity The FliC180 flagellin subunit was derived by an internal deletion in the fliC gene that eliminated 180 amino acids with retention of the TLR5 binding domain. Also, this FliC180 subunit is secreted by the flagellar type 3 secretion system and since it does not polymerize into flagella, is available for interaction with cell-surface localized TLR5 molecules. It should be emphasized that it is flagellin and not flagella with capability of interacting with TLR5. Thus, SDAAS strains synthesizing and secreting the FliC180 subunit are more active in activating NF-κB in HEK cells displaying TLR5 than are wild-type strains synthesizing flagella (see FIG. 6 in Example 3) but are unable to exhibit motility (see FIG. 4). The wild-type motile strains are still capable of interacting with TLR5 however since not all flagellin is incorporated into flagella such that some free flagellin molecules exist to bind to TLR5. S. *Typhimurium* exhibits phase variation with regard to synthesis and display of flagellar antigens and shifts from synthesis of FliC to synthesis and assembly of FljB. The hin invertible element makes this transition about once in every $10^4$ cells in the population. Since we desired to have 100% of the SDAAS cells synthesizing and secreting the FliC180 subunit protein, we constructed the Δ(hin-fljBA)-219 phase-lock deletion mutation that also eliminates synthesis of the FljB flagellin and the FljA protein that is a repressor blocking transcription of the fliC gene in SDAAS strains. FIG. 16 presents western blot data showing the synthesis of the truncated FliC protein and the presence of the full-length FljB protein for strains without the Δ(hin-fljBA)-219 mutation. Since the N- and C-terminal ends of the FliC and FljB flagellins are essentially the same, the antibodies generated against the FliC180 subunit protein react equally well with the FljB and FliC flagellins. Note that the amount of FliC180 protein made is often reduced in cultures of those strains making the FljB flagellin. Also note that the wild-type parent χ3761 makes the full-length FliC flagellin. Although not shown, these same strains were analyzed with an antiserum against the middle portion of the full-length FliC flagellin and failed to react with the flagellins produced by all the strains with the fliC180 mutation. Also, all SDAAS strains used for the data presented in FIG. 16 activated NF-κB synthesis in HEK cells displaying TLR5.

FIG. 17 presents data on motility of all the strains used to obtain the FIG. 16 data. Thus, all stains with the ΔfliC180 and Δ(hin-fljBA)-219 mutations were non motile whereas the ΔfliC180 mutant strains with the wild-type fljB sequence displayed motility. Collectively, all these results indicate that SDAAS strains with both fliC180 and Δ(hin-fljBA)-219 mutations will be better adjuvants in stimulating innate immunity than strains without these mutations.

Example 11. Modifications in Synthesis of LPS Components Including Modifications of the Lipid A Endotoxin to Enhance Recruitment of Innate Immune Responses and Reduce Toxicity In Example 3 we noted that waaC and waaG mutations that eliminate the LPS O-antigen and truncate the LPS core enhance the ability of the Family B SDAAS strain χ12518 to exhibit enhanced abilities to activate NF-κB synthesis in HEK cells displaying TLR4 (FIG. 5). This was a positive result in that such mutants would display decreased virulence by being more readily phagocytized and more sensitive to complement mediated cytotoxicity. We therefore believed that such alterations would be doubly beneficial by reducing toxicity and induction of excessive splenomegaly while enhancing recruitment of innate immunity. However, it was surprisingly discovered that strains like χ12542 and χ12543 were less able to activate NF-κB synthesis in HEK cells displaying TLR5 and also decreased display of motility. We thus, devised other means to lessen toxicity while enhancing stimulation of innate immunity. Nevertheless, this observation that impairment in LPS core synthesis inhibited secretion of flagellin to preclude assembly and function of flagella is apparently a new discovery.

FIG. 18 diagrams the *Salmonella* lipid A molecule and indicates the gene products that modify the structure. The 1' and 4' phosphate groups contribute to invasiveness and toxicity. A synthetic derivative called MPLA for monophosphoryl lipid A is less toxic than lipid A and is used as an adjuvant for many vaccines currently under development. Some years ago, we expressed the *Francisella tularensis* lpxE gene in *S. Typhimurium* strains (15) to result is strains that produced mono-phosphoryl lipid A and we introduced the mutation ΔpagP81::$P_{lpp}$ lpxE into many SDAAS strains including χ12518, which nevertheless exhibited unwanted toxicity causing splenomegaly in mice inoculated with this SDAAS strain and BCG (see Examples 5 and 8). We therefore generated strains with various combinations of mutations as well as strains with single mutations ΔpagP8, ΔpagL7, ΔlpxR9, ΔarnT6 and ΔeptA4 since the products of these genes are used by *Salmonella* to modify lipid A to reduce its ability to interact with TLR4 and thus suppress induction of immunity and/or contribute to its toxicity. We therefore investigated the strains listed in Table 9 for toxicity using the Pierce Endotoxin Quantitation kit.

TABLE 9

| S. Typhimurium mutant strains evaluated for levels of endotoxicity |
| --- |
| 1. χ9429 ΔeptA4 |
| 2. χ9432 ΔarnT6 |
| 3. χ9486 ΔarnT ΔeptA |
| 4. χ9883 ΔpagL7 ΔpagP8 ΔlpxR9 ΔarnT6 |
| 5. χ9904 ΔpagL7 ΔpagP8 ΔlpxR9 ΔamT6 ΔeptA4 |
| 6. χ9430 ΔpagL7 |
| 7. χ9433 ΔlpxR9 |
| 8. χ9434 ΔpagP8 |
| 9. χ3761 wild-type UK-1 parent |

For these assays, strains were grown in LB broth overnight at 37° C. with aeration (180 rpm) and then diluted 1:10 into prewarmed LB broth and grown with continued aeration to an OD600 of 1.0 (~1×10⁹ CFU/ml). Bacterial cells were harvested by centrifugation, resuspended in endotoxin free water and disrupted by sonication. Cell lysates were diluted, distributed in 96 well plates and the successive reactions conducted according to the instructions provided with the Pierce Kit. Reactions were stopped and the results evaluated in a microplate absorbance reader at 405 nm. The results are presented in FIG. 19. All five of these mutations reduce endotoxicity with the combination ΔlpxR9, ΔarnT6 and ΔeptA4 giving the lowest endotoxin levels. Unexpectedly, inclusion of all 5 mutations in χ9904 displayed the lowest endotoxin activity. The surprising result depicted in FIG. 20 was the finding that no combination of these five mutations had an appreciable effect on interacting with TLR4 on HEK cells to activate NF-κB synthesis. The Family B SDAAS strain χ12585 Δalr-3 Δ$P_{dadB66}$::TT araC $P_{araBAD}$ dadB Δ$P_{asdA55}$::TT araC $P_{araBAD}$ asdA ΔfliC180 ΔpagP81::$P_{lpp}$ lpxE ΔpagL7 ΔlpxR9 Δ(hin-fljBA)-219 ΔarnT6 ΔeptA4 (Table 8) has these five genes deleted and, in addition, has the $P_{lpp}$ lpxE inserted into the ΔpagP mutation that should further decrease toxicity.

Example 12. Properties Associated with Constructed SDAAS Strains that should Further Enhance Adjuvant Activities and Safety Attributes The ΔsifA26 mutation enables *Salmonella* to escape the *Salmonella* containing vesicle (SCV) also termed the endosome and this enables all the SDAAS strains with programed abilities to undergo lysis in vivo to escape from the SCV to lyse in the cytosol. This lysis then liberates peptidoglycan constituents and DNA to interact with Nod1, Nod2, TLR8 and TLR9 that are located on internal cell surfaces (and are not available if lysis occurs within the SCV). It would thus be expected that Family A SDAAS strain χ12608, χ12650 and χ12661 (Table 8) and the Family B SDAAS strains χ12609, χ12610, χ12611, χ12612, χ12620, χ12621, χ12626, χ12641, χ12648, χ12649, χ12668 and χ12669 (Table 8) that all possess the ΔsifA26 mutation would exhibit an enhanced ability to activate NF-κB synthesis compared to SDAAS strains without this mutation. An added benefit is that S. *Typhimurium* strains with the ΔsifA26 mutation are more than 10,000 times less virulent when orally administered to mice compared to the wild-type parent. It is also possible that addition of a ΔsopF mutation (Table 6) in place of or in addition to the ΔsifA26 mutation will also be beneficial since the ΔsopF mutation also enables *Salmonella* to escape from the SCV to lyse in the cytosol.

The ΔrecA62 mutation eliminates the ability of *Salmonella* to carry out genetic recombination and results in increased sensitivity to UV and other stresses. The mutation also renders *Salmonella* more than 10,000 times less virulent than the wild-type parent after oral inoculation into mice. Importantly, genetic recombination is lethal with approximately 10% of the cells in the population degrading their entire DNA content as a consequence of progeny strand recombination. If this occurs in lysing AAS cells after escape from the SCV, there should be an increased release of CpG sequences targeting the internal TLR9 to activate NF-κB synthesis. This ΔrecA62 mutation has thus been introduced into the Family A SDAAS strain χ12565 and χ12661 the Family B SDAAS strains χ12566, χ12567, χ12568, χ12668 and χ12669 (Table 8) to enable testing of these expectations.

As stated in Example 10 and depicted in FIG. 18, the expression of the *F. tularensis* lpxF gene can eliminate the 4' phosphate on lipid A to reduce toxicity. As indicated in Table 7, we have generated the ΔlpxR::$P_{lpp}$ lpxF mutation and have the suicide vector pYA4289 to enable the introduction of this deletion-insertion mutation into a SDAAS strain to conduct tests as described in Example 10. We thus can compare toxicity and adjuvant activities of SDAAS strains with expression of neither, either of both *F. tularensis* lpxE and lpxF genes.

Although we observed that inability to synthesize the LPS O-antigen and part of the LPS core increased interaction with TLR4 (FIG. 5), mutations such as ΔwaaC41 and ΔwaaG42 caused an inhibition in FliC180 secretion and thus had an adverse effect on recruiting innate immunity via TLR5. We thus generated derivatives of Family B SDAAS strains such as χ12585 (Δalr-3 ΔP$_{dadB66}$::TT araC P$_{araBAD}$ dadB ΔP$_{asdA55}$::TT araC P$_{araBAD}$ asdA ΔfliC180 ΔpagP81:: P$_{lpp}$ lpxE ΔpagL7 ΔlpxR9 Δ(hin-fljBA)-219 ΔarnT6 ΔeptA4) or its derivative χ12612 with the ΔsifA26 mutation (Table 8) by addition of the Δpmi-2426 (χ12620), Δrfc-48 (χ12621), ΔwbaP45 (χ12626) and ΔwaaL46 (χ12641) mutations (Table 6). These strains are described in Table 8. The ΔwbaP45 and ΔwaaL46 mutations both block addition of the LPS O-antigen to the LPS core while the Δpmi-2426 mutation blocks the synthesis of GDP-mannose such that only the first two sugars of the first O-antigen subunit are attached to the LPS core and the Δrfc-48 mutation allows addition of the first O-antigen subunit to the core but precludes addition of additional O-antigen subunits. It is our expectation that all of these mutations will enhance innate immunity recruitment via interaction with TLR4 and that one or more of these mutations will also enable maximal secretion of the FliC180 subunit to activate innate immunity via TLR5 binding. Based on comparative studies for interactions with HEK cells displaying TLR4 and TLR5, we selected the ΔwbaP45 deletion strain χ12626 and added the ΔrecA62 mutation to yield χ12669 (Table 8). If desired, further safety can be provided by replacing a mutation for the arabinose-dependent expression of either the asdA or dadB genes with either the rhaRS P$_{rhaBAD}$ or P$_{rhaBAD}$ cassette which makes gene expression dependent on rhamnose as a second required sugar for AAS strain viability and survival.

The final outcome of these constructions and evaluations should result in SDAAS strains with maximal abilities to stimulate innate immunity by multiple pathways that will be completely attenuated (avirulent) and non-toxic (non-reactogenic) and thus enhance the immunogenicity of a diversity of subunit and live attenuated or live vectored vaccines to induce protective immunity.

Example 13. Evaluation of Family B Strains with Improvements Based on Inclusion of Mutations to Alter LPS Synthesis, Escape from SCV and Recombination Proficiency and DNA Stability In evaluating Family B strains with mutations altering LPS structure, we observed that strains χ12542 (ΔwaaC41) and ×12543 (ΔwaaG42) interacted with TLR4 on HEK cells at higher levels than their parent strain χ12518 (FIG. 5). However, their interaction with TLR5 on HEK cells was sharply reduced. Based on studies on contributions of various mutations in enhancing interactions with TLR5 (FIGS. 16 and 17) and reducing display of endotoxin activities (FIG. 19) without decreasing interaction with TLR4 (FIG. 20), we constructed as series of derivatives of the improved Family B strain χ12612 with complete display of the LPS core but in which the amount and structure of the LPS O-sidechain was altered. These strains χ12620 (Δpmi-2426), χ12621 (Δrfc-112), χ12626 (ΔwbaP45) and ×12641 (ΔwaaL46) (Table 8) were then evaluated for interaction with HEK cells displaying TLR4 and TLR5. FIG. 21 presents results from one experiment showing that all these strains activate NFκB as well or better than parent strain χ12612. (This study also included Family A strains to show that inclusion of mutations such as ΔpagP8, ΔlpxR9 and ΔpagL7 that reduce lipid A toxicity actually enhanced delivery of the FliC180 flagellin to activate synthesis of NFκB.) Since FliC180 should be secreted and released into the culture supernatant, we also tested strains with alterations in synthesis of LPS O-antigen for such release. However, since bacteria added to HEK cells continue to be metabolically active and produce flagellin, we conducted studies demonstrating that adding gentamicin at 100 µg/ml prevented such metabolic activity without altering TLR5 bearing HEK cells to be activated by flagellin present in culture supernatants containing 100 µg gentamicin/ml. FIG. 22 presents data that show that the χ12612 derivative strain χ12626 with the ΔwbaP45 mutation released the highest amount of the FliC180 flagellin into culture supernatant fluids.

We next evaluated all these strains (including the Family A strains with the ΔpagP8, ΔlpxR9 and ΔpagL7 mutations) for interaction with TLR4 on HEK cells. In this study (FIG. 23), χ12621 (Δrfc-112) and χ12626 (ΔwbaP45) were slightly better than the other strains, which was more apparent at earlier times of measurement than at later times. We also conducted a study on the assumption that the TLR4 binding ability to HEK cells would be bound to the surface of bacterial cells and not present in culture supernatants. To our surprise, this was not so as revealed by the data in FIG. 24 that demonstrate as much activity in the culture supernatant fluids as bound to cells. We believe that this is likely due to the continual release of outer membrane vesicles (OMVs) produced continuously during culture growth. Such OMVs that are like liposomes readily attach to host cells and are internalized. This newly discovered attribute in SDAAS strains is likely to be beneficial in enhancing recruitment of innate immune responses.

The Family B and A strains evaluated in the studies generating the data in FIGS. 21 and 23 were then tested for endotoxin assay in the same manner as used to generate the data in FIG. 19 (Example 11). As shown in FIG. 25, the wild-type χ3761, the pmi mutant χ12620 when grown with mannose to enable LPS O-antigen synthesis) and especially the rfc mutant χ12621 (which has a single O-antigen subunit) display the highest levels of endotoxin activities. The other Family A and B strains display the least endotoxin levels and especially χ12626, which we selected for further modifications to enhance abilities to recruit innate immune responses and display further attenuation and safety features.

For the studies to investigate activation of NFκB synthesis in HEK cells with TLR8 and TLR9, we selected Family A strains that rapidly lyse during infection of cells rather than Family B strains that display regulated delayed lysis features such that they will not lyse during the first 24 h after entry into host cells. As reveled by the results depicted in FIGS. 26 and 27, the Family A strain χ12640 and its derivatives χ12650 (with the ΔsifA26 mutation) and χ12661 (with the ΔsifA26 and ΔrecA62 mutations) all are very efficient in stimulating HEK cells with the internal TLR8 and TLR9 pattern receptors that recognize ssRNA and CpG sequences in DNA, respectively. These studies were conducted with MOIs of 10 and 1. We had expected an enhancement of activity dependent on adding the ΔsifA26 mutation to χ12640, but this was not observed, presumably since the cells lyse so rapidly and before an appreciable number of still intact cells could escape from the SCV to lyse in the cytosol. A similar inference likely explains the lack of observed enhancement of adding the ΔrecA62 mutation in enhancing activation in cells with TLR9. Whether addition of differing concentrations of DAP and D-alanine can enable any distinct differences in reactivity of these strains with HEK cells displaying TLR8 and TLR9 will be investigated. Evaluation of the addition of these two mutations to Family B strains will require animal studies to evaluate enhancement of adjuvant activities in increasing immune responses to antigens such as Ova, attenuated vaccines such as BCG and recombinant PIESV constructs delivering protective antigens from pathogens such as *Campylobacter jejuni*, *Clostridium perfringens*, *Streptococcus pneumoniae*, *Clostridium difficile*, *Eimeria species*, *Escherichia coli* pathovars and virus such as influenza.

Example 14. Selection of Family A and B Strains to Thoroughly Evaluate Adjuvant Activities in Animal Studies We have selected the Family A strain χ12661 (Δalr-3 ΔdadB4 ΔasdA33 ΔfliC180 Δ(hin-fljBA)-219 ΔpagP8 ΔlpxR9 ΔpagL7 ΔeptA4 ΔarnT6 ΔsifA26 ΔrecA62) and the Family B strain χ12669 (ΔP$_{asdA55}$::TT araC P$_{araBAD}$ asd Δalr-3 ΔP$_{dadB66}$::TT araC P$_{araBAD}$ dadB ΔfliC180 ΔpagP81:: P$_{lpp}$ lpxE ΔpagL7 ΔlpxR9 Δ(hin-fljBA)-219 ΔarnT6 ΔeptA4 ΔsifA26 ΔwbaP45 ΔrecA62) for the conduct of a diversity of animal studies analogous to those described in Examples 4 and 5 as well as other studies on enhancement of immune responses dependent on genotypes of PIESV vector strains comparing strains not lysing versus strains with rapid versus a much slower rate of in vivo regulated delayed lysis. We are also considering altering the Family B strain χ12669 to replace either the ΔP$_{asdA55}$::TT araC P$_{araBAD}$ asd or the ΔP$_{dadB66}$::TT araC P$_{araBAD}$ dadB mutation with a rhamnose regulated rhaRS P$_{rhaBAD}$ or P$_{rhaBAD}$ construction, respectively, using the suicide vectors pG8R340, pG8R352, pG8R353, pG8R354 or pG8R355 (Table 7). This will constitute an additional safety feature due to a requirement for two sugars for growth and infectivity not present in animal tissues.

REFERENCES

1. Kong W, Wanda S Y, Zhang X, Bollen W, Tinge S A, Roland K L, et al. Regulated programmed lysis of recombinant *Salmonella* in host tissues to release protective antigens and confer biological containment. Proc Natl Acad Sci USA. 2008; 105 (27): 9361-6.

2. Curtiss R, 3rd, Wanda S Y, Gunn B M, Zhang X, Tinge S A, Ananthnarayan V, et al. *Salmonella enterica* serovar *typhimurium* strains with regulated delayed attenuation in vivo. Infection and immunity. 2009; 77 (3): 1071-82.

3. Galan J E, Nakayama K, Curtiss R, 3rd. Cloning and characterization of the asd gene of *Salmonella typhimurium*: use in stable maintenance of recombinant plasmids in *Salmonella* vaccine strains. Gene. 1990; 94 (1): 29-35.

4. Xin W, Wanda S Y, Zhang X, Santander J, Scarpellini G, Ellis K, et al. The Asd(+)-DadB(+) dual-plasmid system offers a novel means to deliver multiple protective antigens by a recombinant attenuated *Salmonella* vaccine. Infection and immunity. 2012; 80 (10): 3621-33.

5. Stevenson G, Andrianopoulos K, Hobbs M, Reeves P R. Organization of the *Escherichia coli* K-12 gene cluster responsible for production of the extracellular polysaccharide colanic acid. J Bacteriol. 1996; 178 (16): 4885-93.

6. Whitfield C. Biosynthesis and assembly of capsular polysaccharides in *Escherichia coli*. Annual review of biochemistry. 2006; 75:39-68.

7. Pizarro-Cerda J, Tedin K. The bacterial signal molecule, ppGpp, regulates *Salmonella* virulence gene expression. Mol Microbiol. 2004; 52 (6): 1827-44.

8. Torok I, Kari C. Accumulation of ppGpp in a relA mutant of *Escherichia coli* during amino acid starvation. The Journal of biological chemistry. 1980; 255 (9): 3838-40.

9. Brosius J, Erfle M, Storella J. Spacing of the −10 and −35 regions in the tac promoter. Effect on its in vivo activity. J Biol Chem. 1985; 260 (6): 3539-41.

10. Amann E, Ochs B, Abel K-J. Tightly regulated tac promoter vectors useful for the expression of unfused and fused proteins in *Escherichia coli*. Gene. 1988; 69 (2): 301-15.

11. Wang S, Li Y, Scarpellini G, Kong W, Shi H, Baek C H, et al. *Salmonella* vaccine vectors displaying delayed antigen synthesis in vivo to enhance immunogenicity. Infect Immun. 2010; 78 (9): 3969-80.

12. Black S, Wright N G. Aspartic b-semialdehyde dehydrogenase and aspartic b-semialdehyde. J Biol Chem. 1955; 213 (1): 39-50.

13. Nakayama K, Kelly S M, Curtiss R, III Construction of an Asd$^+$ expression-cloning Vector: stable maintenance and high level expression of cloned genes in a *Salmonella* vaccine strain. Nat Biotech. 1988; 6 (6): 693-7.

14. Vander Byl C, Kropinski A M. Sequence of the genome of *Salmonella* bacteriophage P22. J Bacteriol. 2000; 182 (22): 6472-81.

15. Kong Q, Six D A, Roland K L, Liu Q, Gu L, Reynolds C M, et al. *Salmonella* synthesizing 1-dephosphorylated [corrected] lipopolysaccharide exhibits low endotoxic activity while retaining its immunogenicity. Journal of immunology (Baltimore, Md: 1950). 2011; 187 (1): 412-23.

16. Kong Q, Six D A, Liu Q, Gu L, Wang S, Alamuri P, et al. Phosphate groups of lipid A are essential for *Salmonella enterica* serovar *Typhimurium* virulence and affect innate and adaptive immunity. Infection and immunity. 2012; 80 (9): 3215-24.

17. Liu Q, Liu Q, Yi J, Liang K, Hu B, Zhang X, et al. Outer membrane vesicles from flagellin-deficient *Salmonella enterica* serovar *Typhimurium* induce cross-reactive immunity and provide cross-protection against heterologous *Salmonella* challenge. Scientific reports. 2016; 6:34776.

45

18. Laniewski P, Baek C H, Roland K L, Curtiss R, 3rd. Analysis of Spleen-Induced Fimbria Production in Recombinant Attenuated *Salmonella enterica* Serovar *Typhimurium* Vaccine Strains. mBio. 2017; 8 (4).
19. Beuzon C R, Meresse S, Unsworth K E, Ruiz-Albert J, Garvis S, Waterman S R, et al. *Salmonella* maintains the integrity of its intracellular vacuole through the action of SifA. The EMBO journal. 2000; 19 (13): 3235-49.
20. Ohlson M B, Huang Z, Alto N M, Blanc M P, Dixon J E, Chai J, et al. Structure and function of *Salmonella* SifA indicate that its interactions with SKIP, SseJ, and RhoA family GTPases induce endosomal tubulation. Cell host & microbe. 2008; 4 (5): 434-46.
21. Curtiss R, III., Porter S B, Munson M, Tinge S A, Hassan J O, Gentry-Weeks C, et al. Nonrecombinant and recombinant avirulent *Salmonella* live vaccines for poultry. In: Blankenship L C, Bailey J H S, Cox N A, Stern N J, Meinersmann R J, editors. Colonization control of human bacterial enteropathogens in poultry. New York Academic Press 1991. p. 169-98.
22. Bertani G. Studies on lysogenesis. I. The mode of phage liberation by lysogenic *Escherichia coli*. J Bacteriol. 1951; 62 (3): 293-300.
23. Sambrook J, Russell D W. Molecular cloning: a laboratory manual. 3rd ed. Cold Spring Harbor, N.Y.: Cold Spring Harbor Laboratory Press; 2001.
24. Schmieger H. Phage P22-mutants with increased or decreased transduction abilities. Mol Gen Genet. 1972; 119 (1): 75-88.
25. Schmieger H, Backhaus H. Altered cotransduction frequencies exhibited by HT-mutants of *Salmonella*-phage P22. Mol Gen Genet. 1976; 143 (3): 307-9.
26. Kang H Y, Dozois C M, Tinge S A, Lee T H, Curtiss R, III. Transduction-mediated transfer of unmarked deletion and point mutations through use of counter selectable suicide vectors. J Bacteriol. 2002; 184 (1): 307-12.
27. Edwards R A, Keller L H, Schifferli D M. Improved allelic exchange vectors and their use to analyze 987P fimbria gene expression. Gene. 1998; 207 (2): 149-57.
28. Quandt J, Hynes M F. Versatile suicide vectors which allow direct selection for gene replacement in gramnegative bacteria. Gene. 1993; 127 (1): 15-21.
29. Roland K, Curtiss R, III., Sizemore D. Construction and evaluation of a Dcya Derp *Salmonella typhimurium* strain expressing avian pathogenic *Escherichia coli* 078 LPS as a vaccine to prevent airsacculitis in chickens. Avian diseases. 1999; 43 (3): 429-41.
30. Kong Q, Liu Q, Roland K L, Curtiss R, III. Regulated delayed expression of rfaH in an attenuated *Salmonella enterica* serovar *Typhimurium* vaccine enhances immunogenicity of outer membrane proteins and a heterologous antigen. Infect Immun. 2009; 77 (12): 5572-82.
31. Juarez-Rodriguez M D, Arteaga-Cortes L T, Kader R, Curtiss R, 3rd, Clark-Curtiss J E. Live attenuated *Salmonella* vaccines against *Mycobacterium tuberculosis* with antigen delivery via the type III secretion system. Infection and immunity. 2012; 80 (2): 798-814.
32. Lee F K, Nahmias A J, Lowery S, Nesheim S, Reef S, Thompson S, et al. ELISPOT: a new approach to studying the dynamics of virus-immune system interaction for diagnosis and monitoring of HIV infection. AIDS research and human retroviruses. 1989; 5 (5): 517-23.
33. Park B S, Song D H, Kim H M, Choi B S, Lee H, Lee J O. The structural basis of lipopolysaccharide recognition by the TLR4-MD-2 complex. Nature. 2009; 458 (7242): 1191-5.

34. McCuskey R S, McCuskey P A, Urbaschek R, Urbaschek B. Species differences in Kupffer cells and endotoxin sensitivity. Infection and immunity. 1984; 45 (1): 278-80.
35. Baldridge M T, King K Y, Goodell M A. Inflammatory signals regulate hematopoietic stem cells. Trends in immunology. 2011; 32 (2): 57-65.
36. Essers M A, Offner S, Blanco-Bose W E, Waibler Z, Kalinke U, Duchosal M A, et al. IFNalpha activates dormant haematopoietic stem cells in vivo. Nature. 2009; 458 (7240): 904-8.
37. Takizawa H, Boettcher S, Manz M G. Demand-adapted regulation of early hematopoiesis in infection and inflammation. Blood. 2012; 119 (13): 2991-3002.
38. Belisle J T, Vissa V D, Sievert T, Takayama K, Brennan P J, Besra G S. Role of the major antigen of *Mycobacterium tuberculosis* in cell wall biogenesis. Science. 1997; 246:1420-1422.
39. Sorensen A L, Nagai S, Houen G, Andersen P, Andersen A B. Purification and characterization of a low molecular mass T-cell antigen secreted by *Mycobacterium tuberculosis*. Infection and immunity. 1995; 63:1710-1717.
40. Berthet F X, Rasmussen P B, Rosenkrands I, Andersen P, Gicquel B. A *Mycobacterium tuberculosis* operon encoding ESAT-6 and a novel low-molecular mass culture filtrate protein (CFP-10). Microbiology. 1998; 144:3195-3203.
41. Skjot R L, Oettinger, Rosenkrands I, Ravn P, Brock I, Jacobsen S, Andersen P. Comparative evaluation of low-molecular-mass proteins from *Mycobacterium tuberculosis* identifies members of the ESAT-6 family as immunodominant T-cell antigens. Infection and immunity. 2000; 68:214-220.
42. Ottenhoff T H, Doherty T M, van Dissel J T, Bang P, Lingnau K, Kromann I, Andersen P. First in humans: a new molecularly defined vaccine shows excellent safety and strong induction of long-lived *Mycobacterium tuberculosis*-specific Th1-cell like responses. Human Vaccines. 2010:6:1007-1015.
43. Gunn, B. M., S. Y. Wanda, D. Burshell, C. Wang, and R. Curtiss III. 2010. Construction of recombinant attenuated *Salmonella enterica* serovar *Typhimurium* vaccine vector strains for safety in newborn and infant mice. Clin. Vaccine Immunol. 17:354-362. PMCID: PMC2837962
44. Li, Y., S. Wang, W. Xin, G. Scarpellini, Z. Shi, B. Gunn, K. L. Roland, and R. Curtiss III. 2008. A sopB deletion mutation enhances the immunogenicity and protective efficacy of a heterologous antigen delivered by live attenuated *Salmonella enterica* vaccines. Infect. Immun. 76:5238-5246. PMCID: PMC2573344
45. Lau N, Haeberle A L, O'Keeffe B J, Latomanski E A, Celli J, Newton H J, Knodler L A. 2019. SopF, a phosphoinositide binding effector, promotes the stability of the nascent *Salmonella*-containing vacuole. PLOS Pathog. 2019 Jul. 24; 15 (7): e1007959. doi: 10.1371/journal.ppat.1007959. eCollection 2019
46. Kong, W., M. Brovold, B. A. Koneneman, J. Clark-Curtiss, and R. Curtiss III. 2012. Turning self-destructing *Salmonella* into a universal DNA vaccine delivery platform. Proc. Natl. Acad. USA 109:19414-19419. PMCID: PMC3511069
47. Curtiss, R. III, X. Zhang, S. Y. Wanda, H. Y. Kang, V. Konjufca, Y. Li, B. Gunn, S. Wang, G. Scarpellini, and I. S. Lee. 2007. Induction of host immune responses using *Salmonella*-vectored vaccines, p. 297-313. In K. A. Brogden, F. C. Minion, N. Cornick, T. B. Stanton, Q. Zhang, L. K. Nolan, and M. J. Wannemuehler (eds.).

Virulence Mechanisms of Bacterial Pathogens, $4^{th}$ ed., ASM Press, Washington, D.C.

48. Kong, Q., Q. Liu, A. M. Jansen, and R. Curtiss III. 2010. Regulated delayed expression of rfc enhances the immunogenicity and protective efficacy of a heterologous antigen delivered by live attenuated *Salmonella enterica* vaccines. Vaccine 28:6094-6103. PMCID: PMC3956130

49. Kong, Q., J. Yang, Q. Liu, P. Alamuri, K. L. Roland, and R. Curtiss III. 2011. Effect of deletion of genes involved in lipopolysaccharide core and O-antigen synthesis on virulence and immunogenicity of *Salmonella enterica* serovar *Typhimurium*. Infect. Immun. 79:4227-4239. PMCID: PMC3187260

50. O'Callaghan D, Maskell D, Liew F Y, Easmon C S, Dougan G. 1988. Characterization of aromatic- and purine-dependent *Salmonella typhimurium*: attention, persistence, and ability to induce protective immunity in BALB/c mice. Infect Immun. 56 (2): 419-23.

51 Trent, M. S., A. A. Ribeiro, S. Lin, R. J. Cotter, and C. R. H. Raetz. 2001. An inner membrane in *Salmonella* and *Escherichia coli* that transfers 4-amino-4-deoxy-L-arabinose to lipid A: induction of polymyxin-resistant mutants and role of a novel lipid-linked donor. J. Biol. Chem. 276:43122-43131.

52. Herrera, C. M., J. V. Hankins, and M. S. Trent. 2010. Activation of PmrA inhibits LpxT-dependent phosphorylation of lipid A promoting resistance to antimicrobial peptides. Mol. Microbiol. 76:1444-1460.

53. Buchmeier, N. A., C. J. Lipps, M. Y. So, and F. Heffron. 1993. Recombination-deficient mutants of *Salmonella typhimurium* are avirulent and sensitive to the oxidative burst of macrophages. Mol. Microbiol. 7:933-936.

What is claimed is:

1. An adjuvant for the enhancement of vaccine efficacy, the adjuvant comprising an attenuated derivative of a bacterial pathogen that undergoes lysis in vivo, wherein the adjuvant comprises an attenuated *Salmonella typhimurium* (*S. typhimurium*) bacterium, comprising (a) one or more mutations facilitating lysis in vivo, comprising (i) $\Delta P_{murA}$:: TT rhaRS $P_{rhaBAD}$ murA, and/or (ii) a combination of $\Delta P_{asdA}$::TT araC $P_{araBAD}$ asdA or $\Delta P_{asdA}$::TT rhaRS $P_{rhaBAD}$ asdA, $\Delta$alr, and $\Delta P_{dadB}$::TT rhaRS $P_{rhaBAD}$ dadB; and, optionally, a combination of (a) with (b) or (c), wherein (b) is one or more mutations to enhance recruitment of innate immunity comprising (i) $\Delta$pagP::$P_{lpp}$ lpxE and/or $\Delta$lpxR:: $P_{lpp}$ lpxF, (ii) $\Delta$pagL or $\Delta$pagP or (iii) $\Delta$lpxR, $\Delta$arnT, $\Delta$eptA, $\Delta$waaC, $\Delta$waaG, $\Delta$waaL, $\Delta$wbaP, $\Delta$pmi or $\Delta$rfc or a combination thereof; or (iv) $\Delta P_{stc}$::$P_{murA}$ stc and $\Delta$stcABCD or $\Delta P_{saf}$:$P_{murA}$ saf and $\Delta$safABCD, or a combination thereof, and wherein (c) is a mutation enhancing safety and effective immunogenicity, comprising $\Delta$sifA, $\Delta$sopF, $\Delta$recA or $\Delta$sopB.

2. The adjuvant of claim 1, wherein the adjuvant comprises a self-destructing attenuated *Salmonella typhimurium* (*S. typhimurium*) bacterium, comprising the $\Delta$pagP::$P_{lpp}$ lpxE mutations.

3. The adjuvant of claim 2, wherein the adjuvant also comprises $\Delta$pagL and $\Delta$lpxR or $\Delta$arnT and $\Delta$eptA mutations.

4. The adjuvant of claim 2, wherein the adjuvant also comprises $\Delta$waaC, $\Delta$waaG, $\Delta$waaL or $\Delta$wbaP mutations.

5. The adjuvant of claim 2, wherein the adjuvant also comprises a $\Delta$sifA mutation.

6. The adjuvant of claim 2, wherein the adjuvant also comprises a $\Delta$recA mutation.

7. The adjuvant of claim 1, wherein the adjuvant also comprises (i) $\Delta$pagP::$P_{lpp}$ lpxE and/or $\Delta$lpxR::$P_{lpp}$ lpxF mutations, (ii) $\Delta$pagL and $\Delta$lpxR or $\Delta$arnT and $\Delta$eptA mutations, (iii) $\Delta$waaC, $\Delta$waaG, $\Delta$waaL or $\Delta$wbaP mutations, (iv) a $\Delta$sifA mutation, (v) a $\Delta$recA mutation, or (vi) $\Delta P_{stc}$::$P_{murA}$ stc and/or $\Delta P_{saf}$:$P_{murA}$ saf mutations.

8. The adjuvant of claim 1 further comprising a $\Delta$relA mutation to dissociate growth leading to lysis being dependent on protein synthesis.

9. The adjuvant of claim 1 further comprising a $\Delta$relA mutation to dissociate growth leading to lysis being dependent on protein synthesis.

10. A method of augmenting induction of protective immunity by a vaccine, the method comprising administering an immune response enhancing amount of the adjuvant of claim 2.

11. A method of augmenting induction of protective immunity by a vaccine, the method comprising administering an immune response enhancing amount of the adjuvant of claim 1.

12. The method of claim 10, wherein the adjuvant is administered by a route of administration comprising oral, intradermal, intravenous, intramuscular, intraocular, intranasal, intrapulmonary, epidermal, subcutaneous, mucosal, or transcutaneous administration.

13. The method of claim 11, wherein the adjuvant is administered by a route of administration comprising oral, intradermal, intravenous, intramuscular, intraocular, intranasal, intrapulmonary, epidermal, subcutaneous, mucosal, or transcutaneous administration.

* * * * *